(12) United States Patent
Overmyer et al.

(10) Patent No.: US 10,588,626 B2
(45) Date of Patent: Mar. 17, 2020

(54) SURGICAL INSTRUMENT DISPLAYING SUBSEQUENT STEP OF USE

(71) Applicant: Ethicon LLC, Guaynabo, PR (US)

(72) Inventors: Mark D. Overmyer, Cincinnati, OH (US); Brett E. Swensgard, West Chester, OH (US); Shane R. Adams, Lebanon, OH (US); Thomas W. Lytle, IV, Liberty Township, OH (US); Richard L. Leimbach, Cincinnati, OH (US); Frederick E. Shelton, IV, Hillsboro, OH (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 194 days.

(21) Appl. No.: 15/459,515

(22) Filed: Mar. 15, 2017

(65) Prior Publication Data

US 2017/0209226 A1 Jul. 27, 2017

Related U.S. Application Data

(63) Continuation of application No. 14/226,126, filed on Mar. 26, 2014, now Pat. No. 10,004,497.

(51) Int. Cl.
*A61B 17/068* (2006.01)
*G16H 40/63* (2018.01)
(Continued)

(52) U.S. Cl.
CPC ...... *A61B 17/068* (2013.01); *A61B 17/07207* (2013.01); *A61B 34/25* (2016.02);
(Continued)

(58) Field of Classification Search
CPC ....... A61B 17/068; A61B 34/25; A61B 90/98; A61B 17/07207; G16H 10/60; G16H 40/63; G06F 19/00
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2011218702 B2 6/2013
AU 2012200178 B2 7/2013
(Continued)

OTHER PUBLICATIONS

Data Sheet of LM4F230H5QR, 2007.
(Continued)

*Primary Examiner* — Nathaniel C Chukwurah

(57) ABSTRACT

A surgical instrument including a shaft, an end effector extending distally from the shaft, a display, and a system or sensor configured to monitor a status of the surgical instrument. The display is configured to display information pertaining to the detected status of the surgical instrument. In one embodiment, the display displays a subsequent step of operating the surgical instrument. In another embodiment, the display displays a subsequent step of assembling the surgical instrument. The display is additionally configured to enter a low-power mode.

19 Claims, 35 Drawing Sheets

(51) Int. Cl.

| | |
|---|---|
| *G16H 10/60* | (2018.01) |
| *A61B 17/072* | (2006.01) |
| *A61B 90/98* | (2016.01) |
| *G05B 19/05* | (2006.01) |
| *A61B 34/00* | (2016.01) |
| *G06F 19/00* | (2018.01) |
| *A61B 17/00* | (2006.01) |
| *A61B 17/29* | (2006.01) |
| *A61B 90/00* | (2016.01) |
| *G16H 20/40* | (2018.01) |

(52) U.S. Cl.
CPC .............. *A61B 90/98* (2016.02); *G05B 19/05* (2013.01); *G06F 19/00* (2013.01); *G16H 10/60* (2018.01); *G16H 40/63* (2018.01); *A61B 2017/00017* (2013.01); *A61B 2017/0046* (2013.01); *A61B 2017/00115* (2013.01); *A61B 2017/00199* (2013.01); *A61B 2017/00212* (2013.01); *A61B 2017/00221* (2013.01); *A61B 2017/00225* (2013.01); *A61B 2017/00398* (2013.01); *A61B 2017/00482* (2013.01); *A61B 2017/2927* (2013.01); *A61B 2090/0805* (2016.02); *A61B 2090/0807* (2016.02); *A61B 2090/0808* (2016.02); *A61B 2090/0811* (2016.02); *G05B 2219/14018* (2013.01); *G06F 19/3481* (2013.01); *G16H 20/40* (2018.01); *Y10T 29/49826* (2015.01)

(58) Field of Classification Search
USPC .......................... 227/177.1, 178.1, 176.1, 19
See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,188,721 A | 6/1916 | Bittner |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |

(56) References Cited

U.S. PATENT DOCUMENTS

| | | |
|---|---|---|
| 3,972,734 A | 8/1976 | King |
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |

(56) References Cited

U.S. PATENT DOCUMENTS

| | | |
|---|---|---|
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |

(56) References Cited

U.S. PATENT DOCUMENTS

| | | |
|---|---|---|
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |

(56) References Cited

U.S. PATENT DOCUMENTS

| | | |
|---|---|---|
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,293,024 A | 3/1994 | Sugahara et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |

(56) References Cited

U.S. PATENT DOCUMENTS

| | | |
|---|---|---|
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |

(56) References Cited

U.S. PATENT DOCUMENTS

| | | |
|---|---|---|
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |

(56) References Cited

U.S. PATENT DOCUMENTS

| | | |
|---|---|---|
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |

(56) References Cited

U.S. PATENT DOCUMENTS

| | | |
|---|---|---|
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |

(56) References Cited

U.S. PATENT DOCUMENTS

| | | |
|---|---|---|
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |

(56) References Cited

U.S. PATENT DOCUMENTS

| | | |
|---|---|---|
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |

(56) References Cited

U.S. PATENT DOCUMENTS

| | | |
|---|---|---|
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |

(56) References Cited

U.S. PATENT DOCUMENTS

| | | |
|---|---|---|
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |

(56) References Cited

U.S. PATENT DOCUMENTS

| | | |
|---|---|---|
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |

(56) References Cited

U.S. PATENT DOCUMENTS

| | | |
|---|---|---|
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |

(56) References Cited

U.S. PATENT DOCUMENTS

| | | |
|---|---|---|
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,450,010 B1 | 11/2008 | Gravelle et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barley et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |

(56) References Cited

U.S. PATENT DOCUMENTS

| | | |
|---|---|---|
| 7,615,067 B2 | 11/2009 | Lee et al. |
| 7,617,961 B2 | 11/2009 | Viola |
| D605,201 S | 12/2009 | Lorenz et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |

(56) References Cited

U.S. PATENT DOCUMENTS

| | | |
|---|---|---|
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |

(56) References Cited

U.S. PATENT DOCUMENTS

| | | |
|---|---|---|
| 7,934,631 B2 | 5/2011 | Balbierz et al. |
| 7,934,896 B2 | 5/2011 | Schnier |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |

(56) References Cited

U.S. PATENT DOCUMENTS

| | | |
|---|---|---|
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |

(56) References Cited

U.S. PATENT DOCUMENTS

| | | |
|---|---|---|
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,487 B2 | 10/2012 | Estes |
| 8,287,522 B2 | 10/2012 | Moses et al. |
| 8,287,561 B2 | 10/2012 | Nunez et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,801 B2 | 10/2012 | Dejima et al. |
| 8,292,888 B2 | 10/2012 | Whitman |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |

(56) References Cited

U.S. PATENT DOCUMENTS

| | | |
|---|---|---|
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |

(56) References Cited

U.S. PATENT DOCUMENTS

| | | |
|---|---|---|
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |

(56) References Cited

U.S. PATENT DOCUMENTS

| | | |
|---|---|---|
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |

(56) References Cited

U.S. PATENT DOCUMENTS

| | | |
|---|---|---|
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,985,429 B2 | 3/2015 | Balek et al. |
| 8,986,302 B2 | 3/2015 | Aldridge et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,099,877 B2 | 8/2015 | Banos et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |

(56) References Cited

U.S. PATENT DOCUMENTS

| | | |
|---|---|---|
| 9,161,807 B2 | 10/2015 | Garrison |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,244,524 B2 | 1/2016 | Inoue et al. |
| D748,668 S | 2/2016 | Kim et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,345,477 B2 | 5/2016 | Anim et al. |
| 9,345,480 B2 | 5/2016 | Hessler et al. |

(56) References Cited

U.S. PATENT DOCUMENTS

| | | |
|---|---|---|
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| D759,063 S | 6/2016 | Chen |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,427,223 B2 | 8/2016 | Park et al. |
| 9,427,231 B2 | 8/2016 | Racenet et al. |
| D767,624 S | 9/2016 | Lee et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,446,226 B2 | 9/2016 | Zilberman |
| 9,451,938 B2 | 9/2016 | Overes et al. |
| 9,451,958 B2 | 9/2016 | Shelton, IV et al. |
| D768,152 S | 10/2016 | Gutierrez et al. |
| D768,156 S | 10/2016 | Frincke |
| D769,315 S | 10/2016 | Scotti |
| D769,930 S | 10/2016 | Agrawal |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,483 B2 | 11/2016 | Houser et al. |
| 9,504,521 B2 | 11/2016 | Deutmeyer et al. |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| D776,683 S | 1/2017 | Gobinski et al. |
| D777,773 S | 1/2017 | Shi |
| 9,532,783 B2 | 1/2017 | Swayze et al. |
| 9,539,726 B2 | 1/2017 | Simaan et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| D780,803 S | 3/2017 | Gill et al. |
| D781,879 S | 3/2017 | Butcher et al. |

(56) References Cited

U.S. PATENT DOCUMENTS

| | | |
|---|---|---|
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,111 B2 | 5/2017 | Wenchell |
| 9,636,850 B2 | 5/2017 | Stopek et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,005 B2 | 7/2017 | Strobl et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,635 B2 | 10/2017 | Takei |

(56) References Cited

U.S. PATENT DOCUMENTS

| | | |
|---|---|---|
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,561 B2 | 11/2017 | Forsell |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| D810,099 S | 2/2018 | Riedel |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| D819,072 S | 5/2018 | Clediere |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |

(56) References Cited

U.S. PATENT DOCUMENTS

| | | |
|---|---|---|
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,728 B2 | 10/2018 | Jogasaki et al. |
| 10,085,748 B2 | 10/2018 | Morgan et al. |
| 10,085,749 B2 | 10/2018 | Cappola et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,111,679 B2 | 10/2018 | Baber et al. |
| 10,111,702 B2 | 10/2018 | Kostrzewski |
| 10,117,649 B2 | 11/2018 | Baxter, III et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,154,841 B2 | 12/2018 | Weaner et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| D837,244 S | 1/2019 | Kuo et al. |
| D837,245 S | 1/2019 | Kuo et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| D839,900 S | 2/2019 | Gan |
| D841,667 S | 2/2019 | Coren |
| 10,194,904 B2 | 2/2019 | Viola et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |

(56) References Cited

U.S. PATENT DOCUMENTS

| | | |
|---|---|---|
| 10,206,678 B2 | 2/2019 | Shelton, IV et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,262 B2 | 2/2019 | Shelton, IV et al. |
| D842,328 S | 3/2019 | Jian et al. |
| 10,219,832 B2 | 3/2019 | Bagwell et al. |
| 10,220,522 B2 | 3/2019 | Rockrohr |
| 10,226,249 B2 | 3/2019 | Jaworek et al. |
| 10,226,250 B2 | 3/2019 | Beckman et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,058 B2 | 4/2019 | Omori et al. |
| 10,251,648 B2 | 4/2019 | Harris et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,074 B2 | 4/2019 | Shelton, IV et al. |
| 10,265,090 B2 | 4/2019 | Ingmanson et al. |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,577 B2 | 6/2019 | Laurent et al. |
| 10,314,582 B2 | 6/2019 | Shelton, IV et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,342,533 B2 | 7/2019 | Shelton, IV et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,939 B2 | 7/2019 | Shelton, IV et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,841 B2 | 8/2019 | Shelton, IV et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |

(56) References Cited

U.S. PATENT DOCUMENTS

| | | |
|---|---|---|
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |

(56) References Cited

U.S. PATENT DOCUMENTS

| | | |
|---|---|---|
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |

(56) References Cited

U.S. PATENT DOCUMENTS

| | | |
|---|---|---|
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1* | 4/2009 | Zemlok ............ A61B 17/07207 227/175.2 |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2010/0005035 A1 | 1/2010 | Carpenter et al. |
| 2010/0012703 A1 | 1/2010 | Calabrese et al. |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0241137 A1 | 9/2010 | Doyle et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |

(56) References Cited

U.S. PATENT DOCUMENTS

| | | |
|---|---|---|
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0204119 A1* | 8/2011 | McCuen ......... A61B 17/07207 227/175.1 |
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 11/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078139 A1 | 3/2012 | Aldridge et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1* | 2/2013 | Cunningham ......... A61B 18/12 601/2 |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105552 A1 | 5/2013 | Weir et al. |
| 2013/0106352 A1 | 5/2013 | Nagamine |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172878 A1 | 7/2013 | Smith |
| 2013/0175317 A1 | 7/2013 | Yates et al. |
| 2013/0214025 A1 | 8/2013 | Zemlok et al. |
| 2013/0233906 A1 | 9/2013 | Hess et al. |
| 2013/0238021 A1 | 9/2013 | Gross et al. |
| 2013/0245704 A1 | 9/2013 | Koltz et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0317753 A1 | 11/2013 | Kamen et al. |
| 2013/0324982 A1 | 12/2013 | Smith et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107640 A1 | 4/2014 | Yates et al. |
| 2014/0110456 A1 | 4/2014 | Taylor |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0207125 A1 | 7/2014 | Applegate et al. |
| 2014/0209658 A1 | 7/2014 | Skalla et al. |
| 2014/0224857 A1 | 8/2014 | Schmid |
| 2014/0228867 A1 | 8/2014 | Thomas et al. |
| 2014/0230595 A1 | 8/2014 | Butt et al. |

(56) References Cited

U.S. PATENT DOCUMENTS

| | | |
|---|---|---|
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0252061 A1 | 9/2014 | Estrella et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0309666 A1 | 10/2014 | Shelton, IV et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0088547 A1 | 3/2015 | Balram et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0108199 A1 | 4/2015 | Shelton, IV et al. |
| 2015/0122870 A1 | 5/2015 | Zemlok et al. |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter et al. |
| 2015/0173789 A1 | 6/2015 | Baxter et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196348 A1 | 7/2015 | Yates et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0223868 A1 | 8/2015 | Brandt et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272604 A1 | 10/2015 | Chowaniec et al. |
| 2015/0273671 A1 | 10/2015 | Totsu |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0302539 A1 | 10/2015 | Mazar et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0336249 A1 | 11/2015 | Iwata et al. |
| 2015/0352699 A1 | 12/2015 | Sakai et al. |
| 2015/0366585 A1 | 12/2015 | Lemay et al. |
| 2015/0372265 A1 | 12/2015 | Morisaku et al. |
| 2015/0374361 A1 | 12/2015 | Gettinger et al. |
| 2015/0374369 A1 | 12/2015 | Yates et al. |
| 2015/0374371 A1 | 12/2015 | Richard et al. |
| 2015/0374372 A1 | 12/2015 | Zergiebel et al. |
| 2015/0374378 A1 | 12/2015 | Giordano et al. |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0023342 A1 | 1/2016 | Koenig et al. |
| 2016/0030042 A1 | 2/2016 | Heinrich et al. |
| 2016/0051257 A1 | 2/2016 | Shelton, IV et al. |
| 2016/0058443 A1 | 3/2016 | Yates et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089146 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166248 A1 | 6/2016 | Deville et al. |
| 2016/0166256 A1 | 6/2016 | Baxter, III et al. |
| 2016/0166308 A1 | 6/2016 | Manwaring et al. |
| 2016/0174974 A1 | 6/2016 | Schmid et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192960 A1 | 7/2016 | Bueno et al. |
| 2016/0192977 A1 | 7/2016 | Manwaring et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220266 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235409 A1 | 8/2016 | Shelton, IV et al. |
| 2016/0235467 A1 | 8/2016 | Godara et al. |

(56) References Cited

U.S. PATENT DOCUMENTS

| | | |
|---|---|---|
| 2016/0235494 A1 | 8/2016 | Shelton, IV et al. |
| 2016/0242777 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249910 A1 | 9/2016 | Shelton, IV et al. |
| 2016/0249922 A1 | 9/2016 | Morgan et al. |
| 2016/0256071 A1 | 9/2016 | Shelton, IV et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0287253 A1 | 10/2016 | Shelton, IV et al. |
| 2016/0287279 A1 | 10/2016 | Bovay et al. |
| 2016/0310134 A1 | 10/2016 | Contini et al. |
| 2016/0310143 A1 | 10/2016 | Bettuchi |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367255 A1 | 12/2016 | Wise et al. |
| 2016/0374672 A1 | 12/2016 | Bear et al. |
| 2016/0374675 A1 | 12/2016 | Shelton, IV et al. |
| 2016/0374678 A1 | 12/2016 | Becerra et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0056006 A1 | 3/2017 | Shelton, IV et al. |
| 2017/0079642 A1 | 3/2017 | Overmyer et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0095250 A1 | 4/2017 | Kostrzewski et al. |
| 2017/0119386 A1 | 5/2017 | Scheib et al. |
| 2017/0119390 A1 | 5/2017 | Schellin et al. |
| 2017/0119392 A1 | 5/2017 | Shelton, IV et al. |
| 2017/0119397 A1 | 5/2017 | Harris et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172382 A1 | 6/2017 | Nir et al. |
| 2017/0172550 A1 | 6/2017 | Mukherjee et al. |
| 2017/0172662 A1 | 6/2017 | Panescu et al. |
| 2017/0172672 A1 | 6/2017 | Bailey et al. |
| 2017/0182211 A1 | 6/2017 | Raxworthy et al. |
| 2017/0196558 A1 | 7/2017 | Morgan et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0215881 A1 | 8/2017 | Shelton, IV et al. |
| 2017/0215943 A1 | 8/2017 | Allen, IV |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0231633 A1 | 8/2017 | Marczyk et al. |
| 2017/0238928 A1 | 8/2017 | Morgan et al. |
| 2017/0238929 A1 | 8/2017 | Yates et al. |
| 2017/0245854 A1 | 8/2017 | Zemlok et al. |
| 2017/0245952 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281155 A1 | 10/2017 | Shelton, IV et al. |
| 2017/0281162 A1 | 10/2017 | Shelton, IV et al. |
| 2017/0281164 A1 | 10/2017 | Harris et al. |
| 2017/0281166 A1 | 10/2017 | Morgan et al. |
| 2017/0281167 A1 | 10/2017 | Shelton, IV et al. |
| 2017/0281168 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281179 A1 | 10/2017 | Shelton, IV et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290584 A1 | 10/2017 | Jasemian et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296173 A1 | 10/2017 | Harris et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296185 A1 | 10/2017 | Swensgard et al. |
| 2017/0296189 A1 | 10/2017 | Vendely et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0325813 A1 | 11/2017 | Aranyi et al. |
| 2017/0333034 A1 | 11/2017 | Morgan et al. |

(56) References Cited

U.S. PATENT DOCUMENTS

| | | |
|---|---|---|
| 2017/0333035 A1 | 11/2017 | Morgan et al. |
| 2017/0333070 A1 | 11/2017 | Laurent et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0354415 A1 | 12/2017 | Casasanta, Jr. et al. |
| 2017/0358052 A1 | 12/2017 | Yuan |
| 2017/0360441 A1 | 12/2017 | Sgroi |
| 2017/0360442 A1 | 12/2017 | Shelton, IV et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0078248 A1 | 3/2018 | Swayze et al. |
| 2018/0078268 A1 | 3/2018 | Messerly et al. |
| 2018/0085116 A1 | 3/2018 | Yates et al. |
| 2018/0085117 A1 | 3/2018 | Shelton, IV et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132926 A1 | 5/2018 | Asher et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |

(56) References Cited

U.S. PATENT DOCUMENTS

| | | |
|---|---|---|
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0250020 A1 | 9/2018 | Carusillo |
| 2018/0256184 A1 | 9/2018 | Shelton, IV et al. |
| 2018/0271520 A1 | 9/2018 | Shelton, IV et al. |
| 2018/0273597 A1 | 9/2018 | Stimson |
| 2018/0280020 A1 | 10/2018 | Hess et al. |
| 2018/0286274 A1 | 10/2018 | Kamiguchi et al. |
| 2018/0289369 A1 | 10/2018 | Shelton, IV et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317907 A1 | 11/2018 | Kostrzewski |
| 2018/0317916 A1 | 11/2018 | Wixey |
| 2018/0317917 A1 | 11/2018 | Huang et al. |
| 2018/0317918 A1 | 11/2018 | Shelton, IV |
| 2018/0317919 A1 | 11/2018 | Shelton, IV et al. |
| 2018/0325528 A1 | 11/2018 | Windolf et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV et al. |
| 2018/0360450 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0360549 A1 | 12/2018 | Hares et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000458 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000468 A1 | 1/2019 | Adams et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000531 A1 | 1/2019 | Messerly et al. |
| 2019/0000534 A1 | 1/2019 | Messerly et al. |
| 2019/0000538 A1 | 1/2019 | Widenhouse et al. |
| 2019/0000555 A1 | 1/2019 | Schings et al. |
| 2019/0000565 A1 | 1/2019 | Shelton, IV et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038371 A1 | 2/2019 | Wixey et al. |
| 2019/0046187 A1 | 2/2019 | Yates et al. |
| 2019/0059886 A1 | 2/2019 | Shelton, IV et al. |
| 2019/0090870 A1 | 3/2019 | Shelton, IV et al. |
| 2019/0090871 A1 | 3/2019 | Shelton, IV et al. |
| 2019/0099177 A1 | 4/2019 | Yates et al. |
| 2019/0099178 A1 | 4/2019 | Leimbach et al. |
| 2019/0099179 A1 | 4/2019 | Leimbach et al. |
| 2019/0099180 A1 | 4/2019 | Leimbach et al. |
| 2019/0099181 A1 | 4/2019 | Shelton, IV et al. |
| 2019/0099182 A1 | 4/2019 | Bakos et al. |
| 2019/0099183 A1 | 4/2019 | Leimbach et al. |
| 2019/0099184 A1 | 4/2019 | Setser et al. |
| 2019/0099224 A1 | 4/2019 | Leimbach et al. |
| 2019/0099229 A1 | 4/2019 | Spivey et al. |
| 2019/0102930 A1 | 4/2019 | Leimbach et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0105049 A1 | 4/2019 | Moore et al. |
| 2019/0110791 A1 | 4/2019 | Shelton, IV et al. |
| 2019/0110792 A1 | 4/2019 | Shelton, IV et al. |
| 2019/0110793 A1 | 4/2019 | Parihar et al. |
| 2019/0117216 A1 | 4/2019 | Overmyer et al. |
| 2019/0117217 A1 | 4/2019 | Overmyer et al. |
| 2019/0117222 A1 | 4/2019 | Shelton, IV et al. |
| 2019/0117224 A1 | 4/2019 | Setser et al. |
| 2019/0117225 A1 | 4/2019 | Moore et al. |
| 2019/0125343 A1 | 5/2019 | Wise et al. |
| 2019/0125344 A1 | 5/2019 | DiNardo et al. |
| 2019/0125345 A1 | 5/2019 | Baber et al. |
| 2019/0125365 A1 | 5/2019 | Parfett et al. |
| 2019/0125380 A1 | 5/2019 | Hunter et al. |
| 2019/0125475 A1 | 5/2019 | Wise et al. |
| 2019/0133585 A1 | 5/2019 | Smith et al. |
| 2019/0142421 A1 | 5/2019 | Shelton, IV |

(56) References Cited

U.S. PATENT DOCUMENTS

| | | | |
|---|---|---|---|
| 2019/0183490 A1 | 6/2019 | Shelton, IV et al. |
| 2019/0183491 A1 | 6/2019 | Shelton, IV et al. |
| 2019/0183492 A1 | 6/2019 | Shelton, IV et al. |
| 2019/0183493 A1 | 6/2019 | Shelton, IV et al. |
| 2019/0183494 A1 | 6/2019 | Shelton, IV et al. |
| 2019/0183495 A1 | 6/2019 | Shelton, IV et al. |
| 2019/0183496 A1 | 6/2019 | Shelton, IV et al. |
| 2019/0183497 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183500 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183503 A1 | 6/2019 | Shelton, IV et al. |
| 2019/0183504 A1 | 6/2019 | Shelton, IV et al. |
| 2019/0183505 A1 | 6/2019 | Vendely et al. |
| 2019/0183592 A1 | 6/2019 | Shelton, IV et al. |
| 2019/0183594 A1 | 6/2019 | Shelton, IV et al. |
| 2019/0183597 A1 | 6/2019 | Shelton, IV et al. |
| 2019/0192137 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192145 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200895 A1 | 7/2019 | Shelton, IV et al. |
| 2019/0200991 A1 | 7/2019 | Moore et al. |
| 2019/0200992 A1 | 7/2019 | Moore et al. |
| 2019/0200993 A1 | 7/2019 | Moore et al. |
| 2019/0200994 A1 | 7/2019 | Moore et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0223871 A1 | 7/2019 | Moore et al. |
| 2019/0267403 A1 | 8/2019 | Li et al. |
| 2019/0269403 A1 | 9/2019 | Baxter, III et al. |

FOREIGN PATENT DOCUMENTS

| | | | |
|---|---|---|---|
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 2868212 Y | 2/2007 |
| CN | 200942099 Y | 9/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101522120 A | 9/2009 |
| CN | 101669833 A | 3/2010 |
| CN | 101721236 A | 6/2010 |
| CN | 101828940 A | 9/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 101779977 B | 12/2011 |
| CN | 101912284 B | 7/2012 |
| CN | 202313537 U | 7/2012 |
| CN | 202397539 U | 8/2012 |
| CN | 202426586 U | 9/2012 |
| CN | 202489990 U | 10/2012 |
| CN | 102835977 A | 12/2012 |
| CN | 203564285 U | 4/2014 |
| CN | 203564287 U | 4/2014 |
| CN | 203597997 U | 5/2014 |
| CN | 103829983 A | 6/2014 |
| CN | 103908313 A | 7/2014 |
| CN | 203736251 U | 7/2014 |
| CN | 103981635 A | 8/2014 |
| CN | 203815517 U | 9/2014 |
| CN | 102783741 B | 10/2014 |
| CN | 102973300 B | 10/2014 |
| CN | 104337556 A | 2/2015 |
| CN | 204158441 U | 2/2015 |
| CN | 102469995 B | 3/2015 |
| CN | 204636451 U | 9/2015 |
| CN | 103860225 B | 3/2016 |
| CN | 103750872 B | 5/2016 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004063606 A1 | 7/2006 |
| DE | 202007003114 U1 | 6/2007 |
| DE | 102010013150 A1 | 9/2011 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |

(56) References Cited

FOREIGN PATENT DOCUMENTS

| | | |
|---|---|---|
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2842500 A1 | 3/2015 |
| EP | 2853220 A1 | 4/2015 |
| EP | 2298220 B1 | 6/2016 |
| EP | 2510891 B1 | 6/2016 |
| EP | 3047806 A1 | 7/2016 |
| EP | 2364651 B1 | 11/2016 |
| EP | 2747235 B1 | 11/2016 |
| EP | 2789299 B1 | 5/2017 |
| EP | 3363378 A1 | 8/2018 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S56112235 A | 9/1981 |
| JP | S62170011 U | 10/1987 |
| JP | S63270040 A | 11/1988 |
| JP | H0129503 B2 | 6/1989 |
| JP | H0378514 U | 8/1991 |
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H 05226945 A | 9/1993 |
| JP | H0630945 A | 2/1994 |
| JP | H06237937 A | 8/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H 10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000271141 A | 10/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006346445 A | 12/2006 |
| JP | 2008-220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | 2010069307 A | 4/2010 |
| JP | 2010069310 A | 4/2010 |
| JP | 2010098844 A | 4/2010 |
| JP | 2011072574 A | 4/2011 |
| JP | 4722849 B2 | 7/2011 |
| JP | 2011524199 A | 9/2011 |
| JP | 5154710 B1 | 2/2013 |

(56) References Cited

FOREIGN PATENT DOCUMENTS

| | | |
|---|---|---|
| JP | 2014121599 A | 7/2014 |
| JP | 2016-512057 A | 4/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006/073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-20070137304 A2 | 11/2007 |
| WO | WO-2007142625 A2 | 12/2007 |
| WO | WO-2008021969 A2 | 2/2008 |
| WO | WO-2008/061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012/013577 A1 | 2/2012 |
| WO | WO-2012044606 A2 | 4/2012 |
| WO | WO-2012061725 A1 | 5/2012 |
| WO | WO-2012166503 A1 | 12/2012 |
| WO | WO-2013151888 A1 | 10/2013 |
| WO | WO-2014004209 A2 | 1/2014 |
| WO | WO-2014/113438 A1 | 7/2014 |
| WO | WO-2015/032797 A1 | 3/2015 |
| WO | WO-2015138760 A1 | 9/2015 |
| WO | WO-2015187107 A1 | 12/2015 |

OTHER PUBLICATIONS

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Datasheet for Panasonic TK Relays Ultra Low Profile 2 A Polarized Relay, Copyright Matsushita Electric Works, Ltd. (Known of at least as early as Aug. 17, 2010), 5 pages.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

"Indian Standard: Automotive Vehicles—Brakes and Braking Systems (IS 11852-1:2001)", Mar. 1, 2001.

Van Meer et al., "A Disposable Plastic Compact Wrist for Smart Minimally Invasive Surgical Tools," LAAS/CNRS (Aug. 2005).

(56) References Cited

OTHER PUBLICATIONS

Breedveld et al., "A New, Easily Miniaturized Sterrable Endoscope," IEEE Engineering in Medicine and Biology Magazine (Nov./Dec. 2005).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Pitt et al., "Attachment of Hyaluronan to Metallic Surfaces," J. Biomed. Mater. Res. 68A: pp. 95-106, 2004.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDriveTM Ultra Powered Stapling System, Cleaning and Sterilization Guide," (2 pages).
Covidien Brochure "iDrive™ Ultra Powered Stapling System," (6 pages).
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Disclosed Anonymously, "Motor-Driven Surgical Stapler Improvements," Research Disclosure Database No. 526041, Published: Feb. 2008.
Covidien Brochure, "Endo GIA™ Reloads with Tri-Staple™ Technology," (2010), 1 page.
Covidien Brochure, "Endo GIA™ Reloads with Tri-Staple ™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al, Comparison of the effects of Mg-6Zn and Ti-3AI-2.5V alloys on TGF-β/TNF-α/VEGF/b-FGF in the healing of the intestinal track in vivo, Biomed. Mater. 9 (2014), 11 pages.
Yan et al., "Comparison of the effects of Mg-6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51g); (Year: 2018)
"Foot and Ankle: Core Knowledge in Orthopaedics"; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.

(56) References Cited

OTHER PUBLICATIONS

Honda HS1332AT and ATD Model Info, powerequipment.honda. com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
"Tutorial overview of inductively coupled RFID Systems," UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.
"Pushing Pixels (GIF)", published on dribble.com, 2013.

\* cited by examiner

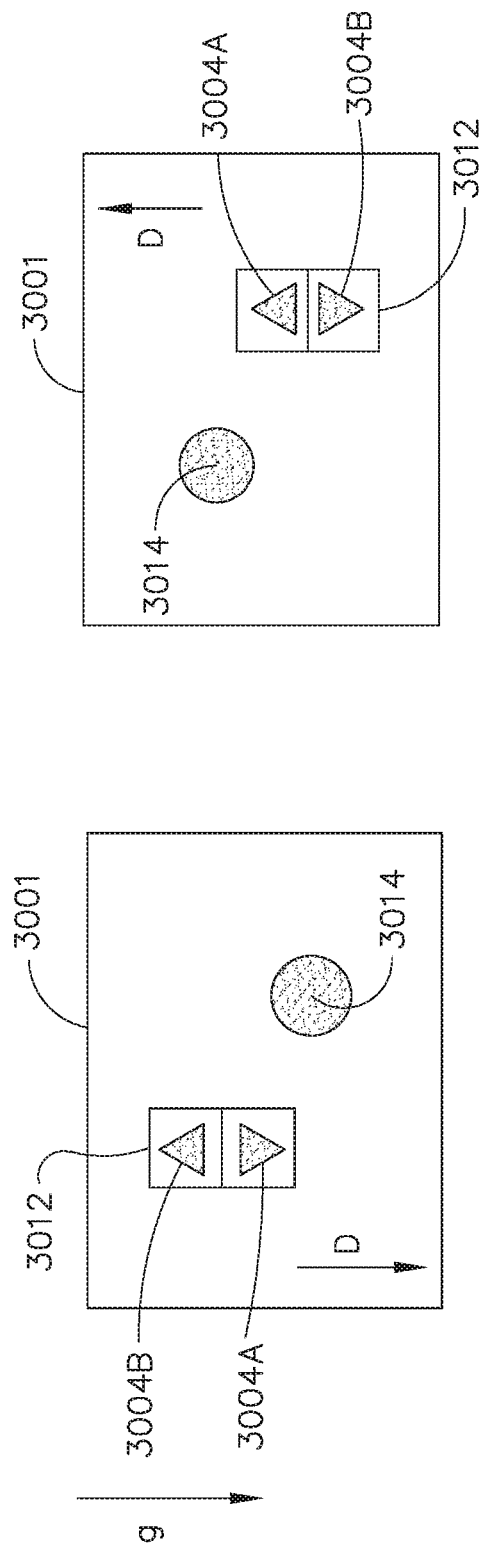
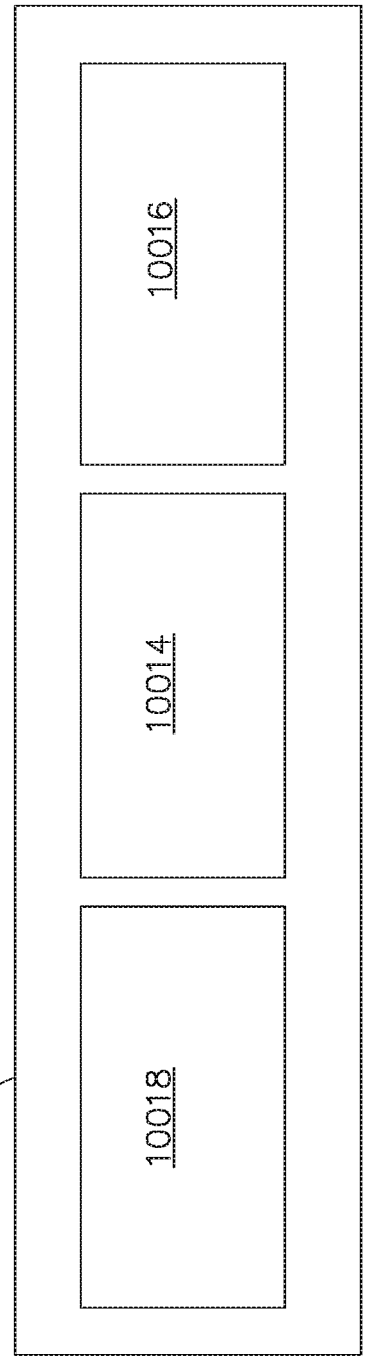
FIG. 14A
FIG. 14B
FIG. 15

SURGICAL INSTRUMENT DISPLAYING SUBSEQUENT STEP OF USE

CROSS-REFERENCE TO RELATED APPLICATIONS

The present application is a continuation application claiming priority under 35 U.S.C. § 120 from U.S. patent application Ser. No. 14/226,126, entitled INTERFACE SYSTEMS FOR USE WITH SURGICAL INSTRUMENTS, filed on Mar. 26, 2014.

BACKGROUND

The present invention relates to surgical instruments and, in various circumstances, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of instances of the invention taken in conjunction with the accompanying drawings, wherein:

FIG. 14A is a side view of the handle assembly of FIG. 10 in an upright position;

FIG. 14B is a side view of the handle assembly of FIG. 10 in an upside down position;

FIG. 15 is a schematic illustration of the display of FIG. 10 showing a plurality of icons;

DETAILED DESCRIPTION

Figure 1:
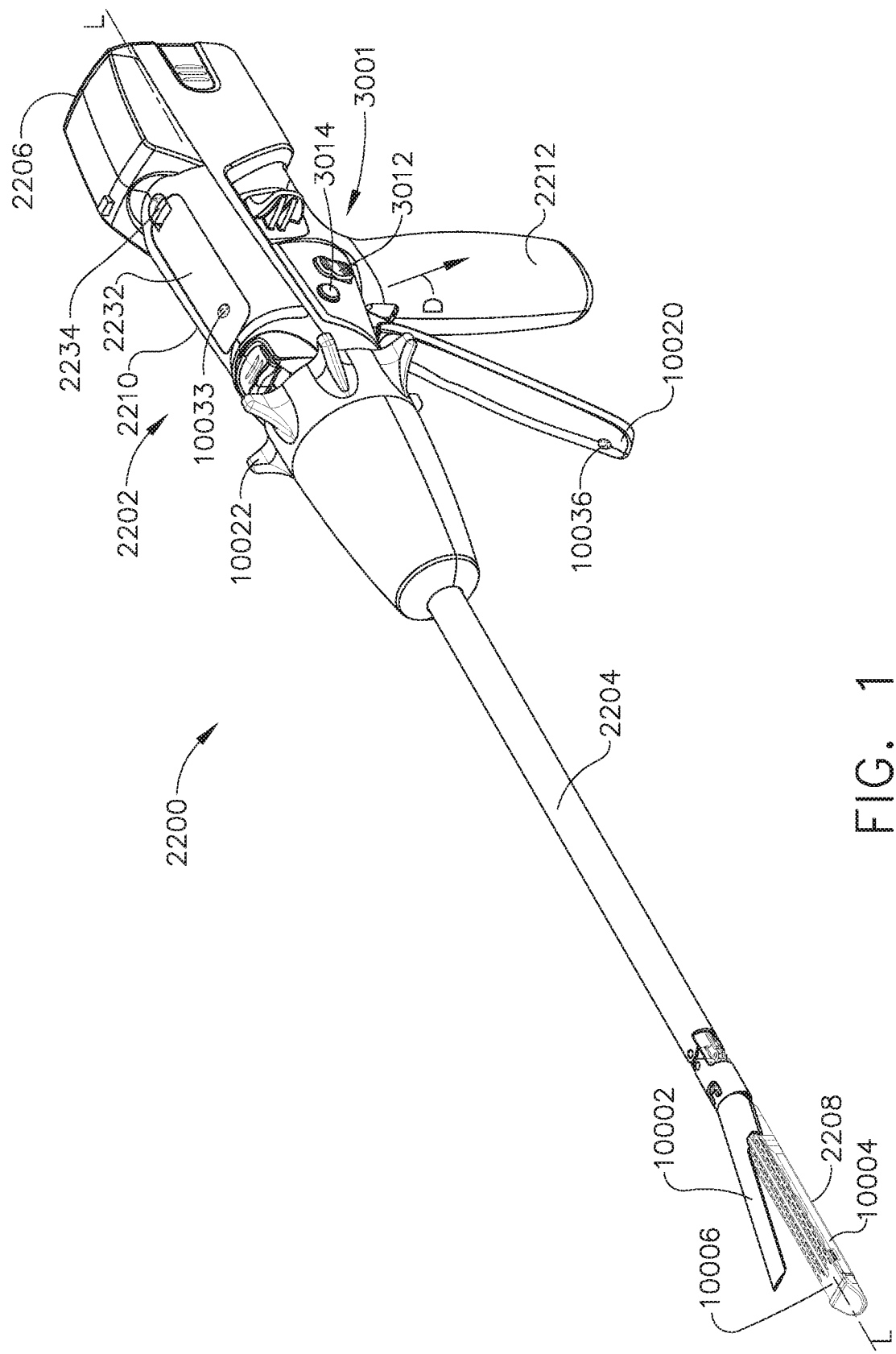
FIG. 1 is a perspective view of a surgical instrument comprising a handle assembly and a shaft assembly including an end effector.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION;

U.S. patent application Ser. No. 13/782,323, entitled ROTARY POWERED ARTICULATION JOINTS FOR SURGICAL INSTRUMENTS;

U.S. patent application Ser. No. 13/782,338, entitled THUMBWHEEL SWITCH ARRANGEMENTS FOR SURGICAL INSTRUMENTS;

U.S. patent application Ser. No. 13/782,499, entitled ELECTROMECHANICAL SURGICAL DEVICE WITH SIGNAL RELAY ARRANGEMENT;

U.S. patent application Ser. No. 13/782,460, entitled MULTIPLE PROCESSOR MOTOR CONTROL FOR MODULAR SURGICAL INSTRUMENTS;

U.S. patent application Ser. No. 13/782,358, entitled JOYSTICK SWITCH ASSEMBLIES FOR SURGICAL INSTRUMENTS;

U.S. patent application Ser. No. 13/782,481, entitled SENSOR STRAIGHTENED END EFFECTOR DURING REMOVAL THROUGH TROCAR;

U.S. patent application Ser. No. 13/782,518, entitled CONTROL METHODS FOR SURGICAL INSTRUMENTS WITH REMOVABLE IMPLEMENT PORTIONS;

U.S. patent application Ser. No. 13/782,375, entitled ROTARY POWERED SURGICAL INSTRUMENTS WITH MULTIPLE DEGREES OF FREEDOM; and U.S. patent application Ser. No. 13/782,536, entitled SURGICAL INSTRUMENT SOFT STOP are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE;

U.S. patent application Ser. No. 13/803,193, entitled CONTROL ARRANGEMENTS FOR A DRIVE MEMBER OF A SURGICAL INSTRUMENT;

U.S. patent application Ser. No. 13/803,053, entitled INTERCHANGEABLE SHAFT ASSEMBLIES FOR USE WITH A SURGICAL INSTRUMENT;

U.S. patent application Ser. No. 13/803,086, entitled ARTICULATABLE SURGICAL INSTRUMENT COMPRISING AN ARTICULATION LOCK;

U.S. patent application Ser. No. 13/803,210, entitled SENSOR ARRANGEMENTS FOR ABSOLUTE POSITIONING SYSTEM FOR SURGICAL INSTRUMENTS;

U.S. patent application Ser. No. 13/803,148, entitled MULTI-FUNCTION MOTOR FOR A SURGICAL INSTRUMENT;

U.S. patent application Ser. No. 13/803,066, entitled DRIVE SYSTEM LOCKOUT ARRANGEMENTS FOR MODULAR SURGICAL INSTRUMENTS;

U.S. patent application Ser. No. 13/803,117, entitled ARTICULATION CONTROL SYSTEM FOR ARTICULATABLE SURGICAL INSTRUMENTS;

U.S. patent application Ser. No. 13/803,130, entitled DRIVE TRAIN CONTROL ARRANGEMENTS FOR MODULAR SURGICAL INSTRUMENTS; and U.S. patent application Ser. No. 13/803,159, entitled METHOD AND SYSTEM FOR OPERATING A SURGICAL INSTRUMENT.

Applicant of the present application also owns the following patent applications that were filed on Mar. 26, 2014 and are each herein incorporated by reference in their respective entireties:

U.S. patent application Ser. No. 14/226,142, entitled SURGICAL INSTRUMENT COMPRISING A SENSOR SYSTEM, now U.S. Pat. No. 9,913,642;

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIG. 1 generally depicts a motor-driven surgical instrument 2200. In certain circumstances, the surgical instrument 2200 may include a handle assembly 2202, a shaft assembly 2204, and a power assembly 2206 (or "power source" or "power pack"). The shaft assembly 2204 may include an end effector 2208 which, in certain circumstances, can be configured to act as an endocutter for clamping, severing, and/or stapling tissue, although, in other circumstances, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008. The entire disclosures of U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, are incorporated herein by reference in their entirety.

Referring again to FIG. 1, the handle assembly 2202 may comprise a housing 2210 that includes a handle 2212 that may be configured to be grasped, manipulated, and/or actuated by a clinician. However, it will be understood that the various unique and novel arrangements of the housing 2210 may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the shaft assembly 2204 disclosed herein and its respective equivalents. For example, the housing 2210 disclosed herein may be employed with various robotic systems, instruments, components, and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719. The disclosure of U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, is incorporated by reference herein in its entirety.

In certain instances, the surgical instrument 2200 may include several operable systems that extend, at least partially, through the shaft 2204 and are in operable engagement with the end effector 2208. For example, the surgical instrument 2200 may include a closure assembly that may transition the end effector 2208 between an open configuration and a closed configuration, an articulation assembly that may articulate the end effector 2208 relative to the shaft 2204, and/or a firing assembly that may fasten and/or cut tissue captured by the end effector 2208. In addition, the housing 2210 may be separably couplable to the shaft 2204 and may include complimenting closure, articulation, and/or firing drive systems for operating the closure, articulation, and firing assemblies, respectively.

In use, an operator of the surgical instrument 2200 may desire to reset the surgical instrument 2200 and return one or more of the assemblies of the surgical instrument 2200 to a default position. For example, the operator may insert the end effector 2208 into a surgical site within a patient through an access port and may then articulate and/or close the end effector 2208 to capture tissue within the cavity. The operator may then choose to undo some or all of the previous actions and may choose to remove the surgical instrument 2200 from the cavity, for instance. The surgical instrument 2200 may include one more systems configured to facilitate a reliable return of one or more of the assemblies described above to a home state with minimal input from the operator thereby allowing the operator to remove the surgical instrument from the cavity.

Figure 3:
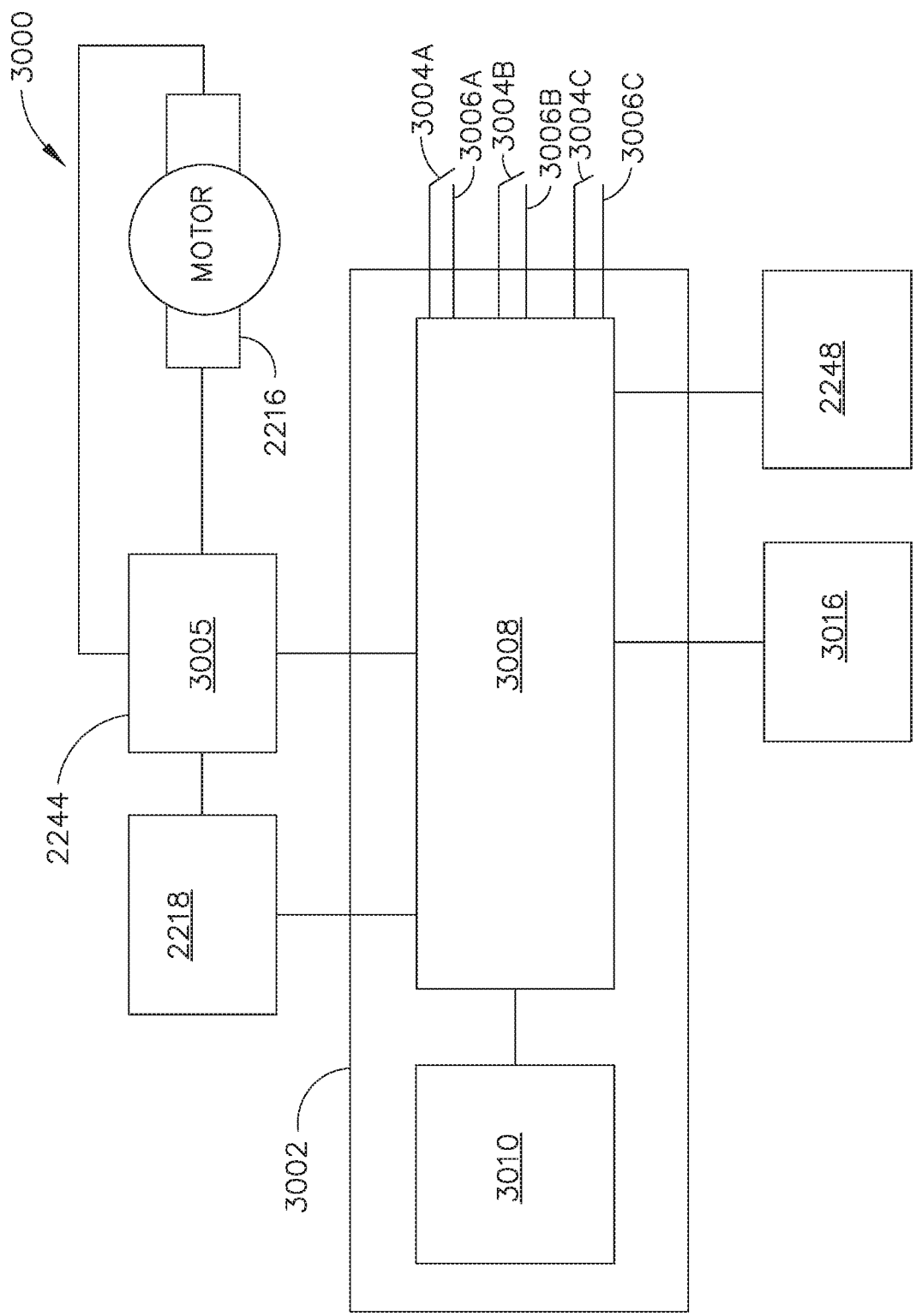
FIG. 3 is a schematic block diagram of a control system of the surgical instrument of FIG. 1.

Referring to FIGS. 1 and 3, the surgical instrument 2200 may include a control system 3000. A surgical operator may utilize the control system 3000 to articulate the end effector 2208 relative to the shaft 2204 between an articulation home state position and an articulated position, for example. In certain instances, the surgical operator may utilize the control system 3000 to reset or return the articulated end effector 2208 to the articulation home state position. The control system 3000 can be positioned, at least partially, in the housing 2210. In certain instances, as illustrated in FIG. 3, the control system 3000 may comprise a microcontroller 3002 ("controller") which can be configured to receive an input signal and, in response, activate a motor 2216 to cause the end effector 2208 to articulate in accordance with such an input signal, for example.

Further to the above, the end effector 2208 can be positioned in sufficient alignment with the shaft 2204 in the articulation home state position, also referred to herein as an unarticulated position such that the end effector 2208 and at least a portion of shaft 2204 can be inserted into or retracted from a patient's internal cavity through an access port such as, for example, a trocar positioned in a wall of the internal cavity without damaging the access port. In certain instances, the end effector 2208 can be aligned, or at least substantially aligned, with a longitudinal axis "LL" passing through the shaft 2204 when the end effector 2208 is in the articulation home state position, as illustrated in FIG. 1. In at least one instance, the articulation home state position can be at any angle up to and including 5°, for example, with the longitudinal axis "LL" on either side of the longitudinal axis "LL". In another instance, the articulation home state position can be at any angle up to and including 3°, for example, with the longitudinal axis "LL" on either side of the longitudinal axis "LL". In yet another instance, the articulation home state position can be at any angle up to and including 7°, for example, with the longitudinal axis "LL" on either side of the longitudinal axis "LL".

The control system 3000 can be operated to articulate the end effector 2208 relative to the shaft 2204 in a plane extending along the longitudinal axis "LL" in a first direction such as, for example, a clockwise direction and/or a second direction such as, for example, a counterclockwise direction. In at least one instance, the control system 3000 can be operated to articulate the end effector 2208 in the clockwise direction form the articulation home state position to an articulated position 10 degrees to the right of the longitudinal axis "LL", for example. In another example, the control system 3000 can be operated to articulate the end effector 2208 in the counterclockwise direction form the articulated position at 10 degrees to the right of the longitudinal axis "LL" to the articulation home state position. In yet another example, the control system 3000 can be operated to articulate the end effector 2208 relative to the shaft 2204 in the counterclockwise direction from the articulation home state position to an articulated position 10 degrees to the left of the longitudinal axis "LL", for example. The reader will appreciate that the end effector can be articulated to different angles in the clockwise direction and/or the counterclockwise direction.

Figure 2:
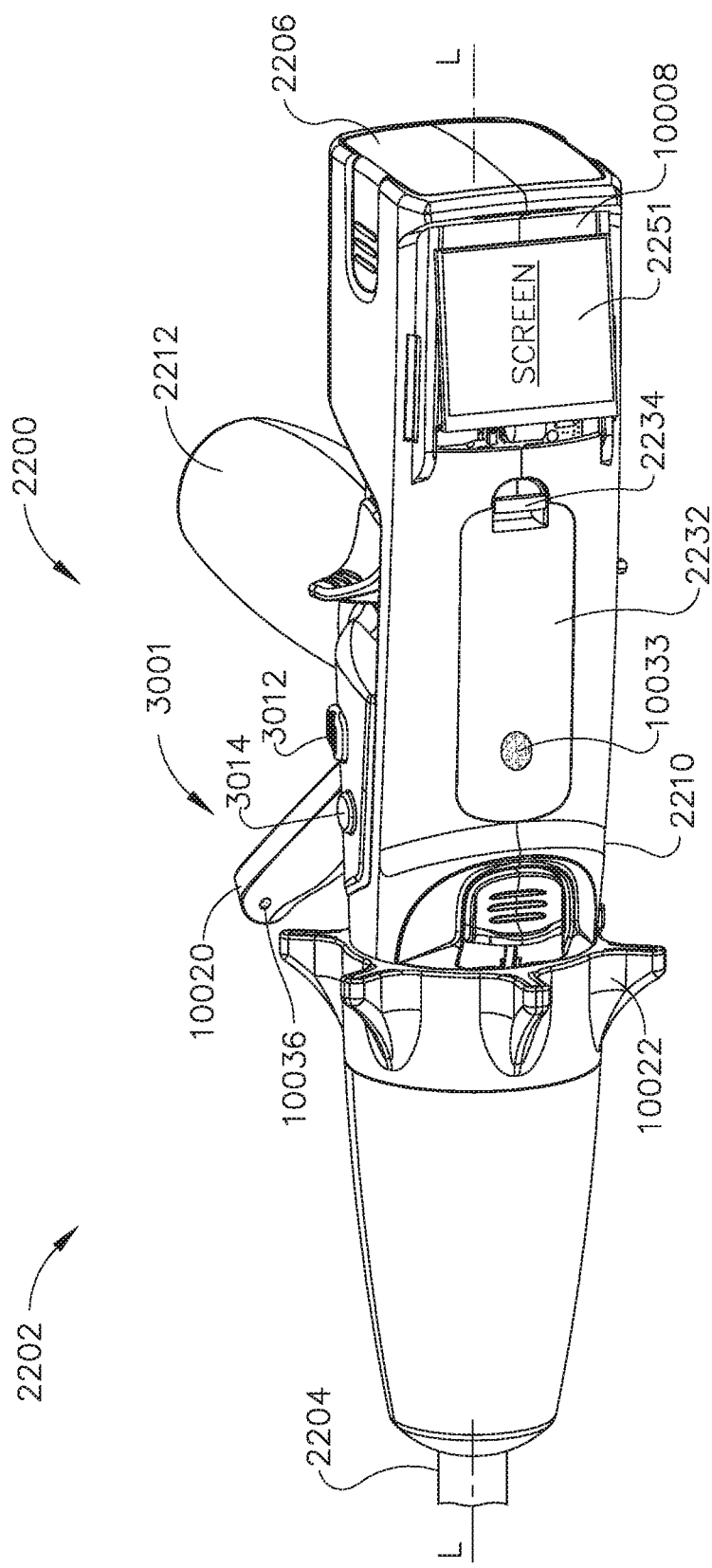
FIG. 2 is a perspective view of the handle assembly of the surgical instrument of FIG. 1.

Referring to FIGS. 1 and 2, the housing 2210 of the surgical instrument 2200 may comprise an interface 3001 which may include a plurality of controls that can be utilized by the operator to operate the surgical instrument 2200. In certain instances, the interface 3001 may comprise a plurality of switches which can be coupled to the controller 3002 via electrical circuits, for example. In certain instances, as illustrated in FIG. 3, the interface 3001 comprises three switches 3004A-C, wherein each of the switches 3004A-C is coupled to the controller 3002 via electrical circuits such as, for example electrical circuits 3006A-C, respectively. The reader will appreciate that other combinations of switches and circuits can be utilized with the interface 3001.

Referring to FIG. 3, the controller 3002 may generally comprise a microprocessor 3008 ("processor") and one or more memory units 3010 operationally coupled to the processor 3008. By executing instruction code stored in the memory 3010, the processor 3008 may control various components of the surgical instrument 2200, such as the motor 2216, various drive systems, and/or a user display, for example. The controller 3002 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 3002 may include a hybrid circuit comprising discrete and integrated circuit elements or components on one or more substrates, for example.

In certain instances, the microcontroller 3002 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

In various forms, the motor 2216 may be a DC brushed driving motor having a maximum rotation of, approximately, 25,000 RPM, for example. In other arrangements, the motor 2216 may include a brushless motor, a cordless motor, a synchronous motor, a stepper motor, or any other suitable electric motor. A battery 2218 (or "power source" or "power pack"), such as a Li ion battery, for example, may be coupled to the housing 2212 to supply power to the motor 2216, for example.

Referring again to FIG. 3, the surgical instrument 2200 may include a motor controller 3005 in operable communication with the controller 3002. The motor controller 3005 can be configured to control a direction of rotation of the motor 2216. In certain instances, the motor controller 3005 may be configured to determine the voltage polarity applied to the motor 2216 by the battery 2218 and, in turn, determine the direction of rotation of the motor 2216 based on input from the controller 3002. For example, the motor 2216 may reverse the direction of its rotation from a clockwise direction to a counterclockwise direction when the voltage polarity applied to the motor 2216 by the battery 2218 is reversed by the motor controller 3005 based on input from the controller 3002. In addition, the motor 2216 can be operably coupled to an articulation drive which can be driven by the motor 2216 distally or proximally depending on the direction in which the motor 2216 rotates, for example. Furthermore, the articulation drive can be operably coupled to the end effector 2208 such that, for example, the axial translation of the articulation drive proximally may cause the end effector 2208 to be articulated in the counterclockwise direction, for example, and/or the axial translation of the articulation drive distally may cause the end effector 2208 to be articulated in the clockwise direction, for example.

Figure 7:
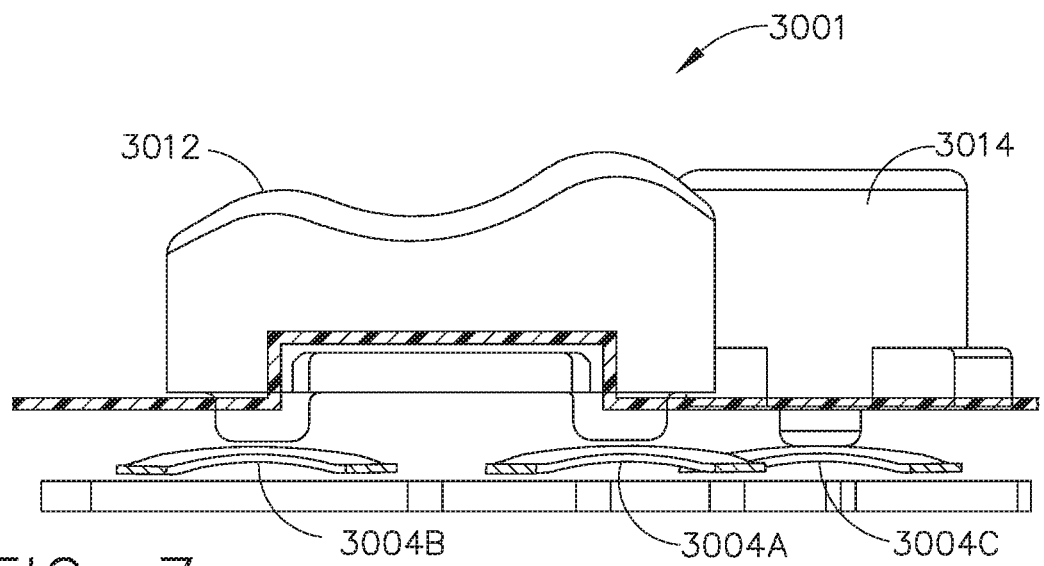
FIG. 7 is a schematic illustration of an interface of the surgical instrument of FIG. 1 in an inactive or neutral configuration.

In various instances, referring to FIGS. 1-3, the interface 3001 can be configured such that the switch 3004A can be dedicated to the clockwise articulation of the end effector 2208, for example, and the switch 3004B can be dedicated to the counterclockwise articulation of the end effector 2208, for example. In such instances, the operator may articulate the end effector 2208 in the clockwise direction by closing the switch 3004A and may articulate the end effector 2208 in the counterclockwise direction by closing the switch 3004B. In various instances, the switches 3004A-C can comprise open-biased dome switches, as illustrated in FIG. 7. Other types of switches can also be employed such as, for example, capacitive switches.

Figure 8:
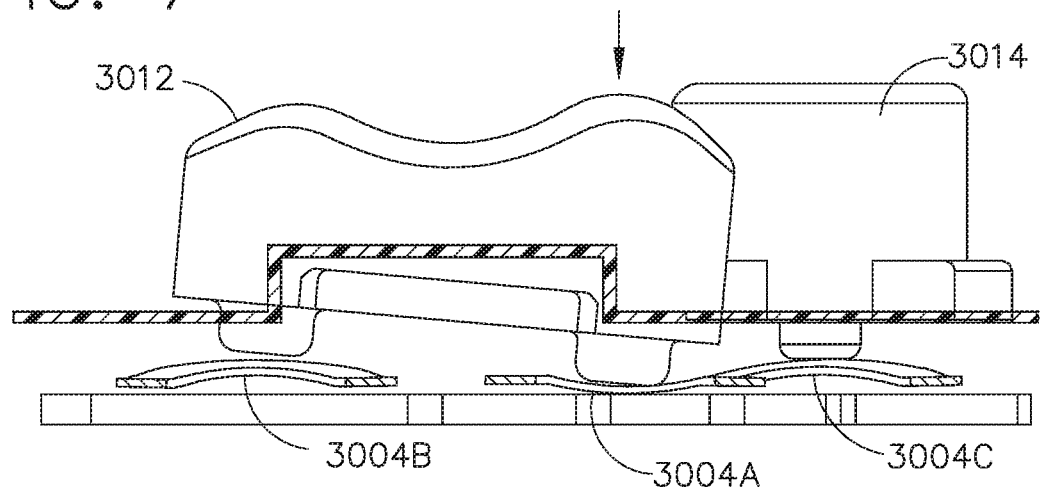
FIG. 8 is a schematic illustration of the interface of FIG. 7 activated to articulate an end effector.

Referring to FIG. 7, the dome switches 3004A and 3004B can be controlled by a rocker 3012. Other means for controlling the switches 3004A and 3004B are contemplated by the present disclosure. In the neutral position, as illustrated in FIG. 7, both of the switches 3004A and 3004B are biased in the open position. The operator, for example, may articulate the end effector 2208 in the clockwise direction by tilting the rocker forward thereby depressing the dome switch 3004A, as illustrated in FIG. 8. In result, the circuit 3006A (FIG. 3) may be closed signaling the controller 3002 to activate the motor 2216 to articulate the end effector 2208 in the clockwise direction, as described above. The motor 2216 may continue to articulate the end effector 2208 until the operator releases the rocker 3012 thereby allowing the dome switch 3004A to return to the open position and the rocker 3012 to the neutral position. In some circumstances, the controller 3002 may be able to identify when the end effector 2208 has reached a predetermined maximum degree of articulation and, at such point, interrupt power to the motor 2216 regardless of whether the dome switch 3004A is being depressed. In a way, the controller 3002 can be configured to override the operator's input and stop the motor 2216 when a maximum degree of safe articulation is reached. Alternatively, the operator may articulate the end effector 2208 in the counterclockwise direction by tilting the rocker 3012 back thereby depressing the dome switch 3004B, for example. In result, the circuit 3006B may be closed signaling the controller 3002 to activate the motor 2216 to articulate the end effector 2208 in the counterclockwise direction, as described above. The motor 2216 may continue to articulate the end effector 2208 until the operator releases the rocker 3012 thereby allowing the dome switch 3004B to return to the open position and the rocker 3012 to the neutral position. In some circumstances, the controller 3002 may be able to identify when the end effector 2208 has reached a predetermined maximum degree of articulation and, at such point, interrupt power to the motor 2216 regardless of whether the dome switch 3004B is being depressed. In a way, the controller 3002 can be configured to override the operator's input and stop the motor 2216 when a maximum degree of safe articulation is reached.

As described above in greater detail, an operator may desire to return the end effector 2208 to the articulation home state position to align, or at least substantially align, the end effector 2208 with the shaft 2204 in order to retract the surgical instrument 2200 from a patient's internal cavity, for example. In various instances, the control system 3000 may include a virtual detent that may alert the operator when the end effector 2208 has reached the articulation home state position. In certain instances, the control system 3000 may be configured to stop the articulation of the end effector 2208 upon reaching the articulation home state position, for example. In certain instances, the control system 3000 may be configured to provide feedback to the operator when the end effector 2208 reaches the articulation home state position, for example.

Figure 4:
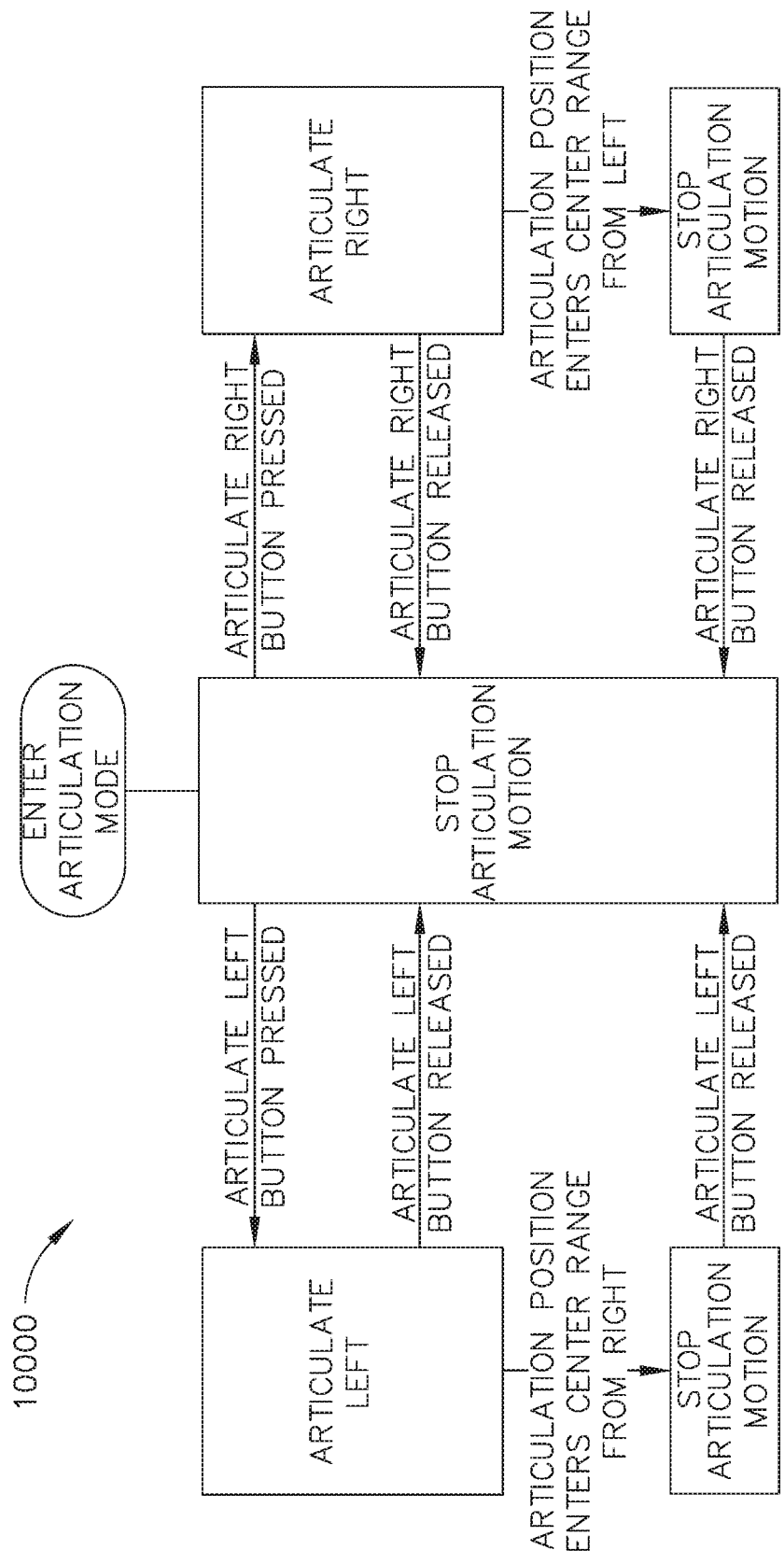
FIG. 4 is a schematic block diagram of a module for use with the surgical instrument of FIG. 1.

In certain instances, the control system 3000 may comprise various executable modules such as software, programs, data, drivers, and/or application program interfaces (APIs), for example. FIG. 4 depicts an exemplary virtual detent module 10000 that can be stored in the memory 3010, for example. The module 10000 may include program instructions, which when executed may cause the processor 3008, for example, to alert the operator of the surgical instrument 2200 when the end effector 2208 reaches the articulation home state position during the articulation of the end effector 2208 from an articulated position, for example.

As described above, referring primarily to FIGS. 3, 7, and 8, the operator may use the rocker 3012 to articulate the end effector 2208, for example. In certain instances, the operator may depress the dome switch 3004A of the rocker 3012 to articulate the end effector 2208 in a first direction such as a clockwise direction to the right, for example, and may depress the dome switch 3004B to articulate the end effector 2208 in a second direction such as a counterclockwise direction to the left, for example. In various instances, as illustrated in FIG. 4, the module 10000 may modulate the response of the processor 3008 to input signals from the dome switches 3004A and/or 3004B. For example, the processor 3008 can be configured to activate the motor 2216 to articulate the end effector 2208 to the right, for example, while the dome switch 3004A is depressed; and the processor 3008 can be configured to activate the motor 2216 to articulate the end effector 2208 to the left, for example, while the dome switch 3004B is depressed. In addition, the processor 3008 may be configured to stop the articulation of the end effector 2208 by causing the motor 2216 to stop, for example, when input signals from the dome switches 3004A and/or 3004B are stopped such as when the operator releases the dome switches 3004A and/or 3004B, respectively.

In various instances, as described above, the articulation home state position may comprise a range of positions. In certain instances, the processor 3008 can be configured to detect when the end effector 2208 enters the range of positions defining the articulation home state position. In certain instances, the surgical instrument 2200 may comprise one or more positioning systems (not shown) for sensing and recording the articulation position of the end effector 2208. The processor 3008 can be configured to employ the one or more positioning systems to detect when the end effector 2208 enters the articulation home state position.

As illustrated in FIG. 4, in certain instances, upon reaching the articulation home state position, the processor 3008 may stop the articulation of the end effector 2208 to alert the operator that the articulation home state position is reached; the processor 3008, in certain instances, may stop the articulation in the articulation home state position even if the operator continues to depress the rocker 3012. In certain instances, in order to continue past the articulation home state position, the operator may release the rocker 3012 and then tilt it again to restart the articulation. In at least one such instance, the operator may push the rocker 3012 to depress dome switch 3004A, for example, to rotate the end effector 2208 toward its home state position until the end effector 2208 reaches its home state position and the processor 3008 stops the articulation of the end effector 2208, wherein the operator can then release the rocker 3012 and, then, push the rocker 3012 to depress the dome switch 3004A once again in order to continue the articulation of the end effector 2208 in the same direction.

Figure 5:
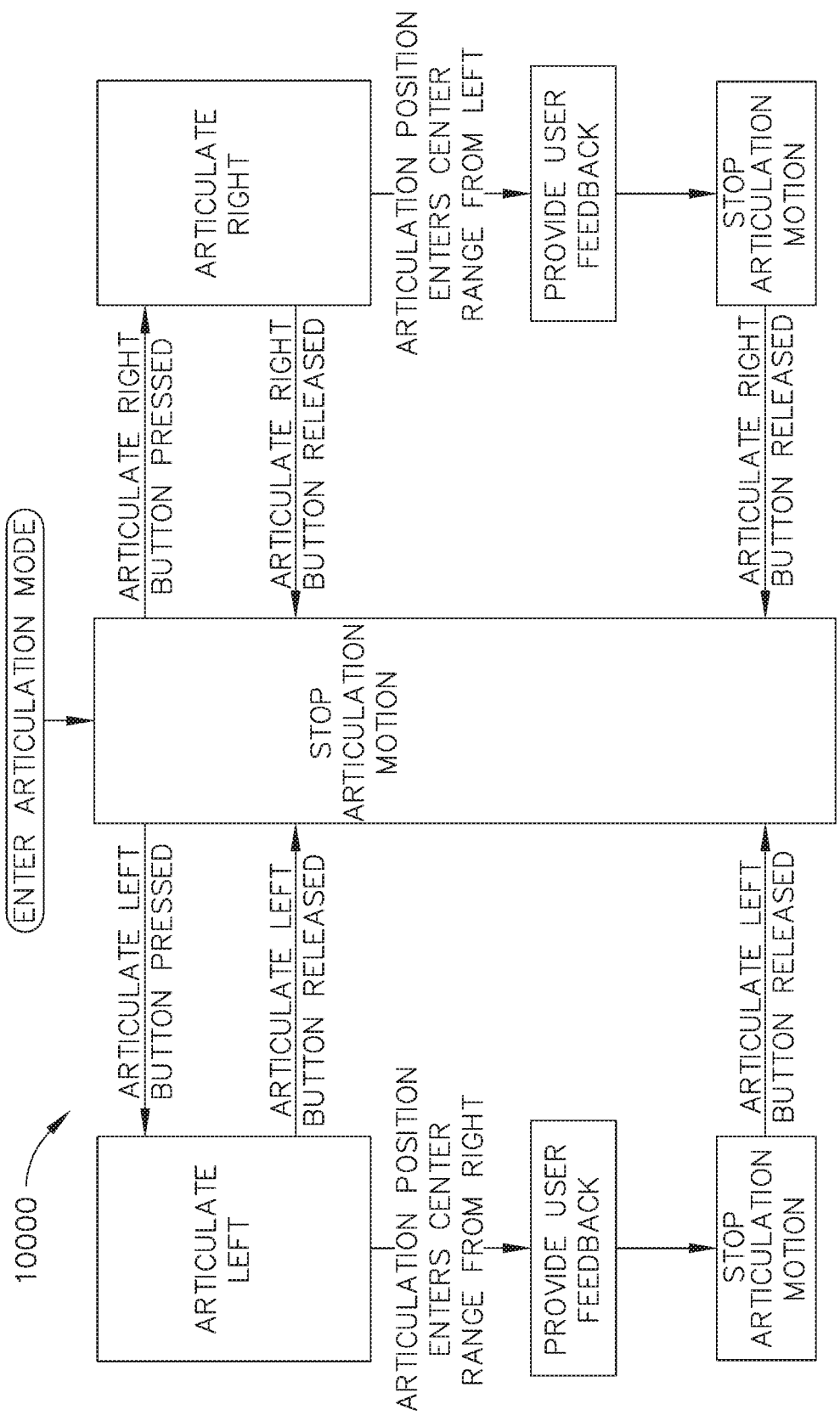
FIG. 5 is a schematic block diagram of a module for use with the surgical instrument of FIG. 1.

In certain instances, as illustrated in FIG. 5, the module 10000 may comprise a feedback mechanism to alert the operator when the articulation home state position is reached. Various feedback devices 2248 (FIG. 3) can be employed by the processor 3008 to provide sensory feedback to the operator. In certain instances, the devices 2248 may comprise, for example, visual feedback devices such as display screens and/or LED indicators, for example. In certain instances, the devices 2248 may comprise audio feedback devices such as speakers and/or buzzers, for example. In certain instances, the devices 2248 may comprise tactile feedback devices such as a mechanical detent, for example, which can provide haptic feedback, for example. In some instances, haptic feedback can be provided by a vibrating motor, for example, that can provide a pulse of vibrations to the handle of the surgical instrument, for example. In certain instances, the devices 2248 may comprise combinations of visual feedback devices, audio feedback devices, and/or tactile feedback devices, for example.

In certain instances, the processor 3008 can be configured to stop the articulation of the end effector 2208 and provide feedback to the operator when the articulation home state position is reached, for example. In certain instances, the processor 3008 may provide feedback to the operator but may not stop the articulation of the end effector 2208 when the articulation home state position is reached. In at least one instance, the end effector 2208 can be moved from a position on a first side of the home state position toward the home state position, pass through the home state position, and continue moving in the same direction on the other side of the home state position. During such movement, the operator may be supplied with some form of feedback at the moment the end effector 2208 passes through the home state position. In certain instances, the processor 3008 may stop the articulation of the end effector 2208 but may not provide feedback to the operator when the articulation home state position is reached, for example. In certain instances, the processor 3008 may pause the end effector 2208 as it passes through its center position and then continue past its center position. In at least one instance, the end effector 2208 can temporarily dwell in its center position for about 2 seconds, for example, and then continue its articulation so long as the articulation switch 3012 remains depressed.

In various instances, an operator of the surgical instrument 2200 may attempt to articulate the end effector 2208 back to its unarticulated position utilizing the rocker switch 3012. As the reader will appreciate, the operator may not be able to accurately and/or repeatably align the end effector 2208 with the longitudinal axis of the surgical instrument shaft. In various instances, though, the operator can readily position the end effector 2208 within a certain range of the center position. For instance, an operator may push the rocker switch 3012 to rotate the end effector 2208 toward its center position and then release the rocker switch 3012 when the operator believes that the end effector 2208 has reached its center position or is close to its center position. The processor 3008 can interpret such circumstances as an attempt to recenter the end effector 2208 and, in the event that the end effector 2208 is not in its center position, the processor 3008 can automatically center the end effector 2208. In at least one example, if the operator of the surgical instrument releases the rocker switch 3012 when the end effector 2208 is within about 10 degrees on either side of the center position, for example, the processor 3008 may automatically recenter the end effector 2208.

Figure 6:
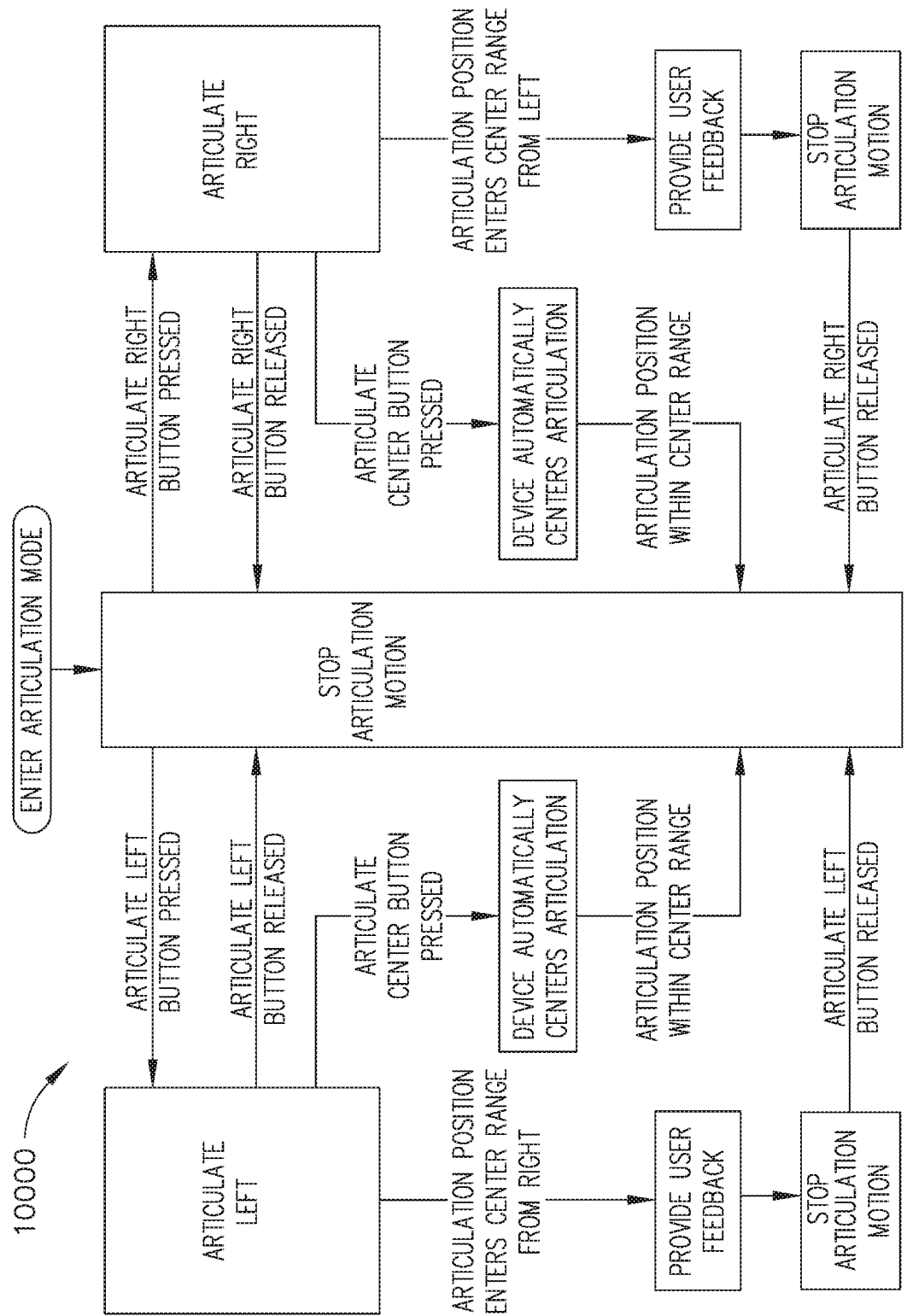
FIG. 6 is a schematic block diagram of a module for use with the surgical instrument of FIG. 1.
Figure 9:
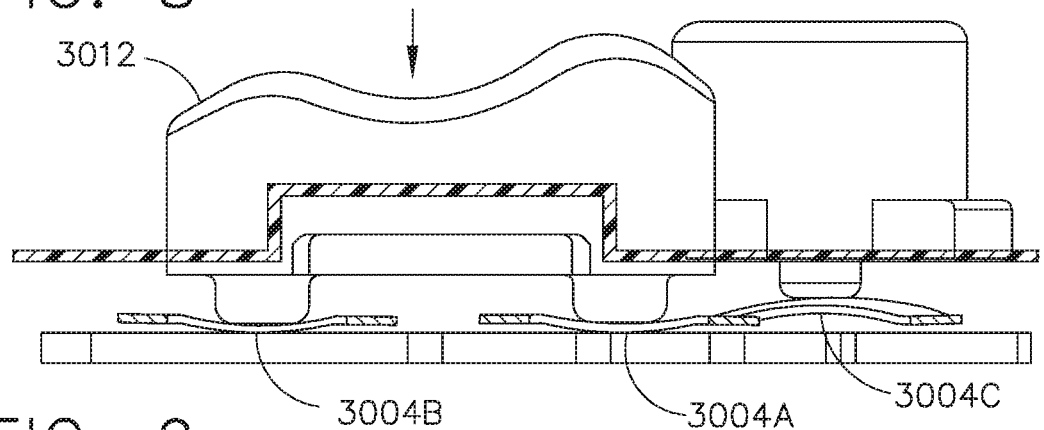
FIG. 9 is a schematic illustration of the interface of FIG. 7 activated to return the end effector to an articulation home state position.

In various instances, referring primarily to FIGS. 3, 6, and 9, the module 10000 may comprise an articulation resetting or centering mechanism. In certain instances, the control system 3000 may include a reset input which may reset or return the end effector 2208 to the articulation home state position if the end effector 2208 is in an articulated position. For example, upon receiving a reset input signal, the processor 3008 may determine the articulation position of the end effector 2208 and, if the end effector 2208 is in the articulation home state position, the processor 3008 may take no action to change the articulation position of the end effector 2208. However, if the end effector 2208 is in an articulated position when the processor 3008 receives a reset input signal, the processor 3008 may activate the motor 2216 to return the end effector 2208 to the articulation home state position. As illustrated in FIG. 9, the operator may depress the rocker 3012 downward to close the dome switches 3004A and 3004B simultaneously, or at least within a short time period from each other, which may transmit the reset input signal to the processor 3008 to reset or return the end effector 2208 to the articulation home state position. The operator may then release the rocker 3012 to allow the rocker 3012 to return to the neutral position and the switches 3004A and 3004B to the open positions. Alternatively, the interface 3001 of the control system 3000 may include a separate reset switch such as, for example, another dome switch which can be independently closed by the operator to transmit the articulation reset input signal to the processor 3008.

Referring again to FIG. 1, the end effector 2208 of the surgical instrument 2200 may include a first jaw comprising an anvil 10002 and a second jaw comprising a channel 10004 configured to receive a staple cartridge 10006 which may include a plurality of staples. In certain instances, the end effector 2208 can be transitioned between an open configuration and a closed configuration to capture tissue between the anvil 10002 and the staple cartridge 10006, for example. Furthermore, the surgical instrument 2200 may include a firing member which can be moved axially between a firing home state position and a fired position to deploy the staples from the staple cartridge 10006 and/or cut the tissue captured between the anvil 10002 and the staple cartridge 10006 when the end effector 2208 is in the closed configuration.

As discussed above, the end effector 2208 can be transitioned between an open configuration and a closed configuration to clamp tissue therein. In at least one embodiment, the anvil 10002 can be moved between an open position and a closed position to compress tissue against the staple cartridge 10006. In various instances, the pressure or force that the anvil 10002 can apply to the tissue may depend on the thickness of the tissue. For a given gap distance between the anvil 10002 and the staple cartridge 10006, the anvil 10002 may apply a larger compressive pressure or force to thicker tissue than thinner tissue. The surgical instrument can include a sensor, such as a load cell, for example, which can detect the pressure or force being applied to the tissue. In certain instances, the thickness and/or composition of the tissue may change while pressure or force is being applied thereto. For instance, fluid, such as blood, for example, contained within the compressed tissue may flow outwardly into the adjacent tissue. In such circumstances, the tissue may become thinner and/or the compressive pressure or force applied to the tissue may be reduced. The sensor configured to detect the pressure of force being applied to the tissue may detect this change. The sensor can be in signal communication with the processor 3008 wherein the processor 3008 can monitor the pressure or force being applied to the tissue and/or the change in the pressure of force being applied to the tissue. In at least one instance, the processor 3008 can evaluate the change in the pressure or force and communicate to the operator of the surgical instrument when the pressure or force has reached a steady state condition and is no longer changing. The processor 3008 can also determine when the change in the pressure or force is at and/or below a threshold value, or rate. For instance, when the change in the pressure or force is above about 10 percent per second, the processor 3008 can illuminate a caution indicator associated with the firing actuator, for example, and when the change in the pressure or force is at or below about 10 percent per second, the processor can illuminate a ready-to-fire indicator associated with the firing actuator, for example. In some circumstances, the surgical instrument may prohibit the firing member from being advanced distally through the end effector 2208 until the change in pressure or force is at and/or below the threshold rate, for example.

In certain instances, the operator of the surgical instrument may elect to deploy only some of the staples stored within the end effector 2208. After the firing member has been sufficiently advanced, in such circumstances, the firing member can be retracted. In various other instances, the operator of the surgical instrument may elect to deploy all of the staples stored within the end effector 2208. In either event, the operator of the surgical instrument can depress a firing actuator extending from the handle assembly 2210 to actuate the motor 2216 and advance the firing member distally. The motor 2216 can be actuated once the firing actuator has been sufficiently depressed. In at least one mode of operation, further depression of the firing actuator may not affect the operation of the motor 2216. The motor 2216 may be operated in the manner dictated by the processor 3008 until the firing actuator is released. In at least one other mode of operation, the degree or amount in which the firing actuator is depressed may affect the manner in which the motor 2216 is operated. For instance, an initial depression of the firing actuator can be detected by the processor 3008 and, in response thereto, the processor 3008 can operate the motor 2216 at a first speed, wherein additional depression of the firing actuator can be detected by the processor 3008 and, in response thereto, the processor 3008 can operate the motor 2216 at a second speed, such as a faster speed, for example. In certain instances, the change in the depression of the firing actuator can be proportional to the change in the motor speed. In at least one instance, the change in the depression of the firing actuator can be linearly proportional to the change in the motor speed. In various circumstances, the further the firing actuator is pulled, the faster the motor 2216 is operated. In certain embodiments, the amount of pressure or force applied to the firing actuator may affect the manner in which the motor 2216 is operated. For instance, an initial pressure or force applied to the firing actuator can be detected by the processor 3008 and, in response thereto, the processor 3008 can operate the motor 2216 at a first speed, wherein additional pressure or force applied to the firing actuator can be detected by the processor 3008 and, in response thereto, the processor 3008 can operate the motor 2216 at a second speed, such as a faster speed, for example. In certain instances, the change in the pressure or force applied to the firing actuator can be proportional to the change in the motor speed. In at least one instance, the change in the pressure or force applied to the firing actuator can be linearly proportional to the change in the motor speed. The disclosure of U.S. Pat. No. 7,845,537, entitled SURGICAL INSTRUMENT HAVING RECORDING CAPABILITIES, which issued on Dec. 7, 2010, is incorporated by reference in its entirety.

As discussed above, the operator of the surgical instrument may elect to deploy all of the staples stored within the end effector 2208. In such circumstances, the operator may depress the firing actuator and then release the actuator when they believe that all of the staples have been deployed during a firing stroke of the firing member. In some instances, the surgical instrument can include an indicator which can be illuminated by the processor 3008 when the firing stroke has been completed. A suitable indicator can comprise a light emitting diode (LED), for example. In certain instances, the operator may believe that a firing stroke has been fully completed even though it may have only been nearly completed. The surgical instrument can comprise at least one sensor configured to detect the position of the firing member within its firing stroke wherein the sensor can be in signal communication with the processor 3008. In the event that the firing stroke is ended at a nearly completed position, the processor 3008 can command the motor 2216 to finish the firing stroke of the firing member. For instance, if the firing member has completed all but the last 5 mm of the firing stroke, for example, the processor 3008 can assume that the operator meant to complete the firing stroke and automatically complete the firing stroke.

Referring again to FIG. 1, the interface 3001 of the surgical instrument 2200 may include a home state input 3014. The operator may utilize the home state input to transmit a home state input signal to the processor 3008 to return the surgical instrument 2200 to home state which may include returning the end effector 2208 to the articulation home state position and/or the firing member to the firing home state position. As illustrated in FIGS. 3 and 7, the home state input 3014 may include a cap or a cover, for example, which can be depressed by the operator to close the switch 3004C and transmit the home state input signal through the circuit 3006C to the processor 3008. In certain instances, the home state input 3014 can be configured to return the end effector 2208 to the articulation home state position, and a separate input can be utilized to return the firing member to the firing home state position. In certain instances, the home state input 3014 can be configured to return the firing member to the firing home state position, and a separate input can be utilized to return the end effector 2208 to the articulation home state position such as, for example, the rocker 3012.

In various instances, the processor 3008 can be configured to cause the firing member to return to the firing home state position and the end effector 2208 to return to the articulation home state position upon receiving the home state input signal from the home state input 3014. In certain instances, the response of the processor 3008 to the home state input signal may depend on whether the surgical instrument 2200 is in a firing mode or an articulation mode; if the processor 3008 determines that the surgical instrument 2200 is in the articulation mode, the processor 3008 may cause the end effector 2208 to return to the articulation home state position in response to the home state input signal, for example; and if the processor 3008 determines that the surgical instrument 2200 is in the firing mode, the processor 3008 may cause the firing member to return to the firing home state position in response to the home state input signal, for example. In certain instances, the firing member can be advanced axially to fire the staples from the staple cartridge 10006 only when the end effector 2208 is in the closed configuration. In such instances, the surgical instrument 2200 can be in the firing mode only when the end effector 2208 is in the closed configuration. In certain instances, the end effector 2208 can be articulated only when the end effector 2208 is in the open configuration. In such instances, the surgical instrument 2200 can be in the articulation mode only when the end effector 2208 is in the open configuration. Accordingly, in certain instances, the processor 3008 can be configured to determine whether the surgical instrument 2200 is in the articulation mode or the firing mode by determining whether the end effector 2208 is in the open configuration or the closed configuration. In certain instances, one or more sensors 3016 (FIG. 3) can be employed by the processor 3008 to determine whether the end effector 2208 is in the open configuration or closed configuration.

Figure 10:
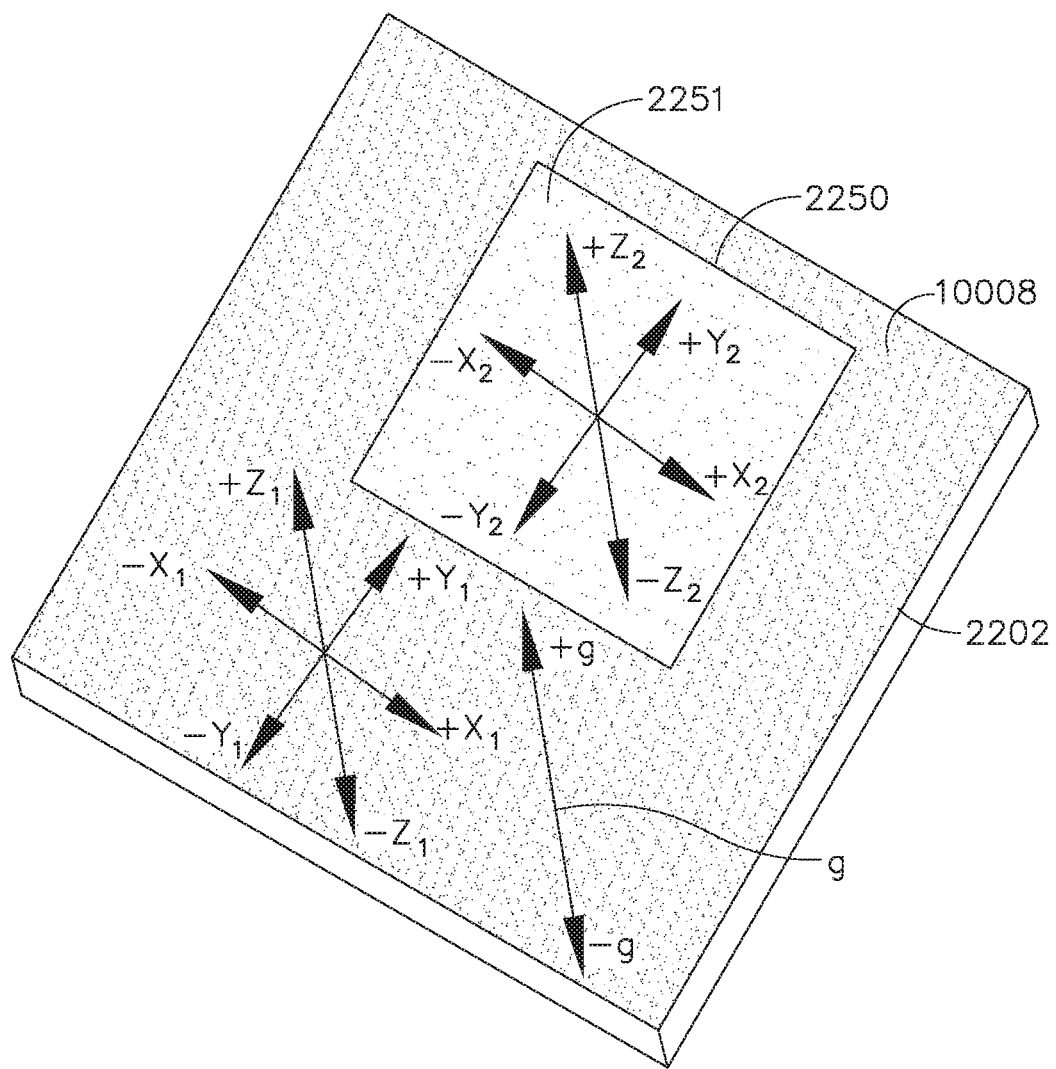
FIG. 10 is a schematic illustration of a partial view of a handle assembly of the surgical instrument of FIG. 1 depicting a display.

Referring now to FIGS. 1 and 10, the surgical instrument 2200 may comprise a screen 2251 which may be included in the handle assembly 2202, for example. The screen 2251 can be employed by one or more of the microcontrollers described herein to alert, guide, and/or provide feedback to the operator of the surgical instrument 2200, for example. The screen 2251 can produce an output display 2250. In use, the operator may tilt, flip, and/or rotate the handle assembly 2202, for example, and, in response, the microcontroller can change the orientation of the output display 2250 to improve, align, and/or adjust the orientation of the output display 2250 with respect to the view of the operator of the surgical instrument 2200 and/or any suitable frame of reference, such as an inertial, or at least substantially inertial, frame of reference, for example. A fixed frame of reference can be defined, at least in part, by gravity. In some instances, the downward acceleration of Earth's gravity can be represented by the vector $-g$ in FIG. 10. In certain instances, a processor, such as the processor 3008, for example, may be configured to detect the changes in the position of the handle assembly 2202 with respect to the frame of reference and adopt one of a plurality of orientations of the screen 2251 in accordance with the relative position of the screen 2251 with respect to the frame of reference.

In certain instances, as illustrated in FIG. 10, the screen 2251 can be disposed on a top surface 10008 of the handle assembly 2202. In various instances, the surface 10008 may extend in a first plane defined by coordinates X1 and Y1 of a first set of Cartesian coordinates representing the handle assembly 2202. In various instances, the screen 2251 may be positioned within the first plane. In some instances, the screen 2251 may be positioned within a plane which extends parallel to the first plane and/or any suitable plane in a fixed relationship relative to the first plane. For the purposes of convenience herein, it will be assumed that the first set of Cartesian coordinates representing the handle assembly are aligned with the screen 2251 and, thus, referred to as a screen set of Cartesian coordinates. The output display 2250 can reside in a second plane defined by coordinates X2 and Y2 of a second, or display, set of Cartesian coordinates. In certain instances, as illustrated in FIG. 10, the first plane can be coplanar with the second plane, for example. Moreover, the first, or screen, set of Cartesian coordinates can be aligned with the second, or display, set of Cartesian coordinates, in at least some instances. For example, +X1 can be aligned with or parallel to +X2, +Y1 can be aligned with or parallel to +Y2, and +Z1 can be aligned with or parallel to +Z2. Correspondingly, in such instances, −X1 can be aligned with or parallel to −X2, −Y1 can be aligned with or parallel to −Y2, and −Z1 can be aligned with or parallel to −Z2. As will be described in greater detail below, the second, or display, set of Cartesian coordinates can be realigned with respect to the first, or screen, set of Cartesian coordinates in certain instances. In various instances, a certain arrangement of the display Cartesian coordinates can be preferred. For instance, a neutral position of the surgical instrument 2200 can coincide with the +Z1 axis of the screen coordinates being aligned with the +g vector. As will be described in greater detail below, the processor 3008 can tolerate a certain amount of deviation between the screen coordinates at the reference frame without changing the alignment of the display coordinates; however, beyond a certain deviation between the screen coordinates at the reference frame, the processor can change the alignment of the display coordinates relative to the screen coordinates.

Figure 11:
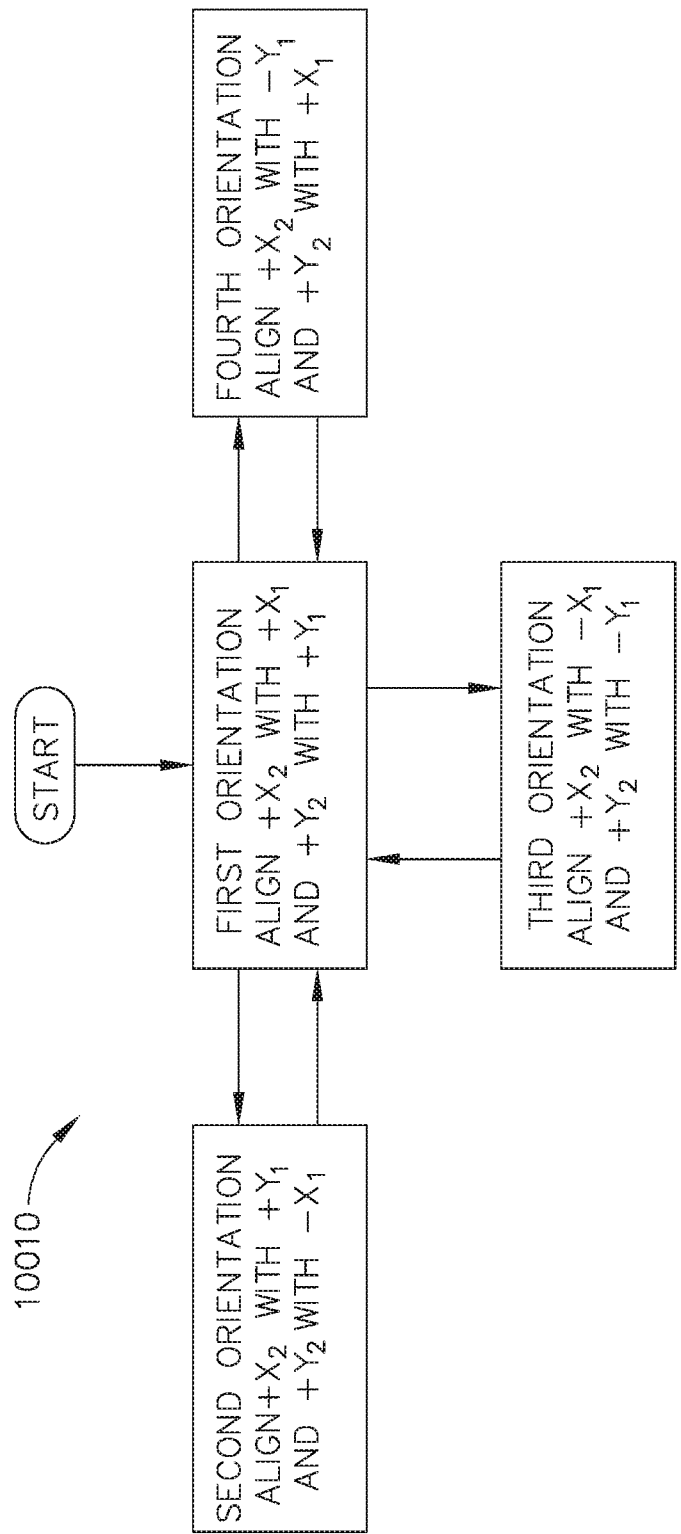
FIG. 11 depicts a module of the surgical instrument of FIG. 1.
Figure 12A:
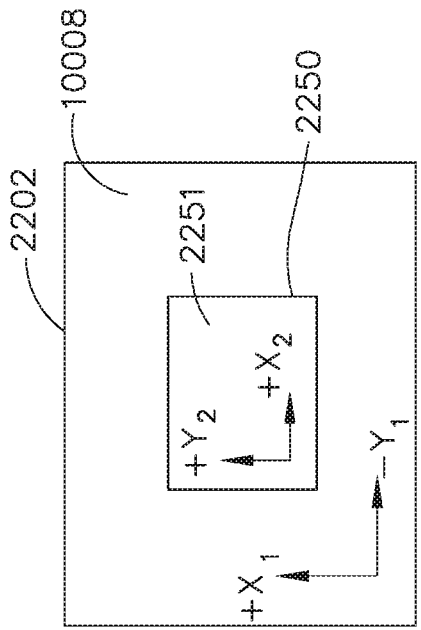
FIG. 12A is a schematic illustration of a screen orientation of the display of FIG. 10.
Figure 12C:
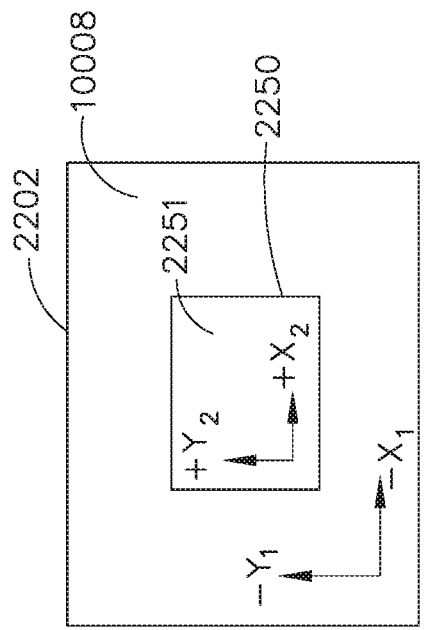
FIG. 12C is a schematic illustration of a screen orientation of the display of FIG. 10.
Figure 12B:
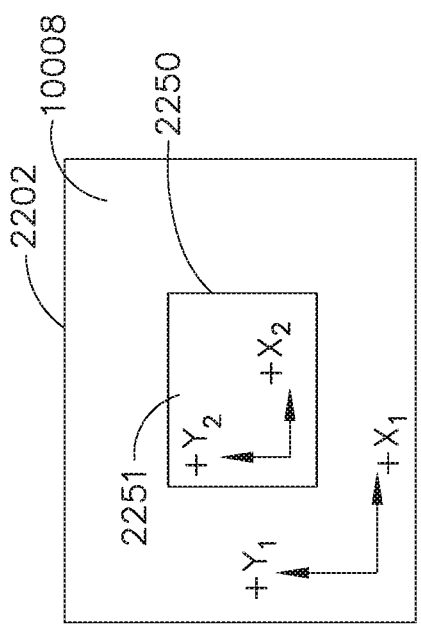
FIG. 12B is a schematic illustration of a screen orientation of the display of FIG. 10.
Figure 12D:
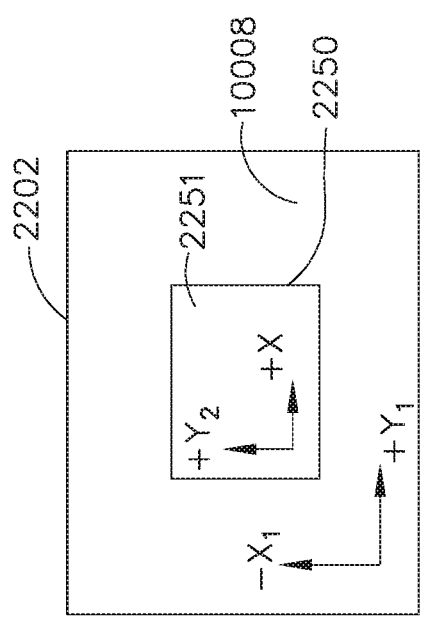
FIG. 12D is a schematic illustration of a screen orientation of the display of FIG. 10.

Referring to FIGS. 11-12D, a module 10010 can be configured to change or alter the orientation of the output display 2250 between a plurality of orientations in response to the changes in the position of the handle assembly 2202 which can be monitored through input from one or more accelerometers (not shown) that can be housed within the handle assembly 2202, for example. As discussed above, and as illustrated in FIG. 12A, the output display 2250 may adopt a first orientation wherein the +X2 and +Y2 vectors of the display set of Cartesian coordinates are aligned, or at least substantially aligned, with the +X1 and +Y1 vectors, respectively, of the screen set of Cartesian coordinates when the surgical instrument is in its neutral position. In certain instances, as illustrated in FIG. 12B, the output display 2250 may adopt a second orientation wherein the +Y2 and +X2 vectors of the display set of Cartesian coordinates are aligned, or at least substantially aligned, with the +Y1 and −X1 vectors, respectively, of the screen set of Cartesian coordinates, for example. In certain instances, as illustrated in FIG. 12C, the output display 2250 may adopt a third orientation wherein the +X2 and +Y2 vectors of the display set of Cartesian coordinates are aligned, or at least substantially aligned, with the −X1 and −Y1 vectors, respectively, of the screen set of Cartesian coordinates, for example. In certain instances, as illustrated in FIG. 12D, the output display 2250 may adopt a fourth orientation wherein the +X2 and +Y2 vectors of the second set of Cartesian coordinates are aligned, or at least substantially aligned, with the −Y1 and +X1 vectors, respectively, of the screen set of Cartesian coordinates, for example. Other orientations are possible.

Referring to FIGS. 11-12D, the processor 3008 can be configured to toggle the orientation of the output display 2250 between a plurality of orientations including the first orientation, the second orientation, the third orientation, and/or the fourth orientation, for example, to accommodate changes in the position of the handle assembly 2202, for example. In certain instances, the module 10010 may include a hysteresis control algorithm to prevent dithering of the orientation while toggling between the first, second, third, and/or fourth orientations, for example. A hysteresis control algorithm can produce a lag between an initial detection of an event that would result in a display orientation change and the processor command to change the display orientation. As such, the hysteresis control algorithm can ignore events which would result in a potentially transient orientation and optimally wait to reorient the display until a steady state, or sufficiently steady state, condition has been reached. In certain instances, the processor 3008 can be configured to orient the output display 2250 in the first orientation when an angle between the +Z1 vector of the Z1 axis and the −g vector of the gravity axis g is less than or equal to a maximum angle, for example. In certain instances, the processor 3008 can be configured to orient the output display 2250 in the second orientation when an angle between the +X1 vector of the X1 axis and the +g vector of the gravity axis g is less than or equal to a maximum angle, for example. In certain instances, the processor 3008 can be configured to orient the output display 2250 in the third orientation when an angle between the +Y1 vector of the Y1 axis and the +g vector of the gravity g axis is less than or equal to a maximum angle, for example. In certain instances, the processor 3008 can be configured to orient the output display 2250 in the fourth orientation when an angle between the +X1 vector of the X1 axis and the −g vector of the gravity axis g is less than or equal to a maximum angle, for example. In certain instances, the maximum angle can be any angle selected from a range of about 0 degrees, for example, to about 10 degrees, for example. In certain instances, the maximum angle can be any angle selected from a range of about 0 degrees, for example, to about 5 degrees, for example. In certain instances, the maximum angle can be about 5 degrees, for example. The maximum angles described above are exemplary and are not intended to limit the scope of the present disclosure.

Referring to FIGS. 11-12D, in certain instances, the processor 3008 can be configured to orient the output display 2250 in the first orientation when the +Z1 vector of the Z1 axis and the −g vector of the gravity axis g are aligned, or at least substantially aligned with each other, for example. In certain instances, the processor 3008 can be configured to orient the output display 2250 in the second orientation when the +X1 vector of the X1 axis and the +g vector of the gravity axis g are aligned, or at least substantially aligned with each other, for example. In certain instances, the processor 3008 can be configured to orient the output display 2250 in the third orientation when the +Y1 vector of the Y1 axis and the +g vector of the gravity g axis are aligned, or at least substantially aligned with each other, for example. In certain instances, the processor 3008 can be configured to orient the output display 2250 in the fourth orientation when the +X1 vector of the X1 axis and the −g vector of the gravity axis g are aligned, or at least substantially aligned with each other, for example.

Referring to FIGS. 11-12D, in certain instances, the processor 3008 can be configured to rotate the output display 2250 from the first orientation to the second orientation if the handle 2212 is rotated clockwise about the longitudinal axis LL (FIG. 1) by an angle selected from a range of about 80 degrees, for example, to about 100 degrees, for example. If the handle 2212 is rotated clockwise about the longitudinal axis LL by less than 80 degrees, the processor 3008 may not reorient the output display 2250, in this example. In certain instances, the processor 3008 can be configured to rotate the display 2250 from the first orientation to the fourth orientation if the handle 2212 is rotated counterclockwise about the longitudinal axis LL by an angle selected from a range of about 80 degrees, for example, to about 100 degrees, for example. If the handle 2212 is rotated counterclockwise about the longitudinal axis LL by less than 80 degrees, the processor 3008 may not reorient the output display 2250, in this example.

As described above, the operator may use the rocker 3012 to articulate the end effector 2208, for example. In certain instances, the operator may move their finger in a first direction to tilt the rocker 3012 to depress the dome switch 3004A to articulate the end effector 2208 in a clockwise direction to the right, for example; and the operator may move their finger in a second direction, opposite the first direction, to depress the dome switch 3004B to articulate the end effector 2208 in a counterclockwise direction to the left, for example.

Depending on the position and/or orientation of the rocker 3012 with respect to the interface 3001 and/or the handle assembly 2202, in certain instances, in a first or neutral position of the handle assembly 2202, the first direction can be an upward direction, for example, and the second direction can be a downward direction, for example, as illustrated in FIGS. 1 and 14A. In such instances, the operator of the surgical instrument 2200 may become accustomed to moving their finger up, for example, to articulate the end effector 2208 to the right, for example; and the operator may become accustomed to moving their finger down, for example, to articulate the end effector 2208 to the left, for example. In certain instances, however, the operator may change the position of the handle assembly 2202 to a second position such as an upside down position, for example, as illustrated in FIG. 14B. In such instances, if the operator does not remember to reverse the direction of movement of their finger, the operator may unintentionally articulate the end effector 2208 in an opposite direction to the direction the operator intended.

Figure 13:
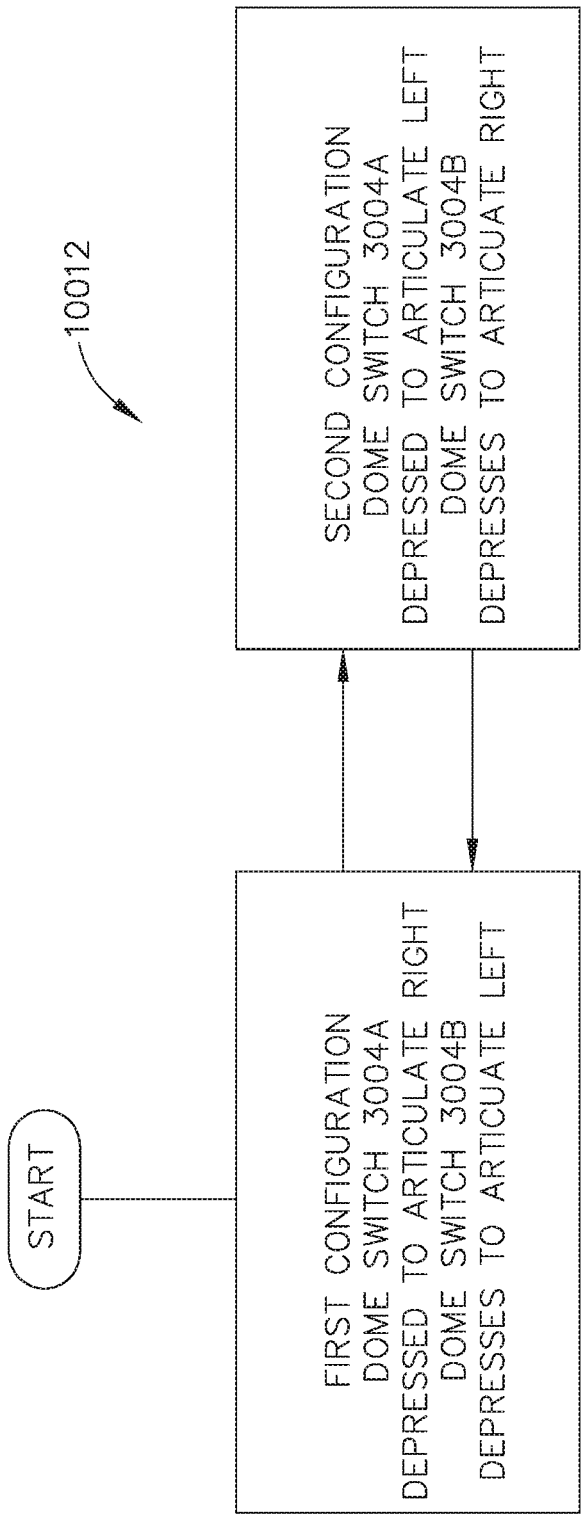
FIG. 13 depicts a module of the surgical instrument of FIG. 1.

Referring to FIG. 13, the surgical instrument 2200 may comprise a module 10012 which may allow the operator to maintain the directions of movement to which a surgeon may have become accustomed with respect to the operation of the surgical instrument 2200. As discussed above, the processor 3008 can be configured to toggle between a plurality of configurations in response to changes in the position and/or orientation of the handle assembly 2202, for example. In certain instances, as illustrated in FIG. 13, the processor 3008 can be configured to toggle between a first configuration of the interface 3001 associated with a first position and/or orientation of the handle assembly 2202, and a second configuration of the interface 3001 associated with a second position and/or orientation of the handle assembly 2202.

In certain instances, in the first configuration, the processor 3008 can be configured to command an articulation motor to articulate the end effector 2208 to the right when the dome switch 3004A is depressed, for example, and the processor 3008 can be configured to command an articulation motor to articulate the end effector 2208 to the left when the dome switch 3004B is depressed, for example. In the second configuration, the processor 3008 can command an articulation motor to articulate the end effector 2208 to the left when the dome switch 3004A is depressed, for example, and the processor 3008 can command an articulation motor to articulate the end effector 2208 to the right when the dome switch 3004B is depressed, for example. In various embodiments, a surgical instrument can comprise one motor to articulate the end effector 2208 in both directions while, in other embodiments, the surgical instrument can comprise a first motor configured to articulate the end effector 2208 in a first direction and a second motor configured to articulate the end effector 2208 in a second direction.

Referring to FIGS. 13-14B, the processor 3008 can be configured to adopt the first configuration while the handle assembly 2202 is in the first position and/or orientation, for example, and adopt the second configuration while the handle assembly 2202 is in the second position and/or orientation, for example. In certain instances, the processor 3008 can be configured to detect the orientation and/or position of the handle assembly 2202 through input from one or more accelerometers (not shown) which can be housed within the handle assembly 2202, for example. Such accelerometers, in various instances, can detect the orientation of the handle assembly 2202 with respect to gravity, i.e., up and/or down.

In certain instances, the processor 3008 can be configured to adopt the first configuration while an angle between a vector D (FIG. 1) extending through the handle assembly 2202 and the gravity vector g is any angle in the range of about 0 degrees, for example, to about 100 degrees, for example. In certain instances, the processor 3008 can be configured to adopt the first configuration while the angle between the vector D and the gravity vector g is any angle in the range of about 0 degrees, for example, to about 90 degrees, for example. In certain instances, the processor 3008 can be configured to adopt the first configuration while the angle between the vector D and the gravity vector g is less than or equal to about 80 degrees, for example.

In certain instances, the processor 3008 can be configured to adopt the second configuration while the angle between the vector D and the gravity vector g is greater than or equal to about 80 degrees, for example. In certain instances, the processor 3008 can be configured to adopt the second configuration while the angle between the vector D and the gravity vector g is greater than or equal to about 90 degrees, for example. In certain instances, the processor 3008 can be configured to adopt the second configuration while the angle between the vector D and the gravity vector g is greater than or equal to about 100 degrees, for example.

The reader will appreciate that the described orientations and/or positions of the handle assembly 2202 and their corresponding configurations which are adopted by the processor 3008 are exemplary in nature and are not intended to limit the scope of the present disclosure. The processor 3008 can be configured to adopt various other configurations in connection with various other orientations and/or positions of the handle assembly 2202.

Referring to FIG. 15, in certain instances, the surgical instrument 2200 can be controlled and/or operated, or at least partially controlled and/or operated, by input from an operator received through a display such as, for example, the display 2250; the display 2250 may comprise a touchscreen adapted to receive the input from the operator which can be in the form of one or more touch gestures. In various instances, the display 2250 may be coupled to a processor such as, for example, the processor 3008 which can be configured to cause the surgical instrument 2200 to perform various functions in response to the touch gestures provided by the operator. In certain instances, the display 2250 may comprise a capacitive touchscreen, a resistive touchscreen, or any suitable touchscreen, for example.

Referring again to FIG. 15, the display 2250 may comprise a plurality of icons which can be associated with a plurality of functions that can be performed by the surgical instrument 2200. In certain instances, the processor 3008 can be configured to cause the surgical instrument 2200 to perform a function when an icon representing such function is selected, touched, and/or pressed by the operator of the surgical instrument 2200. In certain instances, a memory such as, for example, the memory 3010 may comprise one or more modules for associating the plurality of icons with the plurality of functions.

In certain instances, as illustrated in FIG. 15, the display 2250 may include a firing icon 10014, for example. The processor 3008 can be configured to detect a firing input signal when the operator touches and/or presses the firing icon 10014. In response to the detection of the firing input signal, the processor 3008 can be configured to activate the motor 2216 to motivate a firing member of the surgical instrument 2200 to fire the staples from the staple cartridge 10006 and/or cut tissue captured between the anvil 10002 and the staple cartridge 10006, for example. In certain instances, as illustrated in FIG. 15, the display 2250 may include an articulation icon 10016 for articulating the end effector 2208 in a first direction such as, for example, a clockwise direction, for example; the display 2250 may also include an articulation icon 10018 for articulating the end effector 2208 in a second direction such as, for example, a counterclockwise direction. The reader will appreciate that the display 2250 may comprise various other icons associated with various other functions that the processor 3008 may cause the surgical instrument 2200 to perform when such icons are selected, touched, and/or pressed by the operator of the surgical instrument 2200, for example.

In certain instances, one or more of the icons of the display 2250 may comprise words, symbols, and/or images representing the function that can be performed by touching or pressing the icons, for example. In certain instances, the articulation icon 10016 may show an image of the end effector 2208 articulated in the clockwise direction. In certain instances, the articulation icon 10018 may show an image of the end effector 2208 articulated in the counter-clockwise direction. In certain instances, the firing icon 10014 may show an image of the staples being fired from the staple cartridge 10006.

Figure 16:
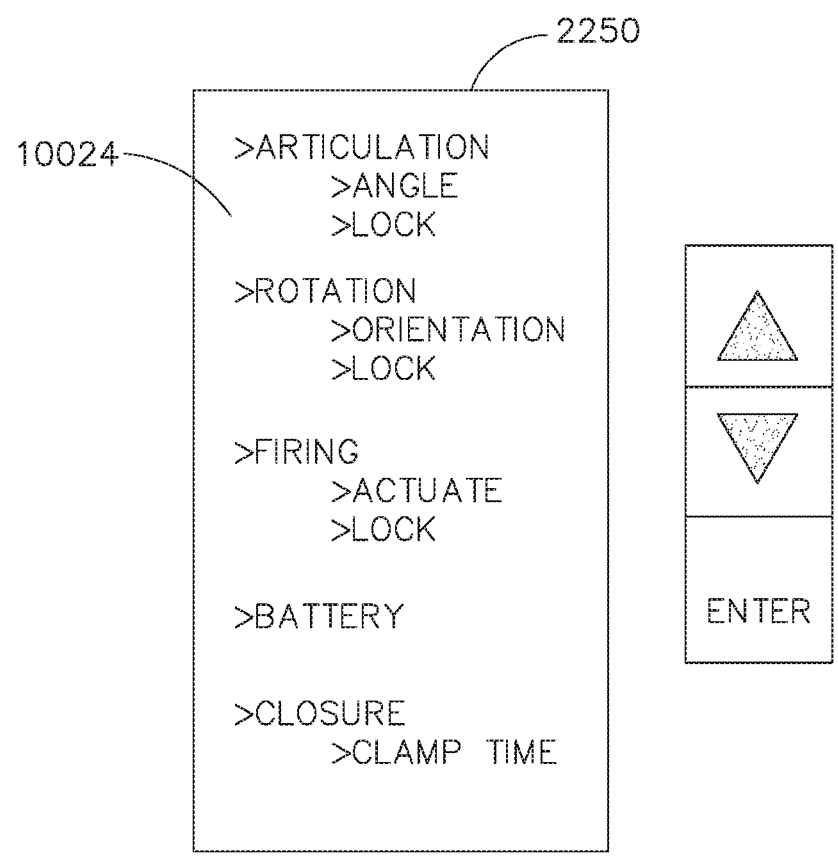
FIG. 16 is a schematic illustration of the display of FIG. 10 showing a navigational menu.
Figure 17:
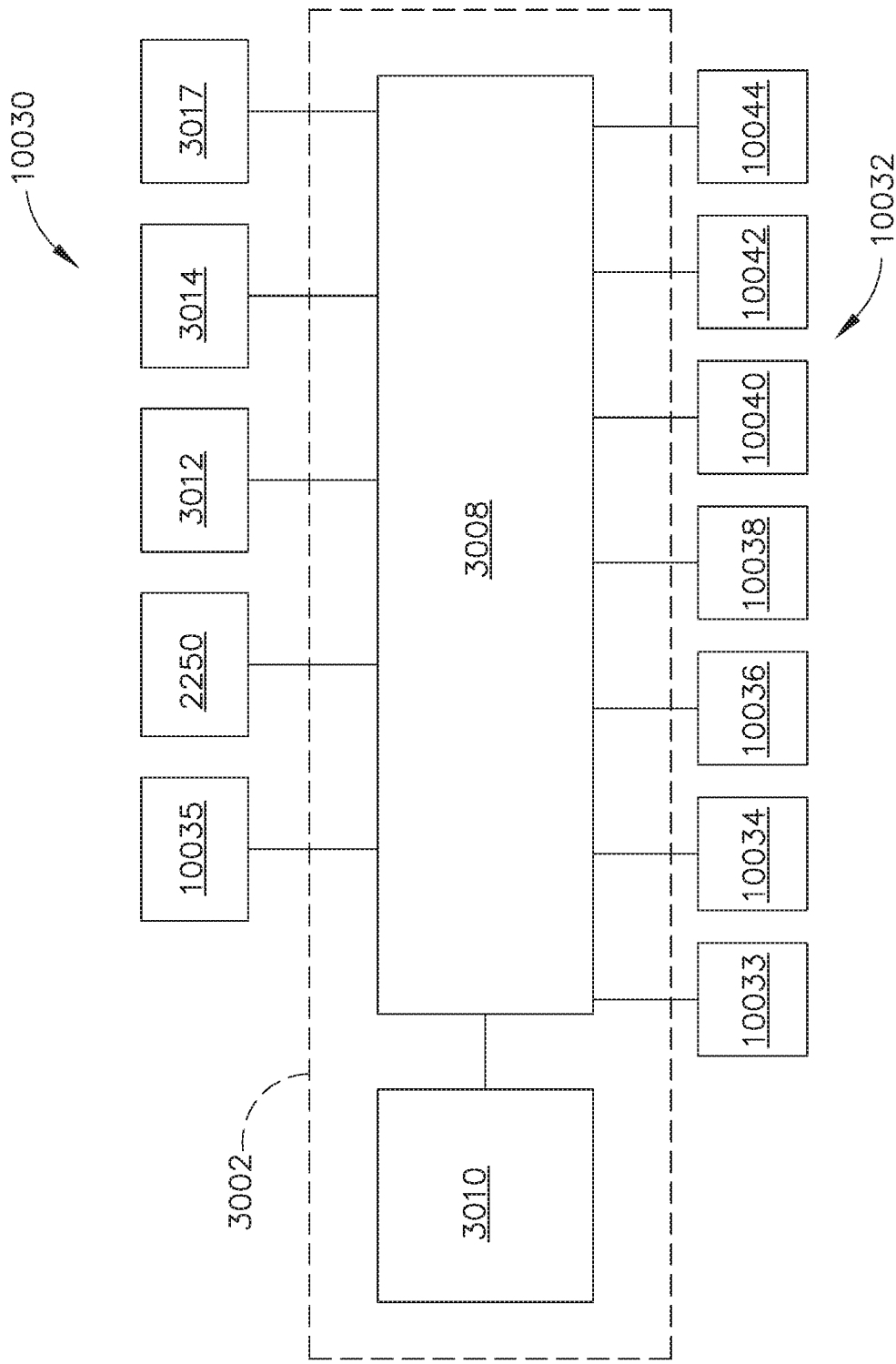
FIG. 17 is a schematic block diagram of an indicator system of the surgical instrument of FIG. 1.

Referring to FIGS. 1 and 16, the interface 3001 of the surgical instrument 2200 may comprise a plurality of operational controls such as, for example, a closure trigger 10020, a rotation knob 10022, the articulation rocker 3012, and/or a firing input 3017 (FIG. 17). In certain instances, various operational controls of the interface 3001 of the surgical instrument 2200 may serve, in addition to their operational functions, as navigational controls. In certain instances, the surgical instrument 2200 may comprise an operational mode and a navigational mode. In the operational mode, some or all of the controls of the surgical instrument 2200 may be configured to perform operational functions; and in the navigational mode, some or all of the controls of the surgical instrument 2200 may be configured to perform navigational functions. In various instances, the navigational functions performed by some or all of the controls of the surgical instrument 2200 can be related to, associated with, and/or connected to the operational functions performed by the controls. In other words, the operational functions performed by the controls of the surgical instrument 2200 may define the navigational functions performed by such controls.

Referring to FIGS. 1 and 16, in certain instances, a processor such as, for example, the processor 3008 can be configured to toggle between a primary interface configuration while the surgical instrument 2200 is in the operational mode and a secondary interface configuration while the surgical instrument 2200 is in the navigational mode; the processor 3008 can be configured to assign operational functions to some or all of the controls of the interface 3001 in the operational mode and assign navigational functions to such controls in the navigational mode, for example. In certain instances, the navigational functions of the controls in the secondary interface configuration are defined by the operational functions of the controls in the primary interface configuration, for example.

Referring to FIGS. 16, in certain instances, the operator of the surgical instrument 2200 may activate the navigational mode by opening or activating a navigational menu 10024 in the display 2250, for example. In certain instances, the surgical instrument 2200 may comprise a navigational mode button or a switch (not shown) for activating the navigational mode. In any event, the processor 3008 may switch the controls of the interface 3001 from the primary interface configuration to the secondary interface configuration upon receiving a navigational mode input signal.

As illustrated in FIG. 16, the navigational menu 10024 may comprise various selectable categories, menus, and/or folders and/or various subcategories, sub-menus, and/or subfolders. In certain instances, the navigational menu 10024 may comprise an articulation category, a firing category, a closure category, a battery category and/or, rotation category, for example.

In certain instances, the articulation rocker 3012 can be utilized to articulate the end effector 2208, in the operational mode, as described above, and can be utilized to select the articulation category, and/or launch and/or navigate an articulation menu in the navigational mode, for example. In certain instances, the firing input 3017 (FIG. 17) can be utilized to fire the staples, in the operational mode, as described above, and can be utilized to select the firing category, and/or launch and/or navigate a firing menu in the navigational mode, for example. In certain instances, the closure trigger 10020 can be utilized to transition the end effector 2208 between an open configuration and an approximated configuration in the operational mode, as described above, and can be utilized to select the closure category, and/or launch and/or navigate a closure menu in the navigational mode, for example. In certain instances, the rotation knob 10022 can be utilized to rotate the end effector 2208 relative to the elongate shaft 2204 in the operational mode, and can be utilized to select the rotation category, and/or launch and/or navigate a rotation menu in the navigational mode, for example.

Referring primarily to FIGS. 1 and 17, the operation of the surgical instrument 2200 may involve a series or a sequence of steps, actions, events, and/or combinations thereof. In various circumstances, as illustrated in FIG. 17, the surgical instrument 2200 may include an indicator system 10030 which can be configured to guide, alert, and/or provide feedback to the operator of the surgical instrument 2200 with respect to the various steps, actions, and/or events.

In various instances, the indicator system 10030 may include a plurality of indicators 10032. In certain instances, the indicators 10032 may comprise, for example, visual indicators such as a display screens, backlights, and/or LEDs, for example. In certain instances, the indicators 10032 may comprise audio indicators such as speakers and/or buzzers, for example. In certain instances, the indicators 10032 may comprise tactile indicators such as haptic actuators, for example. In certain instances, the indicators 10032 may comprise combinations of visual indicators, audio indicators, and/or tactile indicators, for example.

Referring to FIG. 17, the indicator system 10030 may include one or more microcontrollers such as, for example, the microcontroller 3002 which may comprise one or more processors such as, for example, the processor 3008 and/or one or more memory units such as, fore example, the memory 3010. In various instances, the processor 3008 may be coupled to various sensors 10035 and/or feedback systems which may be configured to provide feedback to the processor 3008 regarding the status of the surgical instrument 2200 and/or the progress of the steps, actions, and/or events pertaining to the operation of the surgical instrument 2200, for example.

In various instances, the operation of the surgical instrument 2200 may include various steps including an articulation step, a closure step, a firing step, a firing reset step, a closure reset step, an articulation reset step, and/or combinations thereof, for example. In various instances, the articulation step may involve articulating the end effector 2208 relative to the elongate shaft 2204 to an articulated position, for example; and the articulation reset step may involve returning the end effector 2208 to an articulation home state position, for example. In various instances, the closure step may involve transitioning the end effector 2208 to a closed configuration, for example; and the closure reset step may involve transitioning the end effector 2208 to an open configuration, for example. In various instances, the firing step may involve advancing a firing member to deploy staples from the staple cartridge 10006 and/or cut tissue captured by the end effector 2208, for example. In various instances, the firing reset step may involve retraction of the firing member to a firing home state position, for example.

Referring to FIG. 17, one or more of the indicators 10032 of the indicator system 10030 can be associated with one or more of the various steps performed in connection with the operation of the surgical instrument 2200. In various instances, as illustrated in FIG. 17, the indicators 10032 may include a bailout indicator 10033 associated with the bailout assembly 2228, an articulation indicator 10034 associated with the articulation step, a closure indicator 10036 associated with the closure step, a firing indicator 10038 associated with the firing step, an articulation reset indicator 10040 associated with the articulation reset step, a closure reset indicator 10042 associated with the closure reset step, and/or a firing reset indicator 10044 associated with the firing reset step, for example. The reader will appreciate that the above described steps and/or indicators are exemplary in nature and are not intended to limit the scope of the present disclosure. Various other steps and/or indicators are contemplated by the present disclosure.

Referring to FIG. 1, in various instances, one or more of the controls of the interface 3001 can be employed in one or more of the steps of operation of the surgical instrument 2200. In certain instances, the closure trigger 10020 can be employed in the closure step, for example. In certain instance, the firing input 3017 (FIG. 17) can be employed in the firing step, for example. In certain instances, the articulation rocker 3012 can be employed in the articulation step and/or the articulation reset step, for example. In certain instances, the home state input 3014 can be employed in the firing reset step, for example.

Referring to FIG. 17, in various instances, the indicators 10032 associated with one of the steps of operation of the surgical instrument 10030 may also be associated with the controls employed in such steps. For example, the articulation indicator 10034 can be associated with the articulation rocker 3012, the closure indicator 10036 can be associated with the closure trigger 10020, the firing indicator 10038 can be associated with the firing input 3017, and/or the firing reset indicator 10044 can be associated with the home state input 3014. In certain instances, associating an indicator with a control of the interface 3001 may include placing or positioning the indicator on, within, partially within, near, and/or in close proximity to the control, for example, to aid the operator in associating the indicator with the control. The reader will appreciate that the above described controls and/or the indicators associated with such controls are exemplary in nature and are not intended to limit the scope of the present disclosure. Various other controls and the indicators associated with such controls are contemplated by the present disclosure.

In various instances, the processor 3008 can be configured to activate the indicators 10032 in one or more sequences defined by the order of the steps associated with the indicators 10032. For example, the operator may need to operate the surgical instrument 2200 in a series of steps starting with the articulation step followed by the closure step, and further followed by the firing step. In such example, the processor 3008 can be configured to guide the operator through the sequence of steps by activating the corresponding articulation indicator 10034, closure indicator 10036, and firing indicator 10038 in the same order as the order of the steps. In other words, the processor 3008 can be configured to first activate the articulation indicator 10034 followed by the closure indicator 10036, and further followed by the firing indicator 10038, for example. In certain instances, the surgical instrument 2200 may comprise a bypass switch (not shown) which may be configured to allow the operator to bypass a step that is recommended but not required, for example. In such instances, pressing the bypass switch may signal the processor 3008 to activate the next indicator in the sequence.

In various instances, the processor 3008 can be configured to toggle the indicators 10032 between a plurality of indicator configurations to guide, alert, and/or provide feedback to the operator of the surgical instrument 2200. In various instances, the processor 3008 may provide visual cues to the operator of the surgical instrument 2200 by the toggling of the indicators 10032 between the plurality of indicator configurations which may include activated and/or deactivated configurations, for example. In certain instances, one or more of the indicators 10032 may comprise a light source which can be activated in a first indicator configuration, for example, to alert the operator to perform a step associated with the indicators 10032, for example; and the light source can be deactivated in a second indicator configuration, for example, to alert the operator when the step is completed, for example.

In certain instances, the light source can be a blinking light which can be transitioned by the processor 3008 between a blinking configuration and a non-blinking configuration. In certain instances, the blinking light, in the non-blinking configuration, may be transitioned to solid illumination or turned off, for example. In certain instances, the blinking light, in the blinking configuration, may represent a waiting period while a step is in progress, for example. In certain instances, the blinking frequency of the blinking light may be changed to provide various visual cues. For example, the blinking frequency of the blinking light that represents a waiting period may be increased or decreased as the waiting period approaches its completion. The reader will appreciate that the waiting period can be a forced waiting period and/or a recommended waiting period, for example. In certain instances, forced waiting periods can be represented by a blinking configuration different from recommended waiting periods. In certain instances, the blinking light may comprise a first color representing a forced waiting period and a second color representing a recommended waiting period, wherein the first color is different from the second color. In certain instances, the first color can be a red color, for example, and the second color can be a yellow color, for example.

In various instances, one or more of the indicators 10032 can be toggled by the processor 3008 between a first indicator configuration representing controls that are available for use in a standard next step of the steps of operation of the surgical instrument 2200, a second indicator configuration representing controls that are available for use in a non-standard next step of the steps of operation of the surgical instrument 2200, and/or a third indicator configuration representing controls that are not available for use in a next step of the steps of operation of the surgical instrument 2200, for example. For instance, when the end effector 2208 of the surgical instrument 2000 is in an open configuration, the articulation indicator 10034 and the closure indicator 10036 can be illuminated indicating to the operator of the surgical instrument 2200 that those two functions, i.e., end effector articulation and end effector closure, are available to the operator at that moment. In such a state, the firing indicator 10038 may not be illuminated indicating to the operator that the firing function is not available to the operator at that moment. Once the end effector 2208 has been placed in a closed and/or clamped configuration, the articulation indicator 10034 may be deilluminated indicating to the operator that the articulation function is no longer available at that moment. In such a state, the illumination of the closure indicator 10036 may be reduced indicating to the operator that the closing function can be reversed at that moment. Moreover, in such a state, the firing indicator 10038 can become illuminated indicating to the operator that the firing function is available to the operator at that moment. Once the firing member has been at least partially advanced, the closure indicator 10036 may be deilluminated indicating that the closing function cannot be reversed at that moment. When the firing member is retracted back to its unfired position, the illumination of the firing indicator 10038 may be reduced indicating to the operator that the firing member can be readvanced, if needed. Alternatively, once the firing member has been retracted, the firing indicator 10038 may be deilluminated indicating to the operator that the firing member cannot be readvanced at that moment. In either event, the closure indicator 10036 can be reilluminated after the firing member has been retracted back to its unfired position indicating to the operator that the closing function can be reversed at that moment. The articulation indicator 10034 may remain deilluminated indicating that the articulation function is not available at that moment. Once the end effector 2208 has been opened, the firing indicator 10038 can be deilluminated, if it hadn't been deilluminated already, indicating to the operator that the firing function is not available at that moment, the closing indicator 10036 can remain illuminated or its illumination can be reduced indicating to the operator that the closing function is still available at that moment, and the articulation indicator 10034 can be reilluminated indicating to the operator that the articulation function is available at that moment. The example provided above is exemplary and other embodiments are possible.

In certain instances, the one or more of the indicators 10032 may include a light source that can be toggled by the processor 3008 between a first color in the first indicator configuration, a second color in the second indicator configuration, and/or a third color in the third indicator configuration, for example. In certain instances, the indicators 10032 can be toggled by the processor 3008 between the first indicator configuration, the second indicator configuration, and/or the third indicator configuration by changing the light intensity of the light source or scanning through the color spectrum, for example. In certain instances, the first indicator configuration may comprise a first light intensity, for example, the second indicator configuration may comprise a second light intensity, for example, and/or the third indicator configuration may comprise a third indicator configuration, for example.

In various instances, in the firing step of operation of the surgical instrument 2200, the firing member can be motivated to deploy the plurality of staples from the staple cartridge 10006 into tissue captured between the anvil 10002 and the staple cartridge 10006, and advance a cutting member (not shown) to cut the captured tissue. The reader will appreciate that advancing the cutting member to cut the captured tissue in the absence of a staple cartridge or in the presence of a spent staple cartridge may be undesirable. Accordingly, in various instances, the surgical instrument 2200 may comprise a lockout mechanism (not shown) which can be activated to prevent advancement of the cutting member in the absence of a staple cartridge or in the presence of a spent staple cartridge, for example.

Figure 18:
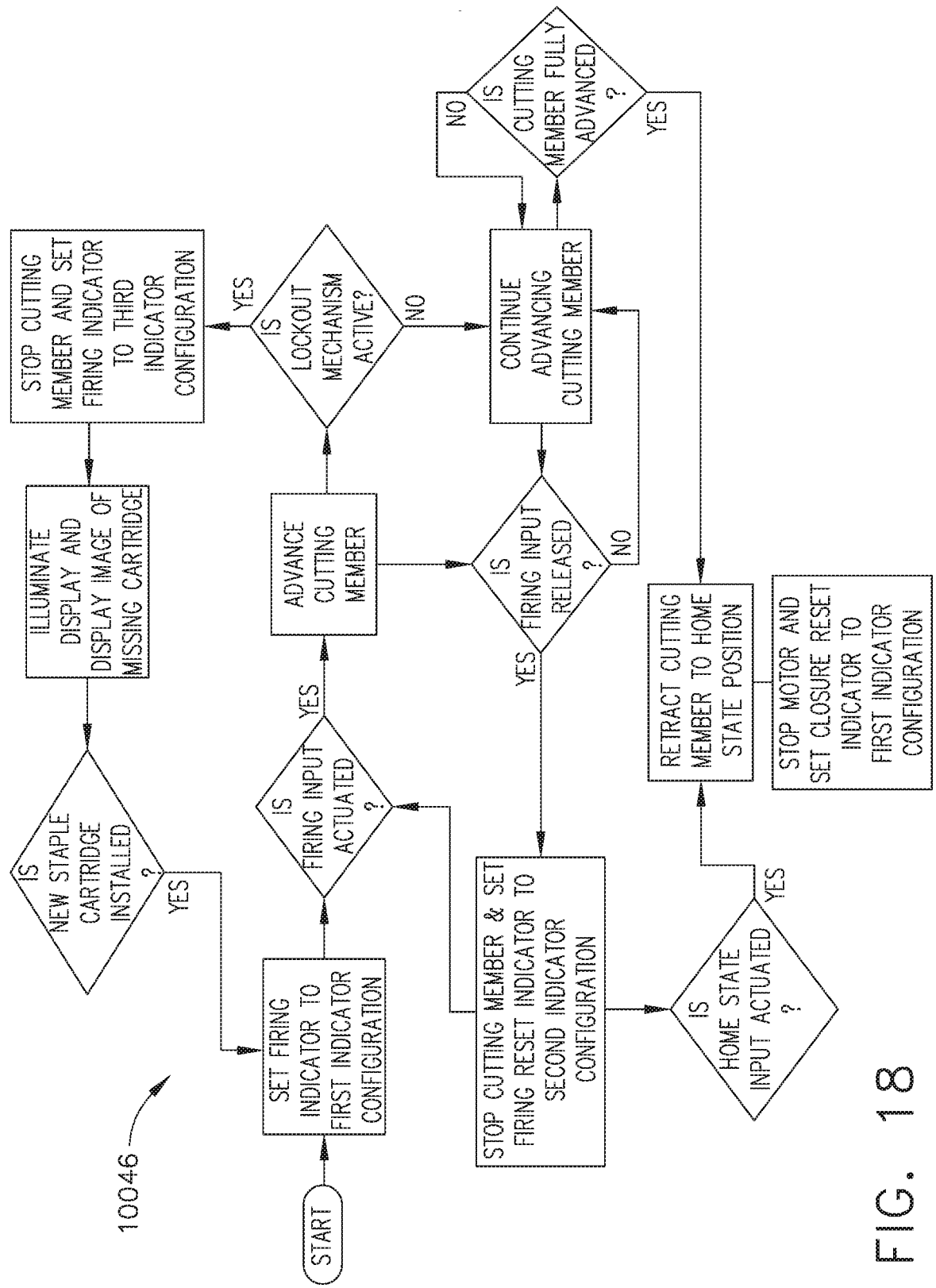
FIG. 18 is a module of the surgical instrument of FIG. 1.

Referring to FIG. 18, a module 10046 can be employed by an indicator system such as, for example, the indicator system 10030 (FIG. 17). In various instances, the module 10046 may comprise program instructions stored in one or more memory units such as, for example, the memory 3010, which when executed may cause the processor 3008 to employ the indicators 10032 to alert, guide, and/or provide feedback to the operator of the surgical instrument 2200 during the firing step of operation of the surgical instrument 2200, for example. In certain instances, one or more of the indicators 10032 such as the firing indicator 10038 and/or the firing reset indicator 10044, for example, can be toggled by the processor 3008 between the first indicator configuration, the second indicator configuration, and/or the third indicator configuration to alert, guide, and/or provide feedback to the operator of the surgical instrument 2200 during the firing step of operation of the surgical instrument 2200, for example.

Referring to FIGS. 17 and 18, the operator of the surgical instrument 2200 may actuate the firing input 3017 to cause the processor 3008 to activate the motor 2216, for example, to motivate the firing member to deploy the plurality of staples from the staple cartridge 10006 into the captured tissue and advance the cutting member to cut the captured tissue. In certain instances, the firing indicator 10038 can be set to the first indicator configuration to alert the operator that the firing input 3017 is available for use and/or is one of the standard control options available for completion of the firing step.

In certain instances, as illustrated in FIGS. 17 and 18, if the processor 3008 detects that the lockout mechanism is active, the processor 3008 may stop the advancement of the cutting member by stopping and/or deactivating the motor 2216, for example. In addition, the processor 3008 can be configured to transition the firing indicator 10038 from the first indicator configuration to the third indicator configuration to caution the operator that the firing input 3017 is not available for use. In certain instances, the processor 3008 may also be configured to illuminate the display 2250 and display an image of a missing staple cartridge, for example. In certain instances, the processor 3008 may also set the firing reset indicator 10044 to the first indicator configuration, for example, to inform the operator that home state input 3014 is available for use to motivate the firing member to retract the cutting member to the firing home state position, for example. In certain instances, the processor 3008 can be configured to detect the installation of a new staple cartridge, through the sensors 10035 for example, and in response, return the firing indicator 10038 to the first indicator configuration, for example.

In certain instances, as illustrated in FIG. 18, if the operator releases the firing input 3017 before completion of the firing step, the processor 3008 can be configured to stop the motor 2216. In certain instances, the processor 3008 may also maintain the firing indicator 10038 in the first indicator configuration, for example, to alert the operator that the firing input 3017 is available for use as the standard control option available for completion of the firing step of operation of the surgical instrument 2200, for example. In certain instances, the processor 3008 may also set the firing reset indicator 10044 to the second indicator configuration, for example, to inform the operator that home state input 3014 is available for use as a non-standard control option available for use to retract the cutting member to the firing home state position, for example, if the operator decides to abort the firing step of operation of the surgical instrument 2200, for example.

Further to the above, as illustrated in FIG. 18, if the firing input 3017 is re-actuated by the operator, the processor 3008 may, in response, reactivate the motor 2216 to continue advancing the cutting member until the cutting member is fully advanced. In certain instances, the processor 3008 may employ the sensors 10035 to detect when the cutting member is fully advanced; the processor 3008 may then reverse the direction of rotation of the motor 2216, for example, to motivate the firing member to retract the cutting member to the firing home state position, for example. In certain instances, the processor 3008 can be configured to stop the motor 2216, for example, and/or set the closure reset indicator 10042 to the first indicator configuration, for example, if the processor detects that the cutting member has reached the firing home state position, for example.

As described herein, a surgical instrument can enter into various operational states, modes, and/or configurations. In certain instances, the instrument may enter into an operational state, mode, and/or configuration that is undesired by the operator who may be unsure as to how to remove the instrument from that undesired state, mode, and/or configuration. In at least one instance, the surgical instrument can include a reset button which, when actuated, can place the instrument in a default state, mode, and/or configuration. For instance, the default state, mode, and/or configuration can comprise an operational mode, and not a navigational mode. In at least one instance, the default state and/or configuration can comprise a certain orientation of the display output 2250, for example. The reset button can be in signal communication with the processor 3008 which can place the surgical instrument in the default state, mode, and/or configuration. In certain instances, the processor 3008 can be configured to hold the surgical instrument in the default state, mode, and/or configuration. In at least one instance, the surgical instrument can include a lock button which, when actuated, can lock the surgical instrument in its default state, mode, and/or configuration. In certain instance, a lock button can lock the surgical instrument in its current state, mode, and/or configuration. The operational state, mode, and/or configuration can be unlocked by actuating the lock button once again. In various embodiments, the surgical instrument can include at least one accelerometer in signal communication with the processor 3008 which can determine when the instrument handle is being shaken or being moved back and forth quickly. When such shaking is sensed, the processor 3008 can place the surgical instrument into a default operation state, mode, and/or configuration.

Figure 19:
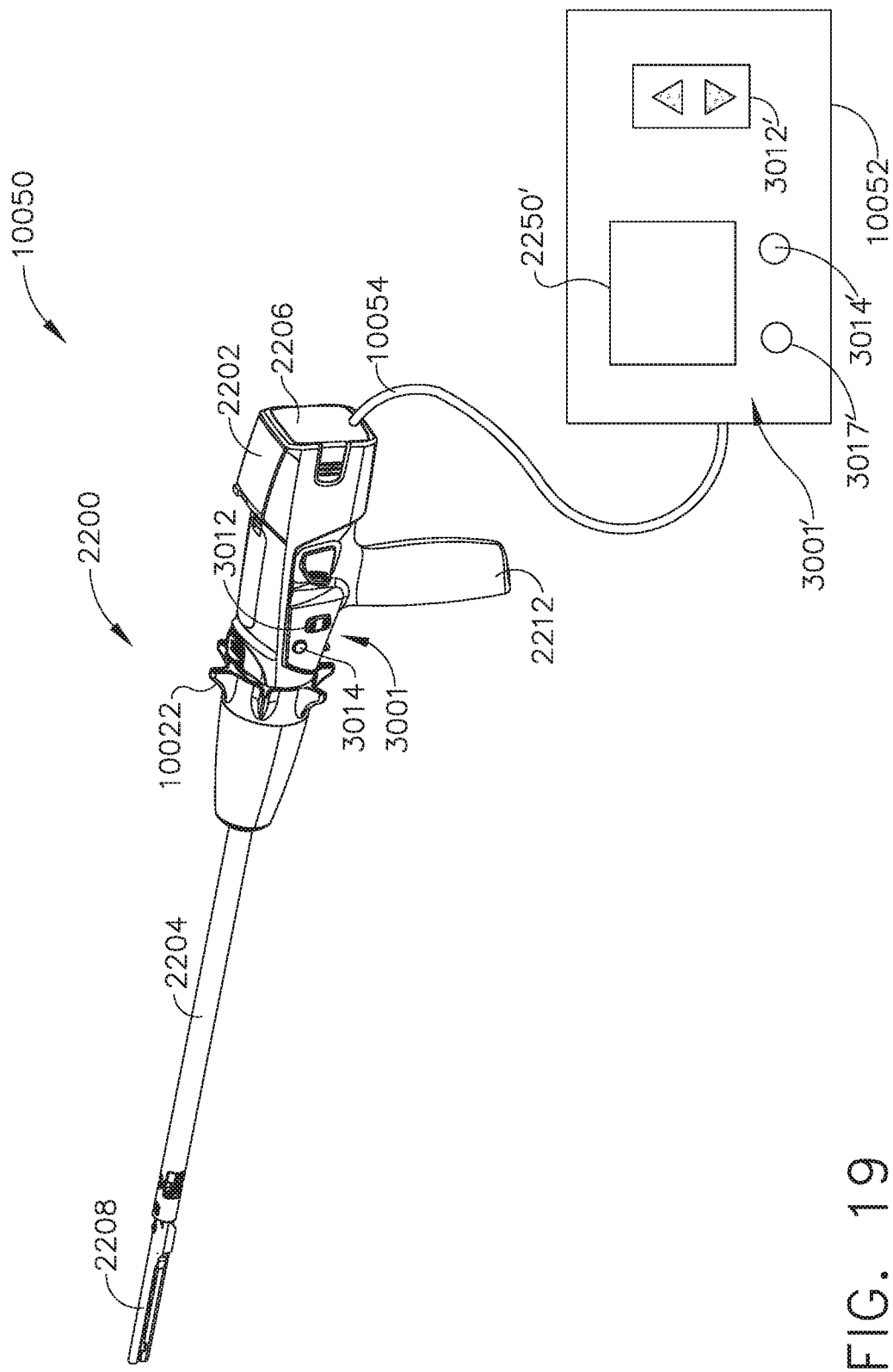
FIG. 19 is a perspective view of the surgical instrument of FIG. 1 coupled to a remote operating unit.

Referring to FIG. 19, in various instances, a surgical assembly 10050 may include a surgical instrument such as, for example, the surgical instrument 2200 and a remote operating unit 10052. In certain instances, the surgical instrument 2200 may comprise a primary interface such as, for example, the interface 3001 which may reside in the handle assembly 2202, as illustrated in FIG. 1. In certain instances, the interface 3001 may include a plurality of primary controls such as, for example, the closure trigger 10020 (FIG. 1), the rotation knob 10022, the articulation rocker 3012, the home state input 3014, and/or the firing input 3017 (FIG. 17).

In various instances, an operator of the surgical instrument 2200 may manually operate the primary controls of the interface 3001 to perform a surgical procedure, for example. As described above, the operator may actuate the articulation rocker 3012 to activate the motor 2216 to articulate the end effector 2208 between an unarticulated position and an articulated position, for example. In certain instances, the operator may actuate the closure trigger 10020 to transition the end effector 2208 between an open configuration and a closed configuration, for example. In certain instances, the operator may actuate the firing input 3017 to activate the motor 2216 to motivate the firing member of the surgical instrument 2200 to fire the staples from the staple cartridge 10006 and/or cut tissue captured between the anvil 10002 and the staple cartridge 10006, for example.

In various instances, the operator of the surgical instrument 2200 may not be sufficiently close in proximity to the handle assembly 2202 to be able to manually operate the interface 3001. For example, the operator may operate the surgical instrument 2200 together with a robotically-controlled surgical system, which may be controlled from a remote location. In such instances, the operator may need to operate the surgical instrument 2200 from the remote location where the operator operates the robotically-controlled surgical system, for example; the operator may employ the remote operating unit 10052 to operate the surgical instrument 2200 remotely, for example. Various robotic systems, instruments, components, and methods are disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, which is incorporated by reference herein in its entirety.

Figure 20:
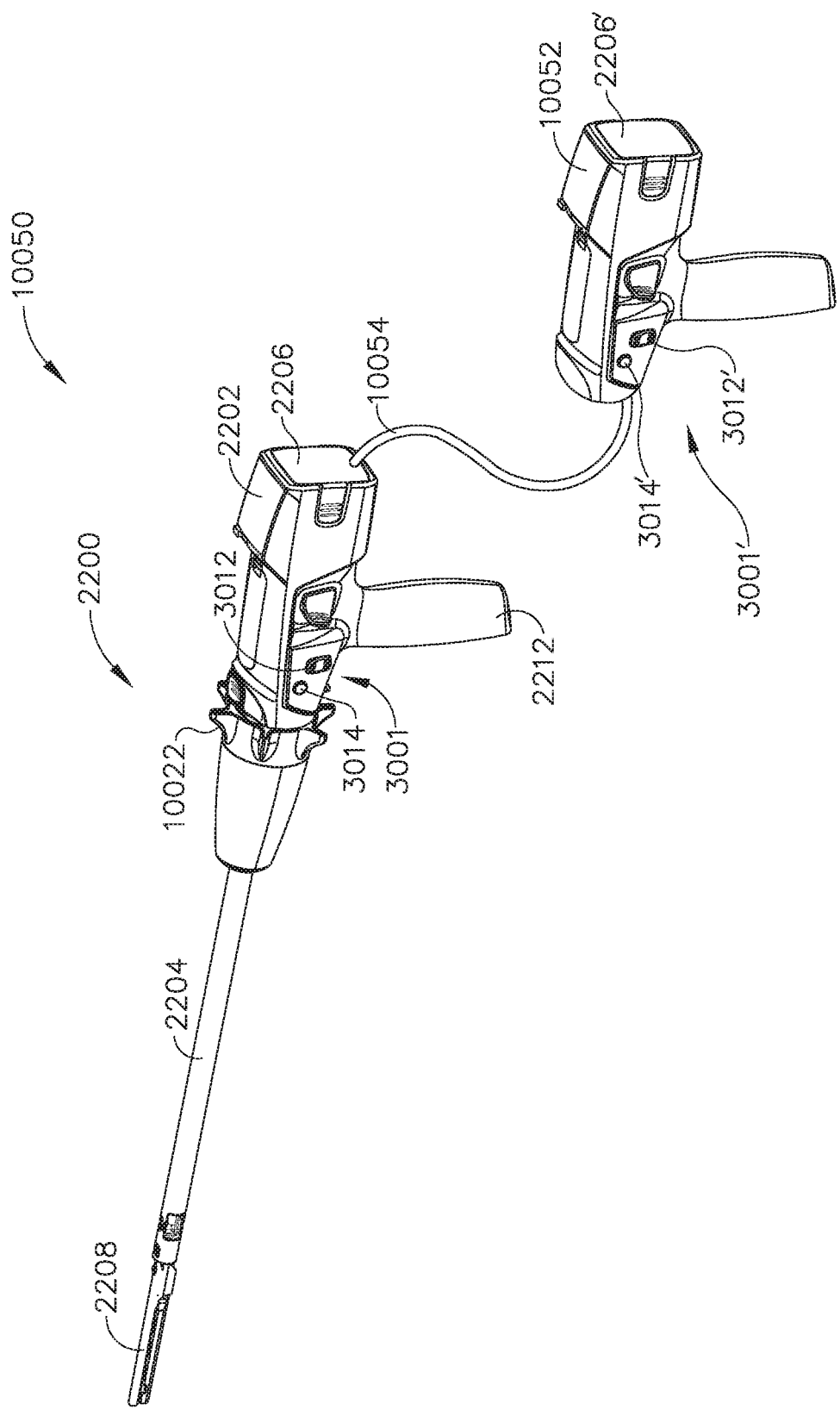
FIG. 20 is a perspective view of the surgical instrument of FIG. 1 coupled to a remote operating unit.

Referring to FIGS. 19 and 20, the remote operating unit 10052 may include a secondary interface 3001', a display 2250', and/or a power assembly 2206' (or "power source" or "power pack"), for example. In various instances, the secondary interface 3001' may include a plurality of secondary controls which may correspond to the primary controls of the primary interface 3001'. In certain instances, the remote operating unit 10052 may include a remote articulation rocker 3012' corresponding to the articulation rocker 3012, for example. In certain instances, the remote operating unit 10052 may include a remote firing input 3017' corresponding to the firing input 3017 of the surgical instrument 2200, for example. In certain instances, the remote operating unit 10052 may include a remote home state input 3014' corresponding to the home state input 3014 of the surgical instrument 2200, for example.

In certain instances, as illustrated in FIG. 19, the remote operating unit 10052, the interface 3001', and/or the plurality of secondary controls may comprise a different shape and/or design from the handle assembly 2202, the interface 3001, and/or the plurality of primary controls, respectively. In certain instances, as illustrated in FIG. 20, the remote operating unit 10052, the interface 3001', and/or the plurality of secondary controls may comprise the same, or at least substantially the same, shape and/or design to the handle assembly 2202, the interface 3001, and/or the plurality of primary controls, respectively.

Figure 21:
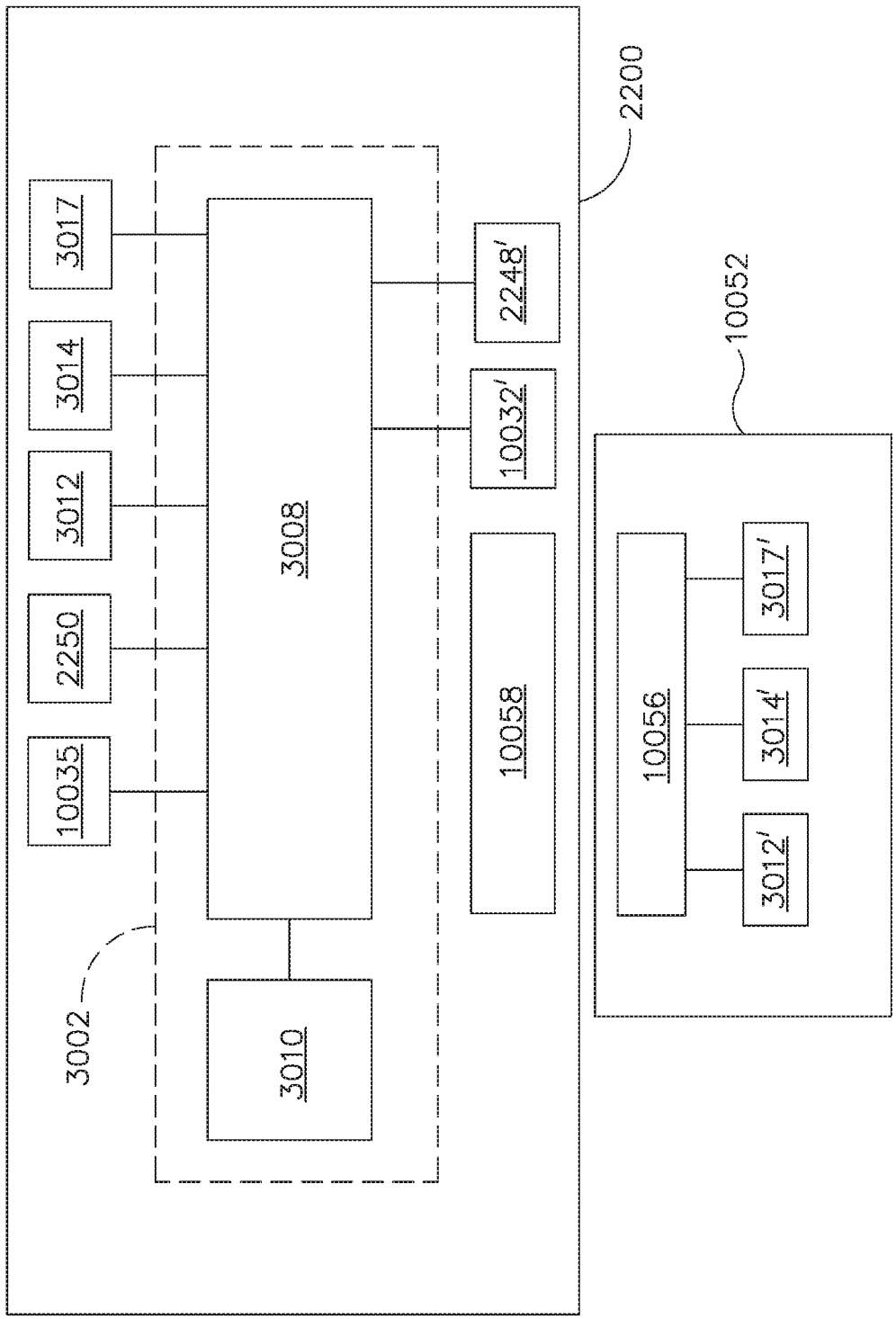
FIG. 21 is a schematic block diagram of the surgical instrument of FIG. 1 in wireless communication with a remote operating unit.

In various instances, as illustrated in FIGS. 19 and 20, the remote operating unit 10052 can be coupled to the handle assembly 2202 of the surgical instrument 2200 via an elongate flexible cable 10054, for example, which can be configured to transmit various actuation signals to the processor 3008 of the surgical instrument 2200, for example; the various actuation signals can be generated by actuating the plurality of secondary controls of the interface 3001', for example. In certain instances, as illustrated in FIG. 21, the remote operating unit 10052 may comprise a transmitter 10056 which can be configured to wirelessly transmit the actuation signals generated by the secondary controls of the secondary interface 3001' from the remote operating unit 10052 to the processor 3001, for example, through a receiver 10058 which can be located in the handle assembly 2202, for example.

In various instances, the surgical instrument 2200 and/or the remote operating unit 10052 may include communication activation inputs (not shown). In certain instances, actuating the communication activation inputs may be a precursory step to establishing communication between the surgical instrument 2200 and the remote operating unit 10052, for example; once communication is established, the operator may employ the remote operating unit 10052 to remotely control the surgical instrument 2200, for example.

In various instances, the memory 3010 may include program instructions for a puppet mode, which when executed may cause the processor 3008 to respond to the actuation signals generated by the plurality of secondary controls of the secondary interface 3001' in the same, or at least similar, manner to the response of the processor 3008 to the actuation signals generated by the plurality of primary controls of the primary interface 3001. In other words, the responses of the processor 3008 to the actuation signals generated by the plurality of secondary controls can be configured to mimic the responses of the processor 3008 to the actuation signals generated by the plurality of primary controls, for example.

In certain instances, actuation of the remote firing input 3017' may solicit the same, or at least a similar, response from the processor 3008 as the actuation of the firing input 3017; the solicited response may include activation of the motor 2216 to motivate the firing member to fire the staples from the staple cartridge 10006 and/or cut tissue captured between the anvil 10002 and the staple cartridge 10006, for example. In certain instances, actuation of the remote articulation rocker 3012' may solicit the same, or at least a similar, response from the processor 3008 as the actuation of the articulation rocker 3012; the solicited response may include activation of the motor 2216 to articulate the end effector 2208 relative to the elongate shaft 2204, for example.

In certain instances, the processor 3008 can be configured to require input actuation signals from both of the primary controls of the primary interface 3001 and the corresponding secondary controls of the secondary interface 3001' to perform the function solicited by such controls. In such instances, the remote operator of the remote operating unit 10052 may need the assistance of an additional operator who can be employed to manually actuate the primary controls of the primary interface 3001 while the remote operator actuates the secondary controls of the secondary interface 3001', for example.

In various instances, as described above, an operator may operate the surgical instrument 2200 together with a robotically-controlled surgical system, which may be controlled by a robotic control system from a remote location. In certain instances, the remote operating unit 10052 can be configured to work in tandem with the robotic control system. In certain instances, the robotic control system may include one or more control ports; and the remote operating unit 10052 may comprise connection means for coupling engagement with the control ports of the robotic control system. In such instances, the operator may operate the surgical instrument 2200 through an interface of the robotic control system, for example. In various instances, the control ports may comprise unique mechanical and/or electrical configurations which may require the use of original equipment manufacturer components to ensure consistent product quality and performance, for example.

In various instances, the remote operating unit 10052 may include various indicators 10032' which can be similar in many respects to the indicators 10032 of the handle assembly 2202. In certain instances, the indicators 10032' of the remote operating unit 10052 can be employed by the processor 3008 in the same, or at least substantially the same, manner as the indicators 10032 to guide, alert, and/or provide feedback to the operator with respect to the various steps of operation of the surgical instrument 2200.

In various instances, the remote operating unit 10052 may include various feedback devices 2248' which can be similar in many respects to the feedback devices 2248 of the handle assembly 2202. In certain instances, the feedback devices 2248' of the remote operating unit 10052 can be employed by the processor 3008 in the same, or at least substantially the same, manner as the feedback devices 2248 to provide sensory feedback to the operator with respect to the various steps of operation of the surgical instrument 2200. Similar to the feedback devices 2248, the feedback devices 2248' may include, for example, visual feedback devices, audio feedback devices, tactile feedback devices, and/or combinations thereof.

Figure 22:
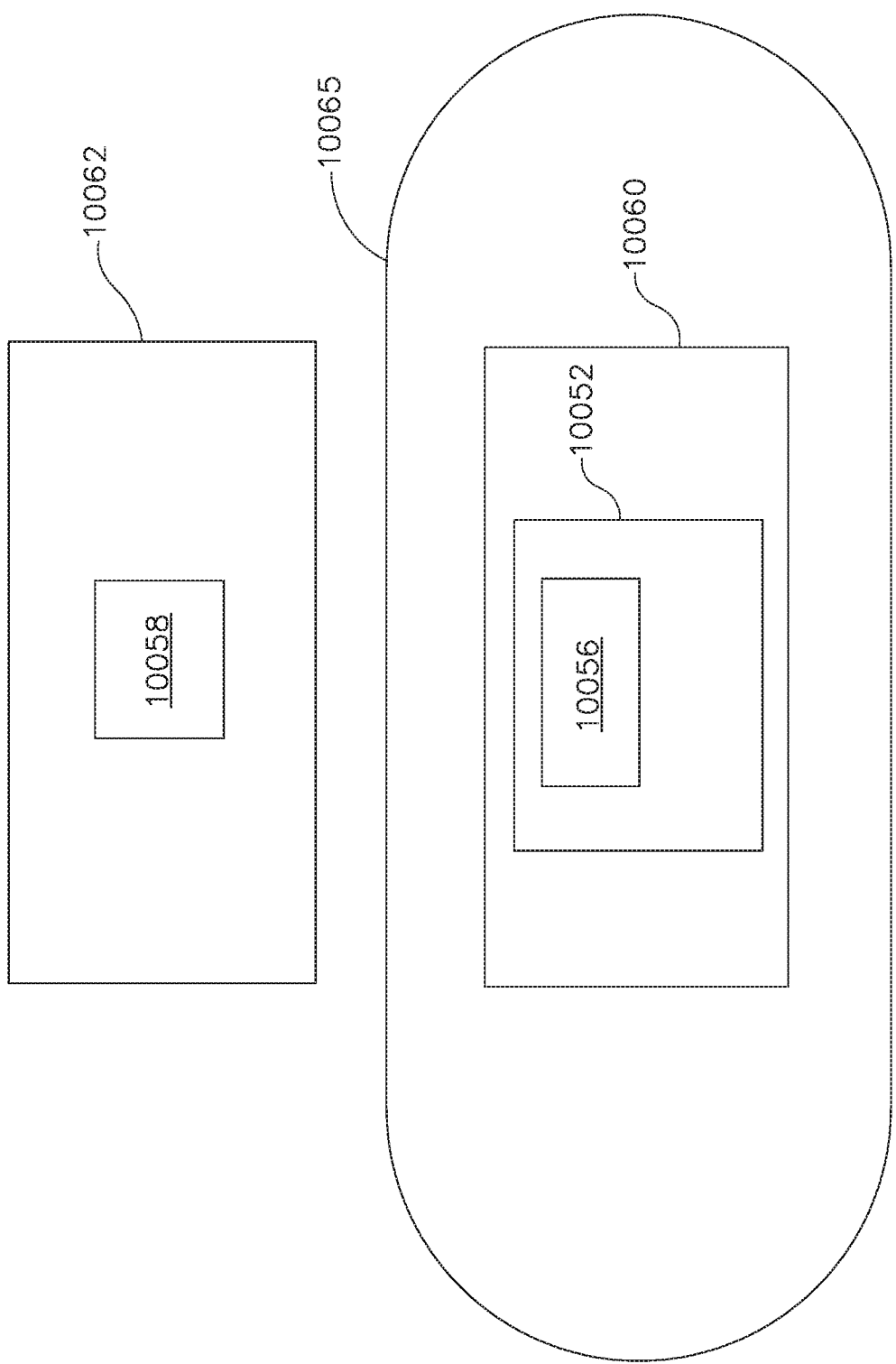
FIG. 22 is a schematic illustration of a first surgical instrument including a remote operating unit for controlling a second surgical instrument.

In various instances, as illustrated in FIG. 22, the remote operating unit 10052 can be included or integrated with a first surgical instrument 10060 and can be utilized to operate a second surgical instrument 10062, for example. In certain instances, the first surgical instrument 10060 can reside in a surgical field 10065 and can be manually operated by the operator from within the surgical field 10065, for example; and the second surgical instrument 10062 can reside outside the surgical field 10065. In certain instances, to avoid exiting the surgical field 10065, the operator may use the remote operating unit 10052 to remotely operate the second surgical instrument 10062 from within the surgical field 10065, for example. In certain instances, the second surgical instrument 10062 may be a circular stapler, for example. The entire disclosure of U.S. Pat. No. 8,360,297, entitled SURGICAL CUTTING AND STAPLING INSTRUMENT WITH SELF ADJUSTING ANVIL, which issued on Jan. 29, 2013, is incorporated by reference herein.

In various instances, the first surgical instrument 10060 and/or the second surgical instrument 10062 may include communication activation inputs (not shown). In such instances, actuating the communication activation inputs may be a precursory step to establishing communication between the first surgical instrument 10060 and the second surgical instrument 10062, for example; once communication is established, the operator may employ the remote operating unit 10052 to remotely control the second surgical instrument 10062, for example.

In various instances, a surgical system can include modular components that can be attached and/or combined together to form a surgical instrument. In certain instances, the modular components can be designed, manufactured, programmed, and/or updated at different times and/or in accordance with different software and/or firmware revisions and updates. For example, referring primarily to FIGS. 23 and 24, a surgical instrument 100 can include a first modular component 110, such as a handle, for example, and a second modular component 120, such as a shaft 122 and an end effector 124, for example, which are described in greater detail herein. In various circumstances, the first modular component 110 and the second modular component 120 can be assembled together to form the modular surgical instrument 100 or at least a portion thereof. Optionally, a different modular component may be coupled to the first modular component 110, such as shaft having different dimensions and/or features than those of the second modular component 120, for example. In various instances, the surgical instrument can include additional modular components, such as a modular battery, for example. Components of the modular surgical instrument 100 can include a control system that is designed and configured to control various elements and/or functions of the surgical instrument 100. For example, the first modular component 110 and the second modular component 120 can each comprise a control system, and the control systems of each modular component 110, 120 can communicate and/or cooperate. In various instances, the first modular component 110 may have been designed, manufactured, programmed, and/or updated at a different time and/or with different software and/or firmware than the second modular component 120, for example.

Figure 25:
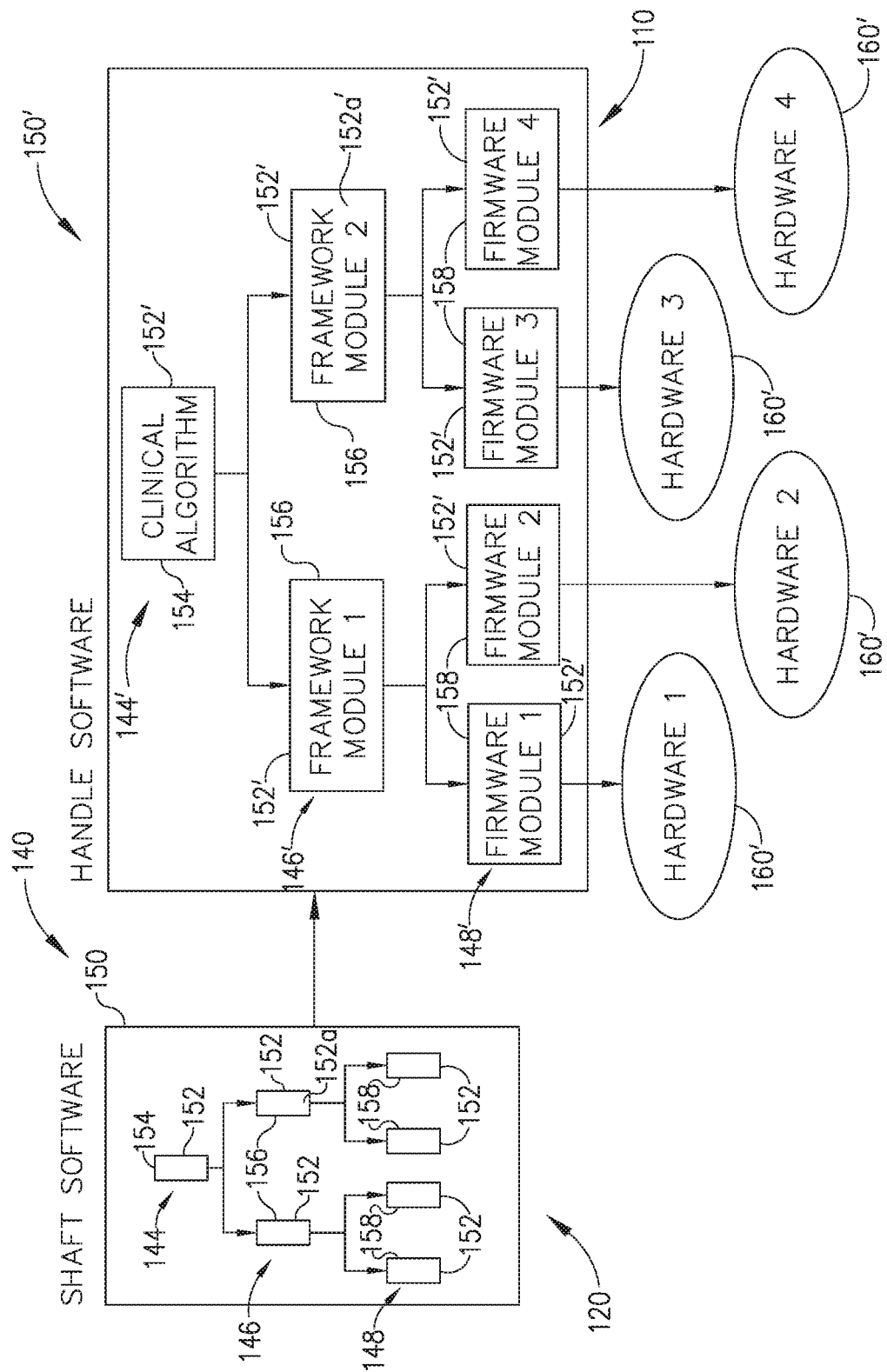
FIG. 25 is a schematic depicting the control systems of a modular surgical system according to various embodiments of the present disclosure.

Referring now to FIG. 25, the assembled surgical system can include a first control system 150' and a second control system 150. The control systems 150', 150 can be in signal communication, for example. In various instances, the second modular component 120 can comprise the control system 150, for example, which can include a plurality of control modules 152. The control modules 152 can affect a surgical function with and/or by an element or subsystem of the surgical instrument 100, for example. The control modules 152 can affect a surgical function based on a pre-programmed routine, operator input, and/or system feedback, for example. In various instances, the first modular component 110 can also comprise a control system 150', for example, which can include a plurality of control modules 152'. The control system 150' and/or one of the control modules 152' of the first modular component 110 may be different than the control system 150 and/or one of the control modules 152 of the second modular component 120. Though the control systems 150 and 150' can be different, the control systems 150 and 150' can be configured to control corresponding functions. For example, the control module 152(*a*) and the control module 152(*a*)' can both issue commands to firmware modules 158 to implement a firing stroke, for example. In various instances, one of the control systems 150, 150' and/or a control module 152, 152' thereof may include updated software and/or firmware and/or can have a more-recent effective date, as described in greater detail herein.

A control module 152, 152' can comprise software, firmware, a program, a module, and/or a routine, for example, and/or can include multiple software, firmware, programs, control modules, and/or routines, for example. In various circumstances, the control systems 150, 150' can include multiple tiers and/or levels of command. For example, the control system 150 can include a first tier 144 of control modules 152, a second tier 146 of control modules 152, and/or a third tier 148 of control modules 152. Control modules 152 of the first tier 144 can be configured to issue commands to the control modules 152 of the second tier 146, for example, and the control modules 152 of the second tier 146 can be configured to issue commands to the control modules 152 of the third tier 148. In various instances, the control systems 150, 150' can include less than three tiers and/or more than three tiers, for example.

Referring still to FIG. 25, the control module(s) 152 in the first tier 144 can comprise high-level software, or a clinical algorithm 154. The clinical algorithm 154 can control the high-level functions of the surgical instrument 100, for example. In certain instances, the control module(s) 152 in the second tier 146 can comprise intermediate software, or framework module(s) 156, which can control the intermediate-level functions of the surgical instrument 100, for example. In certain instances, the clinical algorithm 154 of the first tier 144 can issue abstract commands to the framework module(s) 156 of the second tier 146 to control the surgical instrument 100. Furthermore, the control modules 152 in the third tier 148 can comprise firmware modules 158, for example, which can be specific to a particular hardware component 160, or components, of the surgical instrument 100. For example, the firmware modules 158 can correspond to a particular cutting element, firing bar, trigger, sensor, and/or motor of the surgical instrument 100, and/or can correspond to a particular subsystem of the surgical instrument 100, for example. In various instances, a framework module 156 can issue commands to a firmware module 158 to implement a surgical function with the corresponding hardware component 160. Accordingly, the various control modules 152 of the surgical system 100 can communicate and/or cooperate during a surgical procedure.

Referring still to FIG. 25, the control system 150 of the second component 120 can correspond to the control system 150' of the first component 110, and the various control modules 152 of the second component 120 can correspond to the control modules 152' of the first component 110. Stated differently, each control module 152 can include a parallel, or corresponding control module 152', and both control modules 152 and 152' can be configured to perform identical, similar and/or related functions and/or to provide identical, similar and/or related commands. Referring still to FIG. 25, the control module 152a can correspond to the control module 152a'. For example, the control modules 152a and 152a' can both control the firing stroke of a cutting element; however, control module 152a can be configured to control a first cutting element design or model number and control module 152a' can be configured to control a different cutting element design or model number, for example. In other instances, the control module 152a' can comprise a software program and control module 152a can comprise an updated or revised version of the software program, for example.

In various instances, the first component 110 of the surgical instrument 100 can include a clinical algorithm 154' that is different than the clinical algorithm 154 of the second component 120. Additionally and/or alternatively, the first component 110 can include a framework module 156' that is different than a corresponding framework module 156 of the second component 120, and/or the first component 110 can include a firmware module 158' that is different than a corresponding firmware module 158 of the second component 120.

In various instances, corresponding control modules 152, 152' can comprise different effective dates. A person having ordinary skill in the art will appreciate that the effective date of a control module 152, 152' can correspond to a date that the control module 152, 152' was designed, created, programmed, and/or updated, for example. The effective date of a control module can be recorded or stored in the program code of the control module, for example. In certain instances, a control module of the surgical instrument 100 can be outdated. Furthermore, an out-of-date, or less-recently updated, control module may be incompatible with, disjointed from, and/or disconnected from an up-to-date and/or more-recently updated, control module. Accordingly, in certain instances, it may be desirable to update out-of-date control modules to ensure proper and effective operation of the surgical instrument 100.

In various instances, a modular component of the surgical system can include a predetermined default, or master, control system. In such instances, if the control systems of the assembled modular components are different, the default control system can update, overwrite, revise, and/or replace the non-default control systems. In other words, if corresponding control modules are different, incompatible, or inconsistent, for example, the non-default control module can be updated and the default control module can be preserved. For example, if the handle 110 comprises the control system 150', which is the non-default control system, and the shaft 120 comprises the control system 150, which is the master control system, the control system 150' of the handle 110 can be updated based on the control system 150 of the shaft 120.

It may be desirable to program a shaft component 120 of the surgical instrument to include the default control system in circumstances where shaft components are more frequently updated and/or modified than handle components. For example, if new generations and/or iterations of shaft components 120 are introduced more frequently than new generations and/or iterations of handle components 110, it may be advantageous to include a default, or master, control system in the shaft component 120 of the modular surgical instrument 100. Various circumstances described throughout the present disclosure relate to updating control modules of a handle component based on control modules of the shaft component; however, a person of skill in the art will readily appreciate that, in other contemplated circumstances, the control modules of the shaft component and/or a different modular component may be updated instead of or in addition to the control modules of the handle component.

Figure 26:
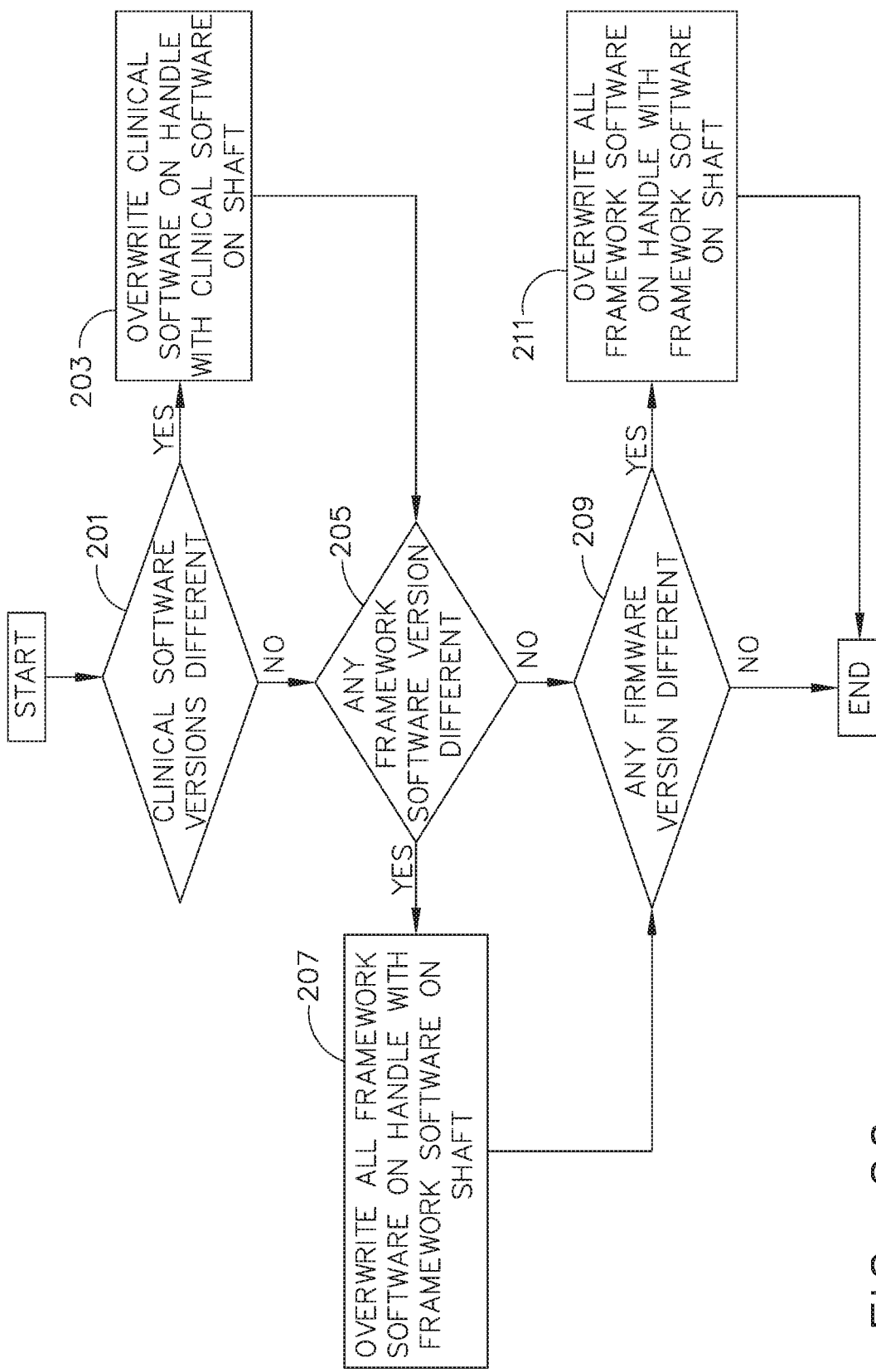
FIG. 26 is a flowchart depicting a method for updating a component of a modular surgical system according to various embodiments of the present disclosure.

In various instances, the surgical instrument 100 (FIGS. 23 and 24) can compare the control module(s) 152' at each tier or level in the control system 150' to the control module(s) 152 at each corresponding tier or level in the control system 150. If the control modules 152 and 152' in corresponding tiers are different, a control system 150, 150' can update the non-default control module(s), for example. Referring to FIG. 26, at step 201, the control system 150 and/or the control system 150' can compare the control module(s) 152' of the first tier 144' of the first component 110 to the control module(s) 152 of the first tier 144 of the second component 120. Where the first tiers 144, 144' comprise high-level clinical algorithms 154, 154', respectively, the control system 150 and/or the control system 150' can compare the clinical algorithms 154 and 154', for example. Furthermore, at step 203, if the control modules 152, 152' in the first tiers 144, 144' are different, the control system 150 and/or the control system 150' can update the module(s) 152' of the first tier 144' with the default module(s) 152 of the first tier 144, for example. In various instances, the control system 150 can compare and/or update a control system and/or control modules and, in other circumstances, the control system 150' can compare and update a control system and/or control modules, for example. In various instances, one of the control systems 150, 150' can be configured to compare and/or update a control system and/or control modules and, in other instances, both control systems 150, 150' can be configured to compare and/or update a control system and/or control modules.

At step 205, the control system 150 and/or the control system 150' can compare the control modules 152' of the second tier 146' of the first component 110 to the control modules 152 of the second tier 146 of the second component 120. For example, where the second tiers 146, 146' comprise mid-level framework algorithms 156, 156', the control systems 150, 150' can compare the framework algorithms 156 and 156', for example. At step 207, if the modules 152, 152' in the second tiers 146, 146' are different, the control systems 150, 150' can update the control modules 152' of the second tier 146' with the default control modules 152 of the second tier 146. In various instances, though one or more of the control modules 152' in the second tier 146' can be the same as a corresponding module 152 in the second tier 146, all control modules 152' of the second tier 146' can be updated if any corresponding second tier modules 152, 152' are different. In other instances, as described in greater detail herein, only the control module(s) 152' that is/are different than the corresponding module(s) 152 may be updated.

At step 209, the control systems 150 and/or the control system 150' can compare the control modules 152' of the third tier 148' of the first component 110 to the control modules 152 of the third tier 148 of the second component 120. For example, where the third tiers 148, 148' comprise firmware modules 158, 158', the control system 150 and/or the control system 150' can compare the firmware modules 158 and 158', for example. If the modules 152, 152' in the third tiers 148, 148' are different, the control system 150 and/or the control system 150' can update the control modules 152' of the third tier 148' with the default control modules 152 of the third tier 148 at step 211. In various instances, though one or more of the control modules 152' in the third tier 148' can be the same as a corresponding control module 152 in the third tier 148, all modules 152' of the third tier 148' can be updated if any corresponding third tier modules 152, 152' are different. In other instances, only the control module(s) 152' that is/are different than the corresponding control module(s) 152 may be updated, as described in greater detail herein. Referring still to FIG. 26, the first tier control modules 154, 154' can be updated prior to the second tier control modules 156, 156', for example, and the second tier control modules 156, 156' can be updated prior to the third tier control modules 158, 158', for example. In other instances, as described in greater detail herein, the third tier control modules 158, 158' can be updated prior to the second tier control modules 156, 156', for example, and the second tier control modules 156, 156' can be updated before the first tier control modules 154, 154', for example.

As described above, the control system 150 and/or the control system 150' may compare the control system 150, 150' and/or the control modules 152, 152' thereof prior to updating, replacing and/or overwriting an outdated control module 152, 152' and/or control systems 150, 150'. A reader will appreciate that this step can reduce the instrument startup time when software updates and/or upgrades are unnecessary or unmerited. Alternatively, the comparison steps 201, 205, and 209 could be eliminated, and the control systems 150, 150' may automatically update, replace, revise and/or overwrite the control module(s) 152' of the first modular component 110 and/or specific, predetermined control module(s) 152 of the first modular component 110, for example.

In various instances, the control modules 152, 152' can be compared and updated on a tier-by-tier basis and, in other instances, the control systems 150, 150' can be compared and updated on a system-by-system basis. In still other instances, the control modules 152, 152' can be updated on a module-by-module basis. For example, referring now to FIG. 27, at step 221, a third tier module 158' of the first control system 150' can be compared to a corresponding third tier module 158 of the second control system 150. In various instances, the effective date of the third tier module 158' can be compared to the effective date of the corresponding third tier module 158. Moreover, the control system 150 and/or the control system 150' can determine if the effective date of the third tier module 158' postdates the effective date of the third tier module 158. If the third tier module 158' is newer than the third tier module 158, for example, the third tier module 158' can be preserved at step 225. Conversely, if the third tier module 158' is not newer than the third tier module 158, i.e., the third tier module 158 predates the corresponding third tier module 158 or the third tier module 158 and the corresponding third tier module 158' have the same effective date, the third tier module 158' can be updated, replaced, revised, and/or overwritten by the corresponding third tier module 158, for example. Furthermore, in various instances, steps 221 and either 223 or 225 can be repeated for each module 158, 158' in the third tier of the control systems 150, 150'. Accordingly, the modules 158' in the third tier 148' may be updated on a module-by-module basis, and in various instances, only outdated modules 158' can be updated and/or overwritten, for example.

Figure 27:
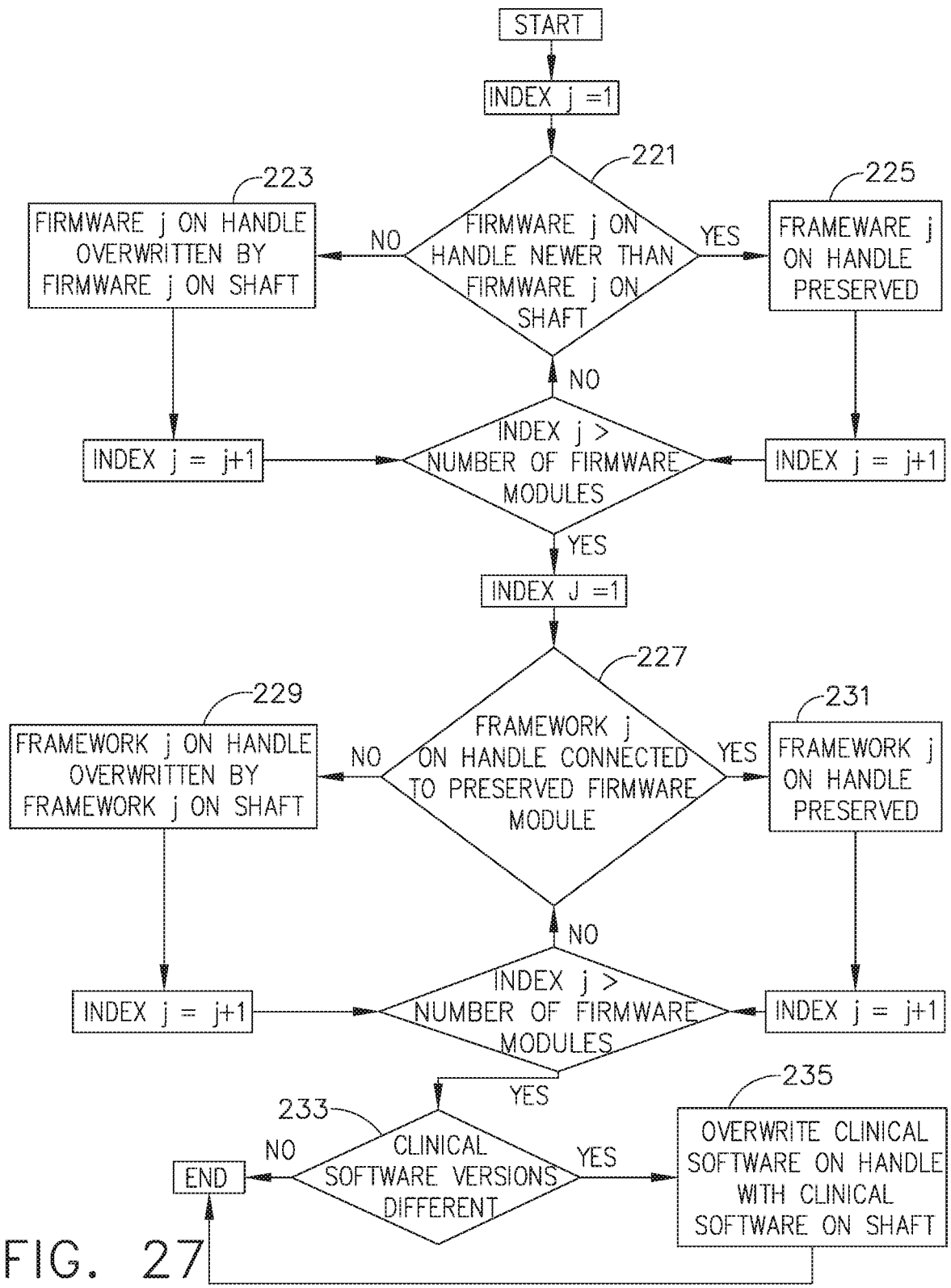
FIG. 27 is a flowchart depicting a method for updating a component of a modular surgical system according to various embodiments of the present disclosure.

Referring still to FIG. 27, after all third tier modules 158, 158' have been compared and possibly updated, the control systems 150, 150' can progress to step 227. At step 227, the control system 150 and/or the control system 150' can confirm that a third tier module 158' of the first control system 150' is connected and/or in proper communication with a second tier module 156' of the control system 150'. For example, in circumstances where the third tier module 158' was updated at step 223, the second tier module 156' may be disconnected from the updated third tier module 158'. If the third tier module 158' is disconnected from the second tier module 156', for example, the second tier module 156' can be updated, replaced, revised, and/or overwritten at step 229. The second tier module 156' can be replaced by the corresponding second tier module 156 of the second control system 150, for example. Conversely, if the third tier module 158' is properly connected and/or in communication with the second tier module 156', the second tier module 156' can be preserved. Furthermore, in various instances, steps 227 and either 229 or 231 can be repeated for each module 158, 158' in the third tier of the control systems 150, 150'. Accordingly, the modules 156' in the second tier 146' may be updated on a module-by-module basis, and in various instances, only disconnected modules 156' can be updated or overwritten, for example.

After updating any outdated third tier modules 158' (steps 221 and 223) and ensuring all updated third tier modules 158', if any, are connected to the appropriate second tier module 156' on the first modular component 110 (steps 227, 229, and 231), the control systems 150, 150' can progress to step 233, wherein the first tier module 154' of the first control system 150' can be compared to a corresponding first tier module 154 of the second control system 150. If the first tier modules 154, 154' are the same, the updating and/or revising process can be complete. Conversely, if the first tier modules 154, 154' are different, the first tier module 154' of the first control system 150' can be updated, replaced, revised, and/or overwritten by the first tier module 154 of the second control system 150.

As described herein, the software and/or firmware modules of the modular components 110, 120 can be updated, revised, and/or replaced on a module-by-module, tier-by-tier, and/or system-by-system basis. In certain instances, the updating and/or revision process can be automatic when the modular components are attached and/or operably coupled. In other circumstances, an operator of the surgical instrument 100 can initiate or trigger the updating and/or revision process described herein.

Figure 23:
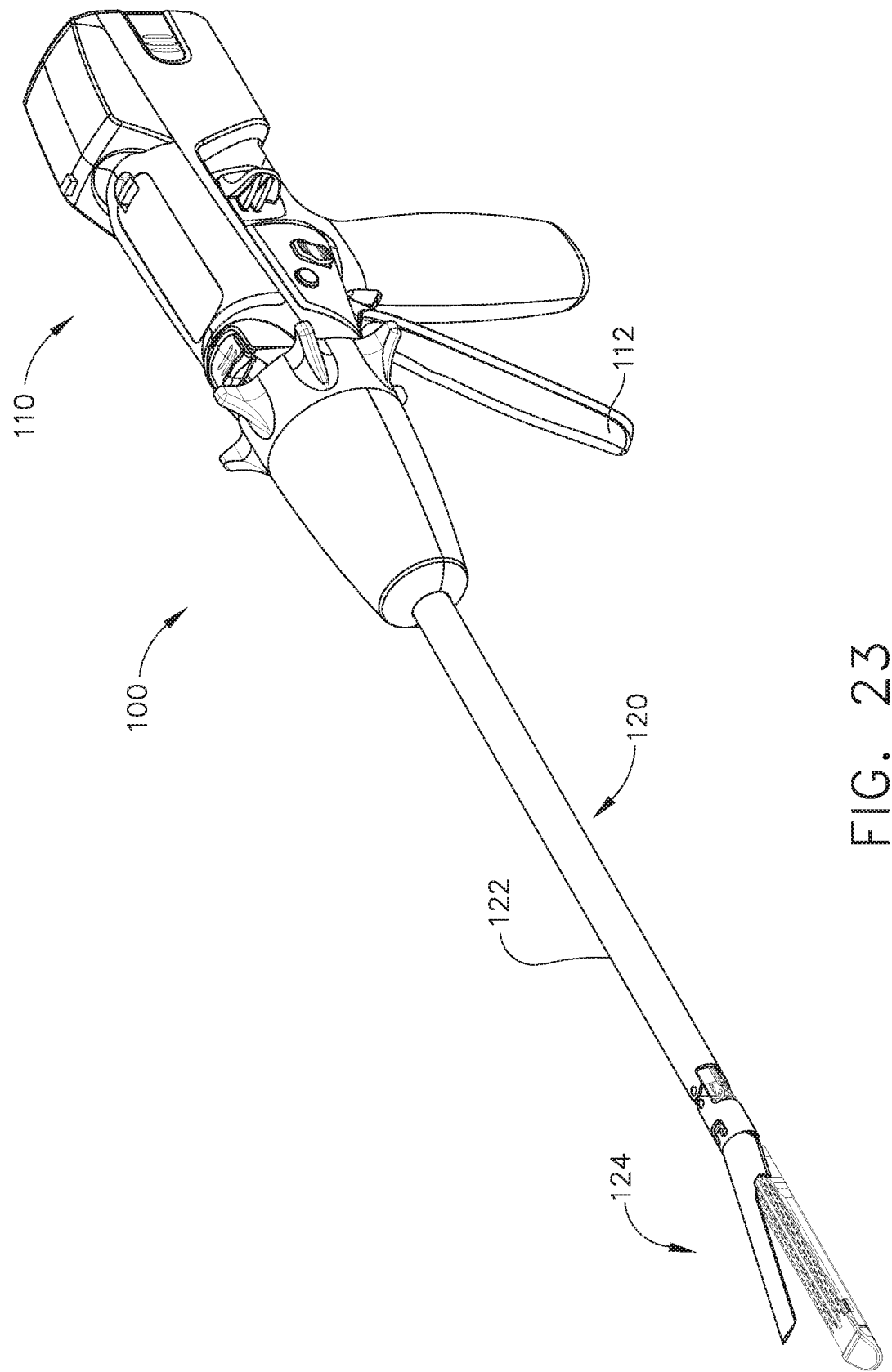
FIG. 23 is a perspective view of a modular surgical instrument according to various embodiments of the present disclosure.
Figure 24:
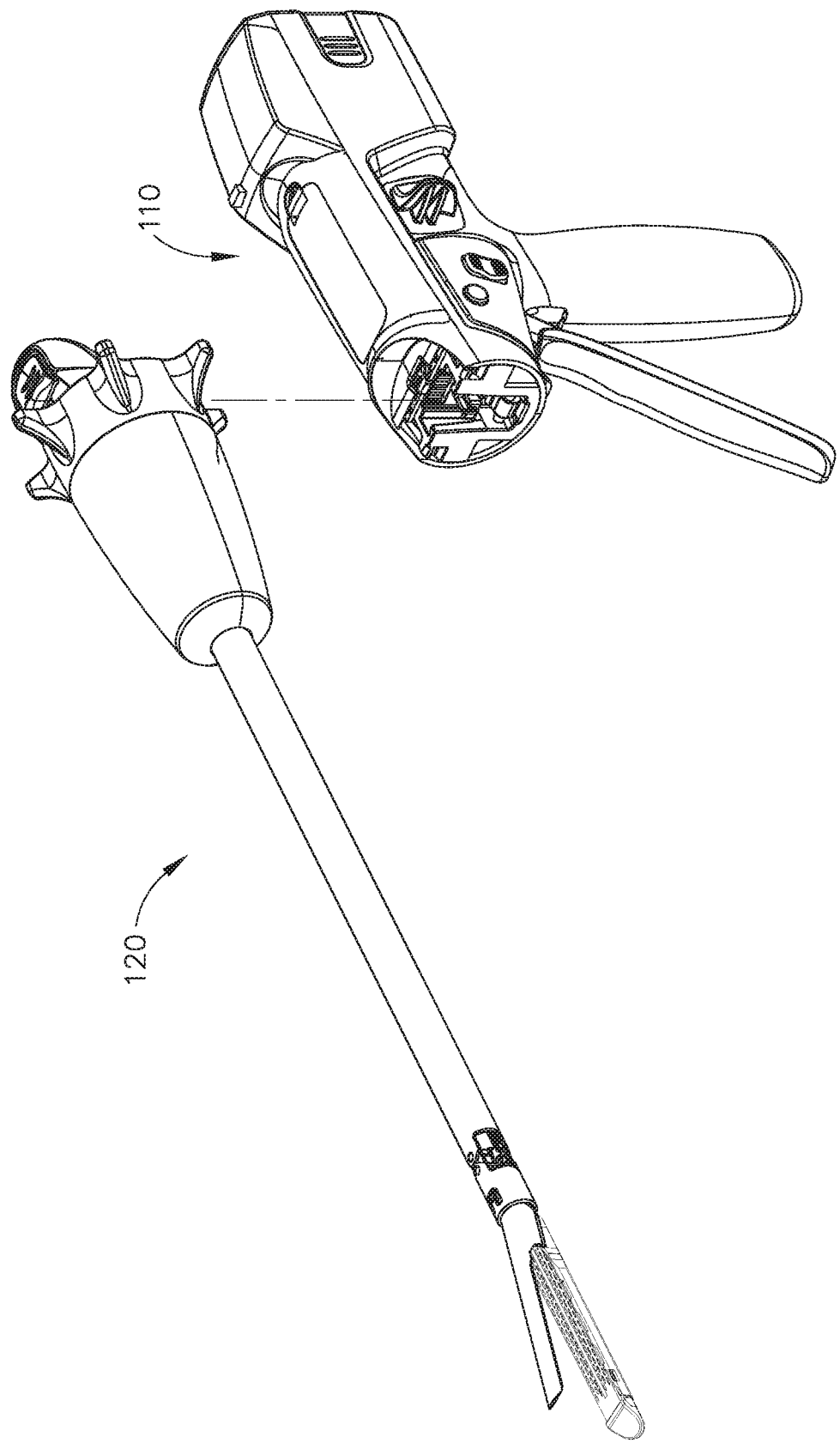
FIG. 24 is an exploded, perspective view of the modular surgical instrument of FIG. 23.

In various instances, a modular surgical instrument, such as the modular surgical instrument 100 (FIGS. 23 and 24), for example, can include a microcontroller in signal communication with an engagement sensor and a display. In various instances, the engagement sensor can detect the relative positioning of modular components of the surgical system. Referring again to FIGS. 23 and 24, where the first modular component 110 comprises a handle and the second modular component 120 comprises a shaft, for example, an engagement sensor can detect whether the shaft 120 is engaged with and/or operably coupled to the handle 110. In various instances, the shaft 120 can be moveable between engagement with the handle 110 (FIG. 23) and disengagement from the handle 110 (FIG. 24).

Figure 28A:
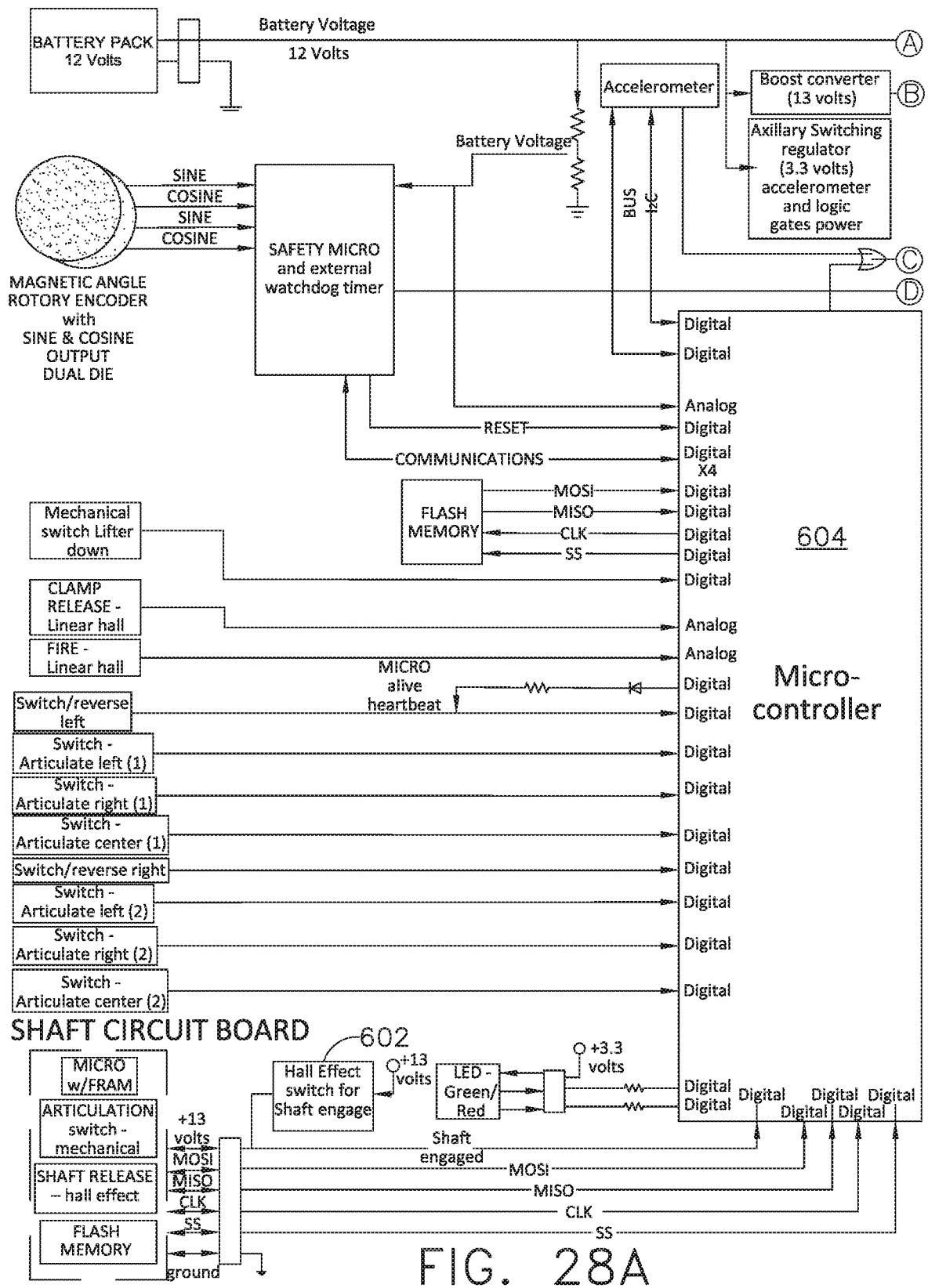
FIGS. 28(A) and 28(B) are schematics depicting a control circuit according to various embodiments of the present disclosure.
Figure 28B:
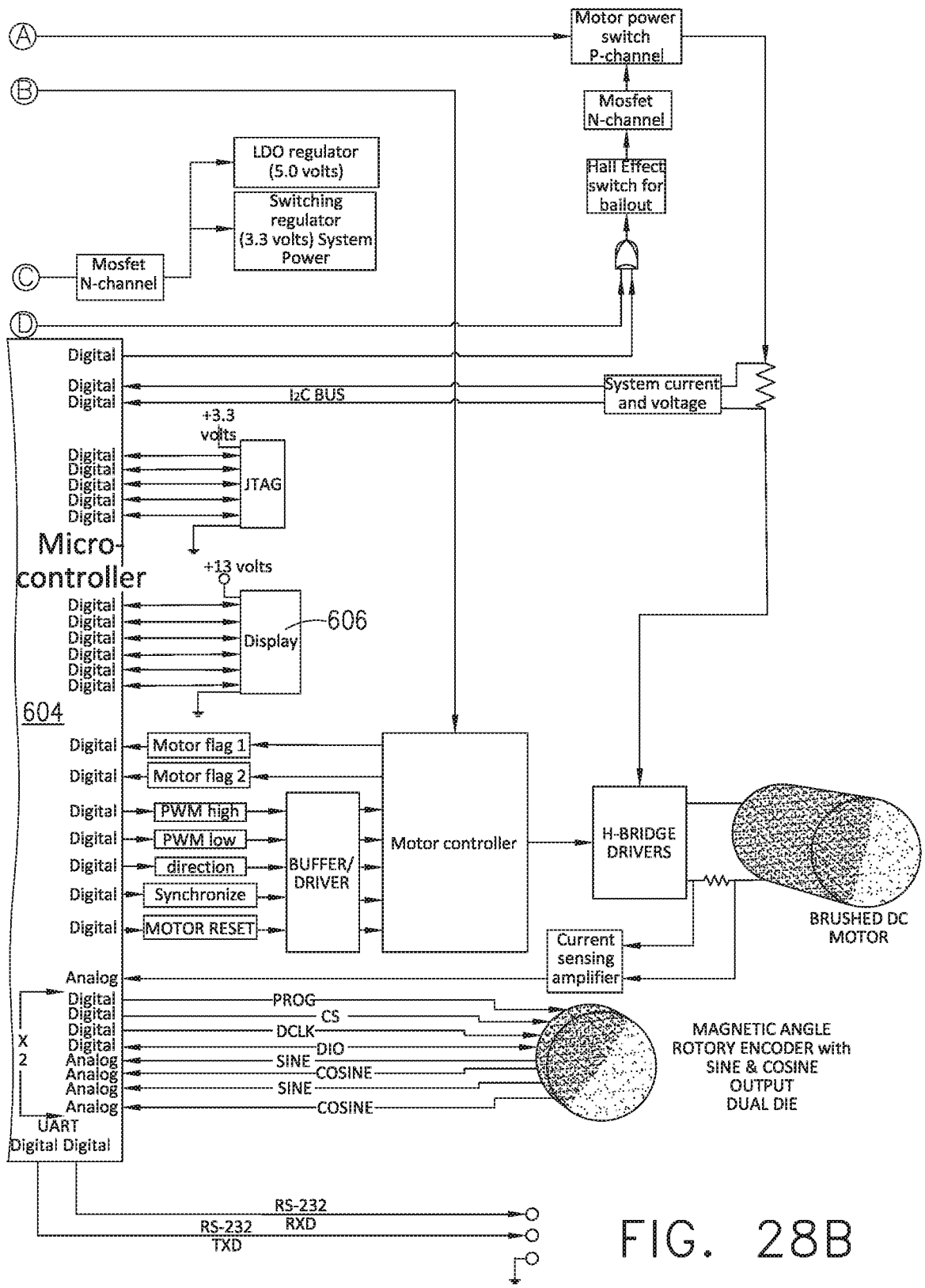

Referring primarily to FIGS. 28(A) and 28(B), an engagement sensor, such as the engagement sensor 602, for example, can be in signal communication with a microcontroller, such as the microcontroller 604, for example, of a surgical system. In various instances, the engagement sensor 602 can detect whether the modular components 110, 120 are engaged or disengaged, for example, and can communicate the engagement or lack thereof to the microcontroller 604, for example. When the engagement sensor 602 indicates that the shaft 120 is engaged with the handle 110, for example, the microcontroller 604 can permit a surgical function by the modular surgical instrument 100 (FIG. 23). If the modular components 110, 120 are operably coupled, for example, an actuation of the firing trigger 112 (FIG. 23) on the handle 110 can affect, or at least attempt to affect, a firing motion in the shaft 120, for example. Conversely, if the engagement sensor 602 indicates that the shaft 120 is disengaged from the handle 110, the microcontroller 604 can prevent a surgical function. For example, if the modular components 110, 120 are disconnected, an actuation of the firing trigger 612 may not affect, or not attempt to affect, a firing motion in the shaft 120.

In various instances, the modular surgical instrument 100 can include a display, such as the display 606 (FIG. 28(B)), for example. The display 606 can be integrated into one of the modular components 110, 120 of the surgical instrument 100 and/or can be external to the modular components 110, 120 and in signal communication with the microcontroller 604 of the surgical instrument 100. In various instances, the microcontroller 604 can communicate the information detected by the engagement sensor 602 to the display 606. For example, the display 606 can depict engagement and/or non-engagement of the modular components 110, 120. Moreover, in various instances, the display 606 can provide instructions and/or guidance regarding how to (a) properly attach, couple, and/or engage the disengaged components 110, 120 of the surgical instrument 100, and/or how to (b) properly un-attach, decouple, and/or disengage the engaged components 110, 120 of the surgical instrument 100. Referring again to FIG. 28(A), in various instances, the engagement sensor 604 can comprise a Hall Effect switch, and in other instances, the engagement sensor can comprise a different and/or additional sensor and/or switch, for example.

In certain circumstances, the engagement sensor 604 can detect the degree of engagement between modular components of a surgical instrument. In instances where the first component comprises the handle 110, for example, and the second component comprises the shaft 120, for example, the handle 110 and the shaft 120 can move between a disengaged position, a partially-engaged position, and an engaged position. The partially-engaged position can be intermediate the disengaged position and the engaged position, for example, and there may be multiple partially-engaged positions intermediate the engaged position and the disengaged position, for example. In various instances, the engagement sensor 604 can include a plurality of sensors, which can detect the partially-engaged position(s) of the components 110, 120. For example, the engagement sensor 606 can comprise a plurality of sensors and/or electrical contacts, for example, which can be staggered along an attachment portion of at least one of the modular components 110, 120, for example. In certain instances, the engagement sensor(s) 604 can comprise a Hall Effect sensor, for example.

Figure 29A:
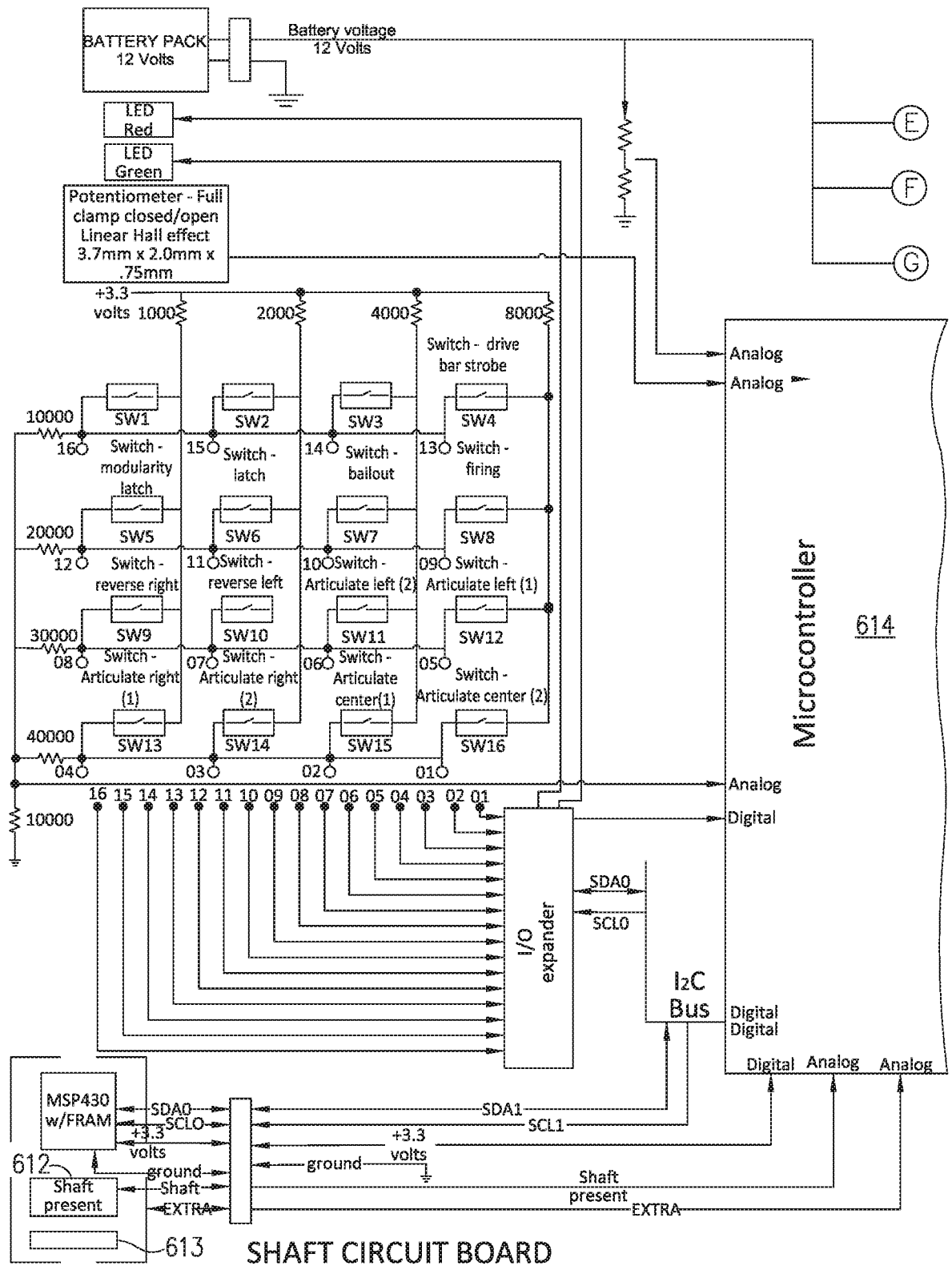
FIGS. 29(A) and 29(B) are schematics depicting a control circuit according to various embodiments of the present disclosure.
Figure 29B:
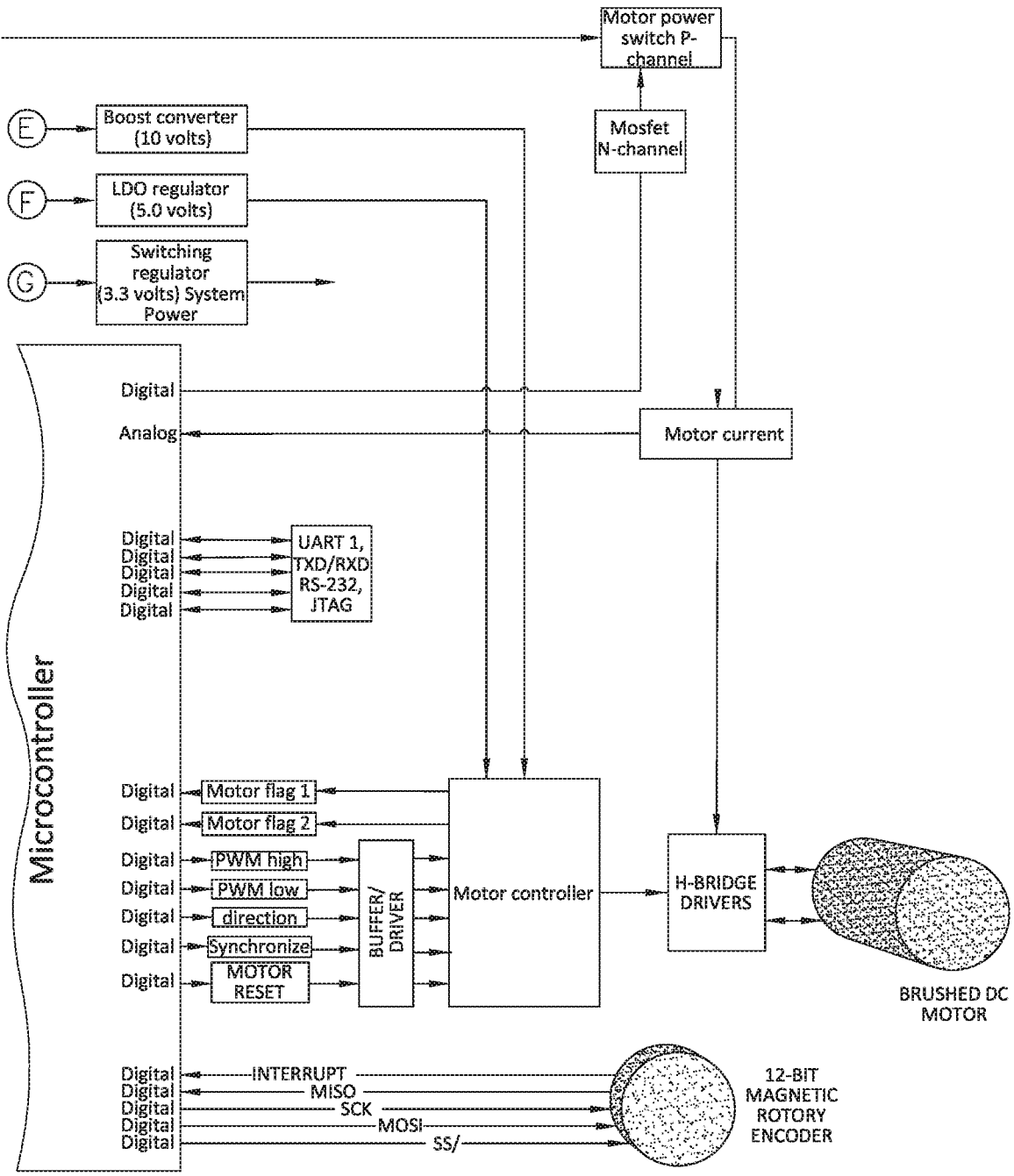

In certain instances, referring primarily to FIGS. 29(A) and 29(B), the surgical system 100 can include multiple sensors in signal communication with a microcontroller, such as the microcontroller 614, for example. The multiple sensors can include a first sensor 612 (FIG. 29(A)), which can detect the presence of the first component 120, and can communicate the presence of the first component 120 to the microcontroller 614, for example. In various instances, the first sensor 612 may not detect and/or communicate the degree of engagement between the first component 110 and the second component 120, for example. In various instances, a second sensor 613 (FIG. 29(A)) can also be in signal communication with the microcontroller 614. The second sensor 613 can detect the degree of engagement between the modular components 110, 120, for example.

Similar to the control system depicted in FIGS. 28(A) and 28(B), the microcontroller 614 can issue commands based on the feedback received from the sensors 612 and 613, and/or can be in signal communication with a display to display the feedback and/or otherwise communicate with an operator of the surgical system. For example, the microcontroller 614 can prevent a surgical function until the modular components 110, 120 are in the engaged position, and can prevent a surgical function when the modular components 110, 120 are partially-engaged, for example. Furthermore, the microcontroller 614 can communicate the information detected by the engagement sensor to a display. For example, the display can depict engagement, partial-engagement and/or non-engagement of the modular components 110, 120. Moreover, in various instances, the display can provide instructions and/or guidance regarding how to properly attach, couple, and/or engage disengaged and/or partially-engaged components 110, 120 of the surgical instrument, for example.

In various instances, a surgical instrument can include a microprocessor such as the microprocessor 604 (FIGS. 28(A) and 28(B)) or 614 (FIGS. 29(A) and 29(B)), for example, which can be in signal communication with a memory chip or memory unit. The microprocessor can communicate data and/or feedback detected and/or calculated by the various sensors, programs, and/or circuits of the surgical instrument to the memory chip, for example. In various instances, recorded data can relate to the time and/or duration of the surgical procedure, as well as the time and/or duration of various functions and/or portions of the surgical procedure, for example. Additionally or alternatively, recorded data can relate to conditions at the treatment site and/or conditions within the surgical instrument, for example. In certain instances, recordation of data can be automatic and, in other instances, the microprocessor may not record data unless and/or until instructed to record data. For example, it may be preferable to record data during a surgical procedure, maintain or store the recorded data in the memory chip, and/or transfer the recorded data to a secure site. In other circumstances, it may be preferable to record data during a surgical procedure and delete the recorded data thereafter, for example.

A surgical instrument and/or microcontroller thereof can comprise a data storage protocol. The data storage protocol can provide rules for recording, processing, storing, transferring, and/or deleting data, for example. In various instances, the data storage protocol can be preprogrammed and/or updated during the lifecycle of the surgical instrument. In various instances, the data storage protocol can mandate deletion of the recorded data after completion of a surgical function and/or surgical operation and, in other instances, the data storage protocol can mandate deletion of the recorded data after the elapse of a predefined period of time. For example, recorded data can be deleted, in accordance with the data storage protocol, one minute, one hour, one day, one week, one month or one year after the surgical function. The predefined period of time can be any suitable and appropriate period permitted by the circumstances.

Figure 31:
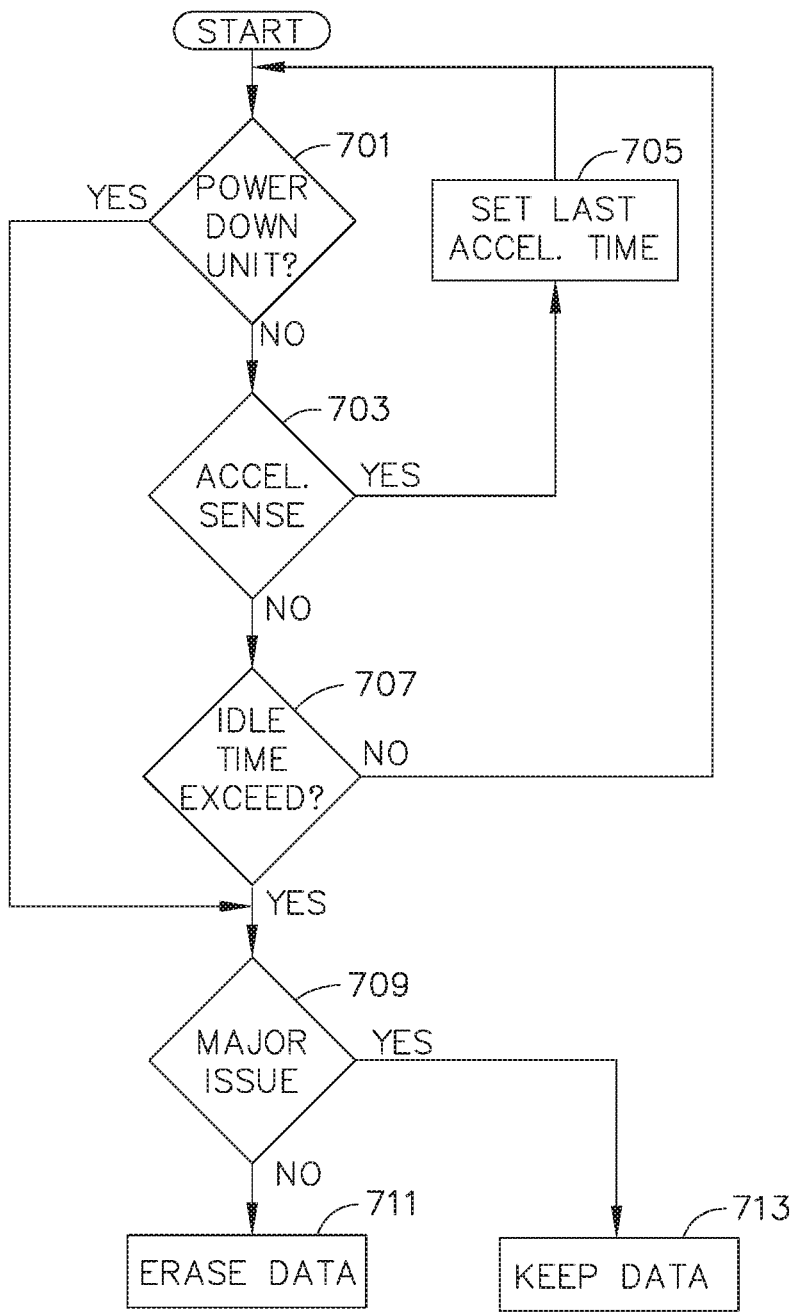
FIG. 31 is a flow chart depicting a method for processing data recorded by a surgical instrument according to various embodiments of the present disclosure.

In certain circumstances, the data storage protocol can mandate deletion of the recorded data after a predefined number of surgical functions, such as firing strokes, for example. In still other instances, the data storage protocol can mandate deletion of the recorded data when the surgical instrument is powered off. For example, referring to FIG. 31, if the surgical instrument is powered off, the microcontroller can proceed to step 709, wherein the microcontroller can determine if an error or major issue, such as an instrument, component or subsystem failure, for example, occurred during the surgical procedure. In various instances, if an error is detected, the microcontroller can proceed to step 713, wherein the data can be stored in the memory chip, for example. Moreover, in certain instances, if an error is not detected, the microcontroller can proceed to step 711, wherein the data can be deleted, for example. In other instances, the data storage protocol may not comprise the step 709, and the data storage protocol can continue without checking for a major error or failure, for example.

In still other instances, the data storage protocol can mandate deletion of the recorded data after a predefined period of inactivity or stillness of the surgical instrument. For example, if the surgical instrument is set down and/or put into storage, the data storage protocol can mandate deletion of the recorded data after the surgical instrument has been still or idle for a predefined period of time. The requisite period of stillness can be one minute, one hour, one day, one week, one month, or one year, for example. The predefined period of stillness can be any suitable and appropriate period permitted by the circumstances. In various instances, the surgical instrument can include an accelerometer, for example, which can detect movement and stillness of the surgical instrument. Referring again to FIG. 31, when the surgical instrument has not been powered off at step 701, the accelerometer can be set to detect movement of the surgical instrument. If movement is detected at step 703, prior to lapsing of the predefined idle period at step 707, the predefined idle time count can be restarted at step 705. Conversely, if movement is not detected by the accelerometer prior to lapsing of the predefined idle period at step 707, the microprocessor can proceed to step 709, for example. In other circumstances, the microprocessor can proceed directly to step 711 or 713, depending on the data storage protocol, without checking for an instrument error or failure, for example.

As described herein, the data storage protocol can include one of more default rules for deleting recorded data. In certain instances, however, it may be desirable to override the default rule or procedure. For example, for research and/or development purposes, it may be desirable to store recorded data for a longer period of time. Additionally or alternatively, it may be desirable to store recorded data for teaching and/or investigative purposes. Moreover, in various instances, the data storage protocol may not include an error-checking step and, in such instances, it may be desirable to override the data storage protocol and ensure storage of data when the operator detects or suspects an error and/or anomaly during a surgical procedure, for example. The recovered data can facilitate review of the procedure and/or a determination of the cause of the error, for example. In various instances, a key or input may be required to overcome or override the standard data storage protocol. In various instances, the key can be entered into the surgical instrument and/or a remote storage device, and can be entered by an operator and/or user of the surgical instrument, for example.

In various instances, a surgical system may prompt the user or instrument operator to select either data deletion or data storage for each surgical procedure or function. For example, the data storage protocol may mandate solicitation of instructions from the user, and may command subsequent action in accordance with the user's instructions. The surgical system may solicit instructions from the user upon the occurrence of a particular trigger event, such as powering down of the instrument, the elapse of a predefined period of time, or the completion of a particular surgical function, for example.

Figure 30:
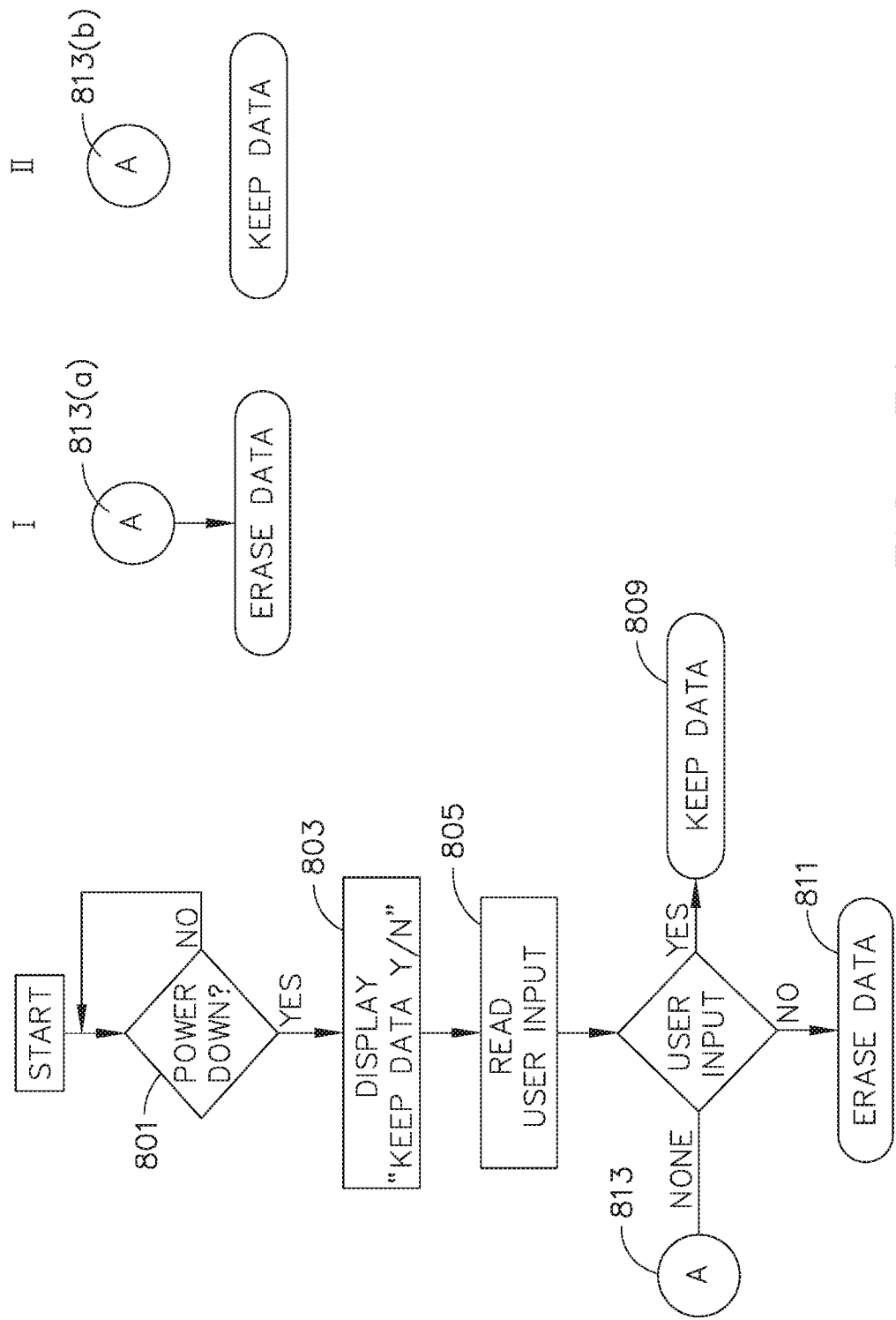
FIG. 30 is a flow chart depicting a method for processing data recorded by a surgical instrument according to various embodiments of the present disclosure.

In certain instances, the surgical system can request input from a user when the surgical instrument is powered down, for example. Referring to FIG. 30, when a user initiates powering off of a surgical instrument at step 801, for example, the surgical system can request data storage instructions from the user. For example, at step 803, a display of the surgical system can ask, "KEEP DATA Y/N?" In various instances, the microcontroller of the surgical system can read the user input at step 805. If the user requests storage of the data, the microcontroller can proceed to step 809, wherein the data is stored in a memory unit or memory chip of the surgical system. If the user requests deletion of the data, the microcontroller can proceed to step 811, wherein the data is erased. In various instances, the user may not enter input. In such instances, the data storage protocol can mandate a particular process at step 813. For example, the data storage protocol may mandate "Process I", "Process II", or an alternative process, for example. In certain instances, "Process I" can command the deletion of data at step 813(*a*), and "Process II" can command the storage of data at step 813(*b*), for example. In various circumstances, the user can provide instructions to the surgical instrument before instruction have been solicited, for example. Additionally or alternatively, a display associated with the surgical system can request instruction from the user prior to initiating the surgical function and/or at different time(s) during instrument use, for example.

If data is stored in the memory of the surgical instrument, the data can be securely stored. For example, a code or key may be required to access the stored data. In certain instances, the access key can comprise an identification code. For example, the identification code can be specific to the operator, user, or owner of the surgical instrument. In such instances, only an authorized person can obtain a licensed identification code, and thus, only authorized personnel can access the stored data. Additionally or alternatively, the access key can be specific to the instrument and/or can be a manufacturer's code, for example. In certain instances, the access key can comprise a secure server, and data can be transferred and/or accessed by an approved Bluetooth and/or radio frequency (RF) transmission, for example. In still other circumstances, the access key can comprise a physical key, such as memory key and/or a data exchange port connector, which can be physically coupled to a data exchange port of the surgical instrument. In such instances, the access key can be preprogrammed to obtain access to the secure data, and to securely store and/or transfer the data, for example. In various circumstances, an access key can correspond to a specific surgical instrument, for example.

In various instances, data extraction from the memory device of a surgical instrument can be restricted by various security measures. In certain instances, the memory device of the surgical instrument can comprise a secure data connection or data exchange port. For example, the data exchange port can have a proprietary geometry or shape, and only authorized personnel can obtain a corresponding port key designed and structured to fit the proprietary geometry or shape, for example. In various instances, the data exchange port can comprise a mechanical lock, which can comprise a plug, a plurality of pins, and/or a plurality of springs, for example. In various instances, a physical key or extraction device can unlock the mechanical lock of the data exchange port. For example, the physical key can contact the plurality of pins, deform the plurality of springs, and/or bias the plug from a locked orientation to an unlocked orientation to unlock the data exchange port, for example.

In various instances, the data exchange port can comprise at least one connection pin, which can be biased and/or held in a first position. When a physical key is inserted into and/or engages the data exchange port, the physical key can bias the connection pin from the first position to a second position, for example. In various instances, the first position can comprise a retracted position, for example, and the second position can comprise an extended position, for example. Moreover, when the connection pin is moved to the second position, the connection pin can operably interface with a data connection port in the physical key, for example. Accordingly, the data exchange port of the memory device can move into signal communication with the data exchange port of the physical key via the connection pin, for example, such that data can be exchanged and/or transferred therebetween. In various instances, the physical key can comprise a modular component, for example, which can be configured to removably attach to the modular surgical instrument. In certain instances, the physical key can replace or mimic a modular component 110, 120 of a surgical instrument 100 (FIGS. 23 and 24). For example, the physical key can attach to an attachment portion of the handle 110 in lieu of a shaft attachment 120, for example, for the transfer of data from a memory device in the handle 120.

Additionally or alternatively, the key or extraction device can comprise a security token. In various instances, the data exchange port can be encrypted, for example, and/or the key can provide information or codes to the data exchange port to verify that the key is authorized and/or approved to extract data from the data exchange port. In certain circumstances, the key can comprise a specialized data reader, for example, and data can be transferred via an optical data transmission arrangement, for example.

Figure 32:
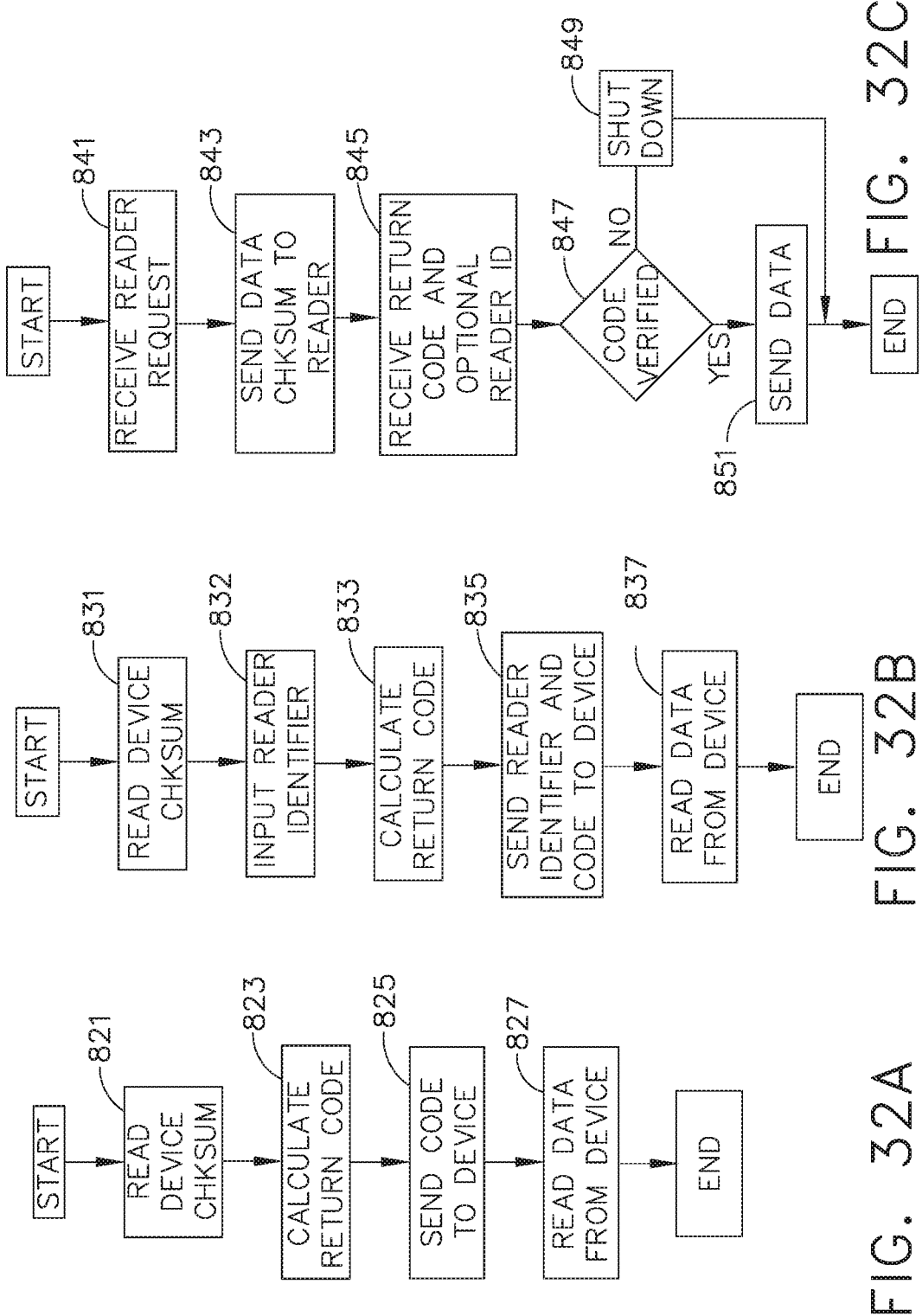
FIGS. 32(A)-32(C) are flow charts depicting various methods for processing data recorded by a surgical instrument according to various embodiments of the present disclosure.

Referring now to FIGS. 32(A)-32(C), before data access is granted to a proposed data reader, the data reader may need to be verified and/or confirmed by the surgical instrument. For example, the proposed data reader can request and read a checksum value of the surgical instrument at step 821. As depicted in the surgical instrument flowchart depicted in FIG. 32(C), the surgical instrument can first receive the proposed data reader request at step 841, and can then send the checksum value to the proposed data reader at step 843. Referring again to FIG. 32(A), at step 823, the proposed data reader can calculate or determine an appropriate return code based on the checksum value provided by the surgical instrument. The proposed data reader can have access to a code table, for example, and, if the proposed data reader is appropriately attempting to access the data, the appropriate return code can be available in the code table. In such instances, the proposed data reader can pull or calculate the return code at step 823 and can send the return code to the surgical instrument at step 825. Referring again to FIG. 32(C), upon receiving the return code from the proposed data reader at step 845, the surgical instrument can verify that the return code is correct at step 847. If the code is incorrect, the microprocessor of the surgical instrument can proceed to step 849, for example, and the surgical instrument can be shut down, or access to the stored data can be otherwise denied. However, if the code is correct, the microprocessor can proceed to step 851, for example, and the surgical instrument can provide data access to the proposed data reader. For example, the data can be securely transferred to the data reader at step 851. Thereafter, at step 827 (FIG. 32(A)), the proposed data reader can read the data from the surgical instrument, for example. In various instances, the transferred data can be encrypted, for example, and the data reader may need to decrypt the unintelligible data prior to reading it, for example.

Referring primarily to FIG. 32(B), an alternate data extraction security method can be similar to the method depicted in FIG. 32(A), for example, and can also require the consideration of a reader-specific code. Although the reader can read the checksum of the device at step 831 and the return code can be based on the checksum, in various circumstances, the proposed data reader can have a reader-specific code, and the appropriate return code from the code table can be based on the reader-specific code. For example, the proposed data reader can consider the reader-specific code at step 832, and can determine the appropriate return code at step 833 based on the reader-specific code and the code table, for example. The proposed data reader can provide the reader-specific code and the return code to the surgical instrument at step 835, for example. In such instances, referring again to FIG. 32(C), the microcontroller of the surgical instrument can verify the return code and reader-specific code, at step 845. Moreover, if these codes are correct, the surgical instrument can provide access to the proposed data reader. Thereafter, at step 827, the proposed data reader can read the data from the surgical instrument, for example. If one or both of the codes are incorrect, the surgical instrument can prevent the reader from reading the data. For example, the surgical instrument can shut down or otherwise restrict the transfer of data to the reader.

Figure 33:
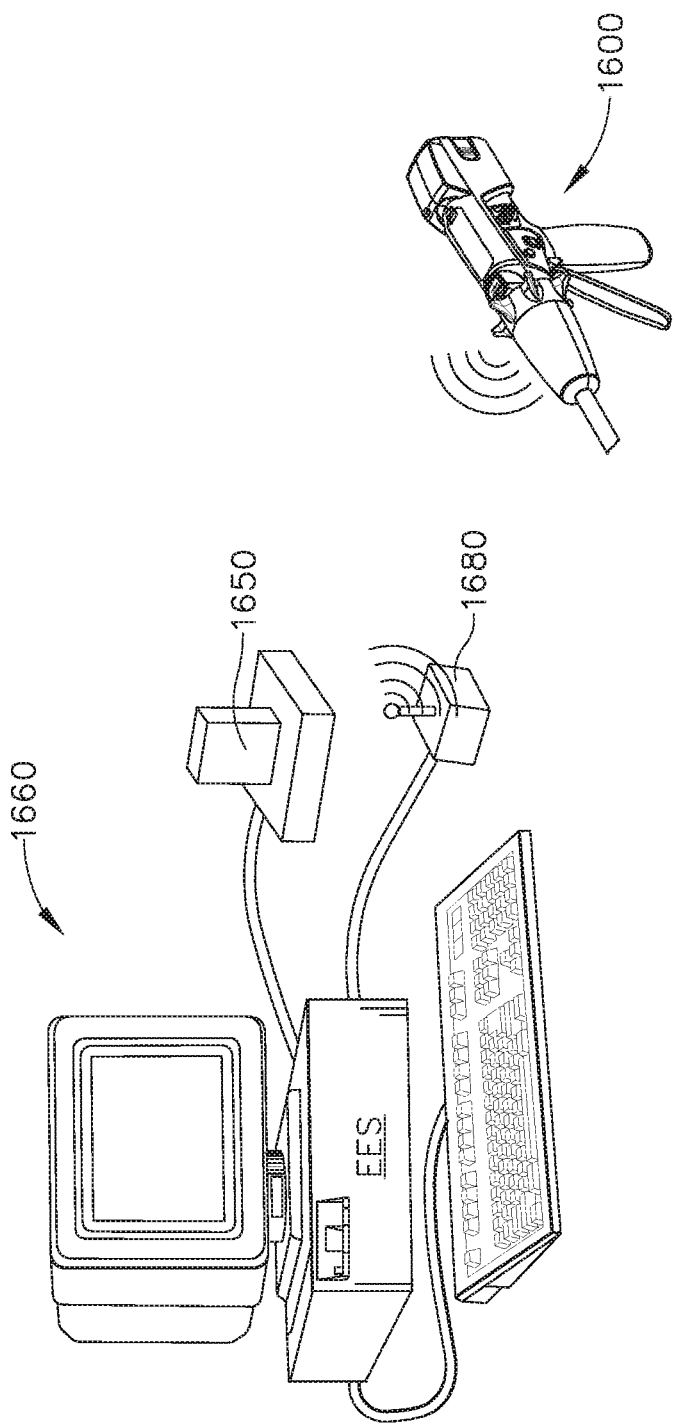
FIG. 33 is a schematic depicting a surgical system having wireless communication capabilities according to various embodiments of the present disclosure.

Referring now to FIG. 33, in various instances, a surgical system can comprise a surgical instrument 1600, which can be formed from a plurality of modular components. As described in greater detail herein, a handle component can be compatible with a plurality of different shaft components, for example, and the handle component and/or the shaft components can be reusable, for example. Moreover, a microcontroller of the surgical instrument 1600 can include a locking circuit, for example. In various instances, the locking circuit can prevent actuation of the surgical instrument until the locking circuit has been unlocked, for example. In various circumstances, the operator can enter a temporary access code into the surgical system to unlock the locking circuit of the microcontroller, for example.

In various circumstances, the operator can purchase or otherwise obtain the temporary access code for entering into the surgical system. For example, the instrument manufacturer or distributor can offer access codes for sale, and such access codes can be required in order to unlock, and thus use, the surgical instrument 1660. In various instances, the access code can unlock the locking circuit for a predefined period of time. The instrument manufacturer or distributor can offer different durations of use for purchase, and the user can select and purchase or acquire, a desired or preferable duration of use. For example, the user may acquire ten minutes of use, one hour of use, or one day of use. In other instances, additional and/or different suitable periods of use can be offered for sale or authorization. In various instances, after the acquired period of use expires, the locking circuit can be relocked. In other instances, an access code can unlock the locking circuit for a predefined number of surgical functions. For example, a user may purchase or otherwise obtain a single instrument firing or multiple firings, for example. Moreover, after the user has fired the instrument the purchased or authorized number of times, the locking circuit can be relocked. In still other instances, an access code can permanently unlock the locking circuit, for example.

In various instances, the operator can enter the temporary access code directly into the surgical system via a keypad or other suitable input arrangement. In other instances, the locking circuit can be unlocked by coupling a nonvolatile memory unit to the surgical instrument 1600, wherein the nonvolatile memory unit comprises a preprogrammed access code. In various instances, the nonvolatile memory unit can be loaded into a battery 1650 of the surgical instrument 1660, for example. Moreover, the nonvolatile memory unit can be reloaded and/or replaced. For example, the user can purchase replacement nonvolatile memory units. Additionally or alternatively, new codes can be purchased and uploaded to the nonvolatile memory unit, for example, after the previously-obtained access codes expire or lapse. In various instances, new codes can be loaded onto the nonvolatile memory unit when the battery 1650 is coupled to a power source and/or external computer 1670, for example.

In other instances, the temporary access code can be entered into an external or remote access code input, such as a display screen, computer, and/or heads up display. For example, a temporary access code can be purchased via a computer 1660, and can be transmitted to a radio frequency (RF) device 1680 coupled to the computer 1660. In various instances, the surgical instrument 1600 can comprise a receiver or antenna, which can be in signal communication with the radio frequency device 1680, for example. In such instances, the radio frequency device 1680 can transmit the acquired temporary access code(s) to the surgical instrument 1600 receiver, for example. Accordingly, the locking circuit can be unlocked, and the operator can use the surgical instrument 1600 for the purchased time period and/or number of surgical functions, for example.

In various instances, a modular surgical instrument may be compatible with an external display for depicting data and/or feedback from the surgical instrument. For example, the surgical instrument can comprise an instrument display for displaying feedback from the surgical procedure. In various instances, the instrument display can be positioned on the handle of the instrument, for example. In certain instances, the instrument display can depict a video feed viewed from an endoscope, for example. Additionally or alternatively, the display can detect sensed, measured, approximated, and/or calculated characteristics of the surgical instrument, surgical operation, and/or surgical site, for example. In various instances, it may be desirable to transmit the feedback to an external display. The external display can provide an enlarged view of the duplicated and/or reproduced feedback, for example, which can allow multiple operators and/or assistants to simultaneously view the feedback. In various instances, it may be desirable to select the surgical instrument for connection to the external display, for example, and, in other instances, the selection of a surgical instrument may be automatic.

Figure 34:
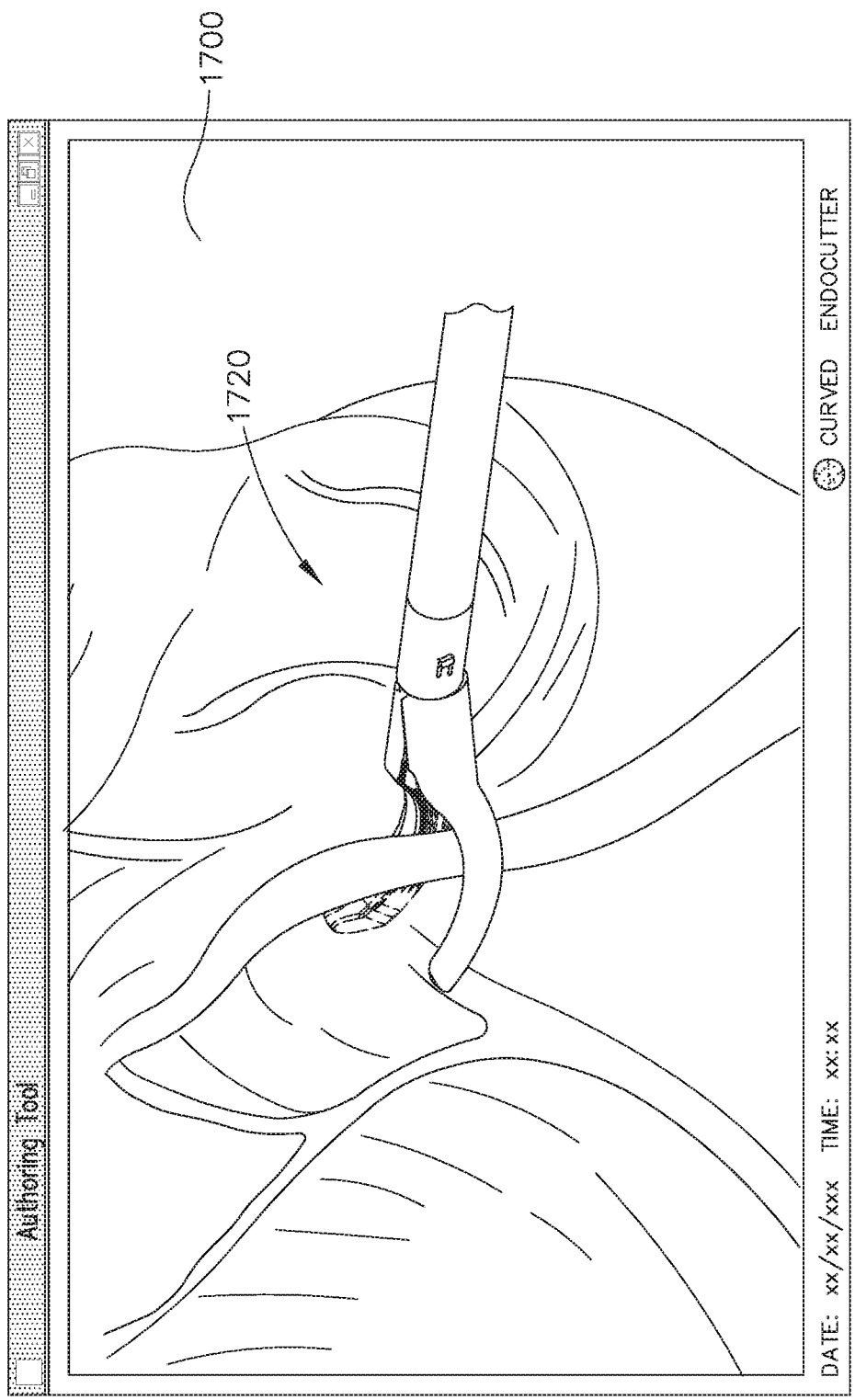
FIG. 34 is an elevation view of an external screen depicting an end effector at a surgical site according to various embodiments of the present disclosure.

Referring to FIG. 34, an external display 1700 can depict an end effector 1720 of a surgical instrument and/or the surgical site, for example. The external display 1700 can also depict feedback and/or data sensed and/or measured by the surgical instrument, for example. In various instances, the external display 1700 can duplicate feedback provided on the display of the surgical instrument. In certain circumstances, the surgical instrument can automatically connect with the external display 1700 and/or a wireless receiver in signal communication with the external, or operating room, display 1700, for example. In such instances, an operator can be notified if multiple surgical instruments are attempting to connect to the external display 1700. As described herein, the operator can select the desired surgical instrument(s) from a menu on the external display 1700, for example. In still other instances, the operator can select the desired surgical instrument by providing an input to the surgical instrument. For example, the operator can issue a command, control sequence, or input a code to select the surgical instrument. In various instances, the operator may complete a specific control sequence with the surgical instrument to select that surgical instrument. For example, the operator may power on the surgical instrument and, within a predefined period of time, hold down the reverse button for a predefined period of time, for example, to select the surgical instrument. When an instrument is selected, the feedback on the selected instrument display can be rebroadcast or duplicated on the external display 1700, for example.

Figure 35:
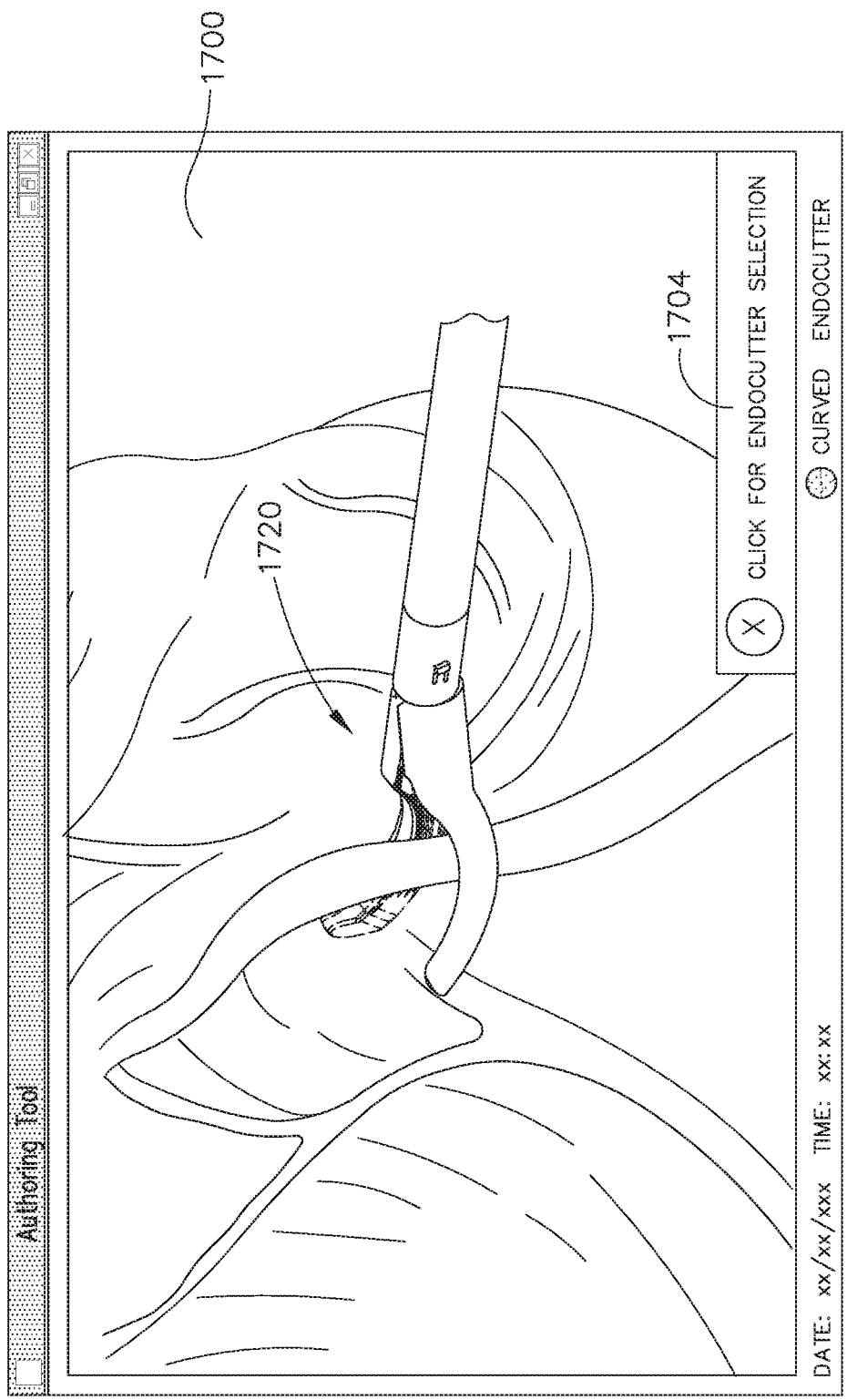
FIG. 35 is an elevation view of the external screen of FIG. 34 depicting a notification according to various embodiments of the present disclosure.
Figure 36:
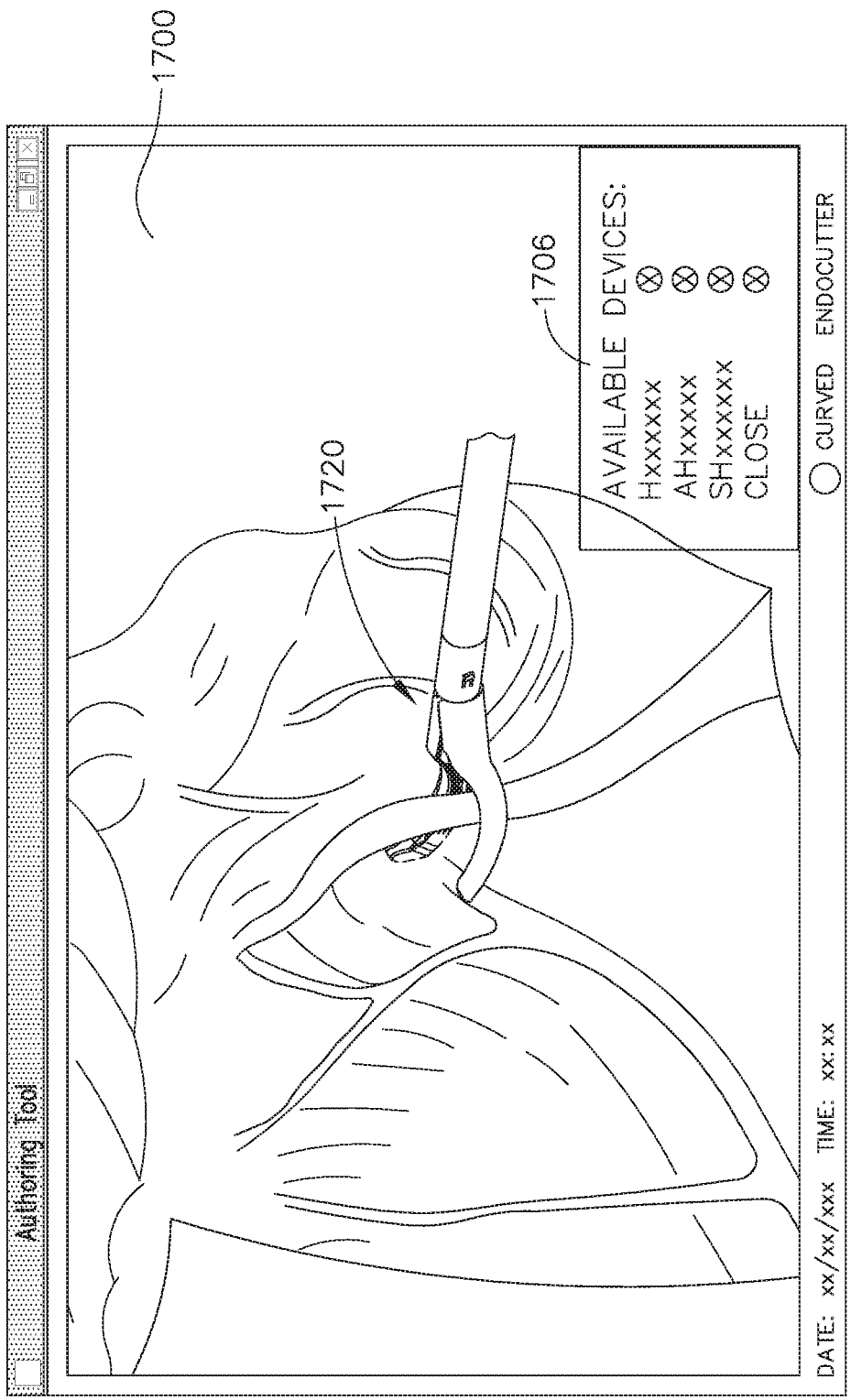
FIG. 36 is an elevation view of the external screen of FIG. 34 depicting a selection menu according to various embodiments of the present disclosure.

In certain instances, the surgical system can include a proximity sensor. For example, the external display and/or wireless receiver can comprise a proximity sensor, which can detect when a surgical instrument is brought within a predefined range thereof. Referring primarily to FIGS. 35 and 36, when the display 1700 and/or wireless receiver detect a surgical instrument, the display can notify the user. In certain circumstances, the display and/or wireless receiver may detect multiple surgical instruments. Referring to FIG. 35, the display 1700 can include a non-obtrusive notification 1704, for example, which can communicate to the user that a surgical instrument, or multiple surgical instruments, have been detected in the proximity of the display 1700. Accordingly, using the controls for the display 1700, such as a computer, for example, the user can click the notification 1704 to open the menu 1706 of instrument selections (FIG. 36). The menu 1706 can depict the available surgical instruments, for example, and the user can select the preferred surgical instrument for broadcasting on the display 1700. For example, the menu 1706 can depict the serial numbers and/or names of the available surgical instruments.

In certain instances, the selected surgical instrument can provide feedback to the operator to confirm its selection. For example, the selected surgical instrument can provide auditory or haptic feedback, for example. Additionally, the selected surgical instrument can broadcast at least a portion of its feedback to the external display 1700. In certain instances, the operator can select multiple surgical instruments and the display 1700 can be shared by the selected surgical instruments. Additionally or alternatively, the operating room can include multiple displays and at least one surgical instrument can be selected for each display, for example. Various surgical system features and/or components are further described in U.S. patent application Ser. No. 13/974,166, filed Aug. 23, 2013, and titled FIRING MEMBER RETRACTION DEVICES FOR POWERED SURGICAL INSTRUMENTS, which is hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009;

U.S. patent application Ser. No. 12/893,461, entitled STAPLE CARTRIDGE, filed Sep. 29, 2012, now U.S. Patent Application Publication No. 2012/0074198;

U.S. patent application Ser. No. 13/036,647, entitled SURGICAL STAPLING INSTRUMENT, filed Feb. 28, 2011, now U.S. Patent Application Publication No. 2011/0226837;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Pub. No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, are hereby incorporated by reference herein.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

As described earlier, the sensors may be configured to detect and collect data associated with the surgical device. The processor processes the sensor data received from the sensor(s).

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the collected biometric associated with motion data of the user, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the processor 3008 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument comprising:
a shaft;
an end effector extending distally from the shaft;
a display;
a processor coupled to the display;

a feedback system coupled to the processor, the feedback system configured to provide feedback as to a status of the surgical instrument; and a memory coupled to the processor, the memory storing program instructions that, when executed by the processor, cause the processor to:

cause the display to display directions communicating a subsequent step of use of the surgical instrument according to the status of the surgical instrument; and transition the display between a low-power mode and a high-power mode according to the status of the surgical instrument.

2. The surgical instrument of claim 1, wherein the subsequent step comprises a next step of operation of the surgical instrument.

3. The surgical instrument of claim 1, wherein the subsequent step comprises a next step of assembly or disassembly of the surgical instrument.

4. The surgical instrument of claim 1, wherein the feedback system comprises an accelerometer configured to detect movement of the surgical instrument, wherein the program instructions, when executed by the processor, further cause the processor to cause the display to transition to the low-power mode according to a lack of detection of movement after a predetermined period of time by the accelerometer.

5. The surgical instrument of claim 1, wherein the feedback system comprises an accelerometer configured to detect movement of the surgical instrument, wherein the program instructions, when executed by the processor, cause the processor to cause the display to transition to the high-power mode according to a detection of movement by the accelerometer.

6. The surgical instrument of claim 1, wherein the feedback system is configured to detect user contact with the surgical instrument, and wherein the program instructions, when executed by the processor, cause the processor to cause the display to transition to the low-power mode upon the surgical instrument detecting user contact.

7. A surgical instrument comprising:
an end effector;
a first modular component releasably connected to a second modular component;
a display;
a processor coupled to the display;
an engagement sensor configured to detect a degree of attachment between the first modular component and the second modular component, the engagement sensor operably connected to the processor;
wherein the degree of attachment comprises a disengaged position, a partially engaged position, and an engaged position; and
a memory coupled to the processor, the memory storing program instructions that, when executed by the processor, cause the surgical instrument to:
cause the display to display instructions corresponding to the degree of attachment;
determine whether the surgical instrument has exceeded a predetermined period of inactivity; and
cause the display to transition to a lower power mode following the predetermined period of inactivity.

8. The surgical instrument of claim 7, wherein the first modular component comprises a handle and the second modular component comprises a shaft, the end effector extending distally from the shaft.

9. The surgical instrument of claim 7, wherein the engagement sensor comprises an electrical contact disposed at an attachment portion between the first modular component and the second modular component.

10. The surgical instrument of claim 7, further comprising an accelerometer operably connected to the processor, and wherein the accelerometer is configured to generate an input according to whether movement is detected.

11. The surgical instrument of claim 10, wherein the accelerometer is configured to detect movement in a plurality of directions, and wherein the accelerometer is configured to generate the input according to whether movement is detected in at least two of the plurality of directions.

12. The surgical instrument of claim 10, wherein the accelerometer is configured to detect movement in a plurality of directions, and wherein the accelerometer is configured to generate the input according to whether movement above a predetermined threshold is detected.

13. The surgical instrument of claim 7, wherein an input is generated by the surgical instrument according to whether user contact is detected.

14. A surgical instrument comprising:
a shaft;
an end effector extending distally from the shaft;
a display;
a processor coupled to the display;
a feedback system coupled to the processor, the feedback system configured to provide feedback as to an operational status of the surgical instrument; and
a memory coupled to the processor, the memory storing program instructions that, when executed by the processor, cause the processor to:
present instructions via the display, the instructions communicating a next step of operating the surgical instrument corresponding to the operational status of the surgical instrument; and
transition the display between a low-power mode and a high-power mode according to an activity of the surgical instrument.

15. The surgical instrument of claim 14, further comprising an accelerometer configured to detect movement of the surgical instrument, wherein the program instructions, when executed by the processor, cause the processor to cause the display to transition to the high-power mode according to a detection of movement by the accelerometer.

16. The surgical instrument of claim 14, further comprising an accelerometer configured to detect movement of the surgical instrument, wherein the program instructions, when executed by the processor, cause the processor to cause the display to transition to the low-power mode according to a lack of detection of movement by the accelerometer over a predetermined period of time.

17. The surgical instrument of claim 14, wherein the feedback system is configured to monitor a configuration of the end effector.

18. The surgical instrument of claim 14, the instructions of the next step of operation corresponding to the operational status of the surgical instrument are displayed in a defined order.

19. The surgical instrument of claim 14, wherein the next step of operation comprises an articulation step, a closure step, a firing step, a firing reset step, a closure reset step, an articulation reset step, and combinations thereof.

* * * * *